(12) United States Patent
Yaghi et al.

(10) Patent No.: US 8,916,722 B2
(45) Date of Patent: Dec. 23, 2014

(54) COMPLEX MIXED LIGAND OPEN FRAMEWORK MATERIALS

(75) Inventors: Omar M. Yaghi, Los Angeles, CA (US); Christian J. Doonan, Los Angeles, CA (US); Hexiang Deng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 364 days.

(21) Appl. No.: 13/378,300

(22) PCT Filed: Jun. 18, 2010

(86) PCT No.: PCT/US2010/039154
§ 371 (c)(1), (2), (4) Date: Jun. 27, 2012

(87) PCT Pub. No.: WO2010/148296
PCT Pub. Date: Dec. 23, 2010

(65) Prior Publication Data
US 2012/0259135 A1    Oct. 11, 2012

Related U.S. Application Data

(60) Provisional application No. 61/218,879, filed on Jun. 19, 2009, provisional application No. 61/246,004, filed on Sep. 25, 2009.

(51) Int. Cl.
*C07F 3/00* (2006.01)
*B01J 20/22* (2006.01)

(52) U.S. Cl.
CPC ........... *C07F 3/003* (2013.01); *B01D 2253/204* (2013.01); *B01J 20/226* (2013.01)
USPC .......................................... 556/132

(58) Field of Classification Search
USPC .......................................... 556/132
See application file for complete search history.

(56) References Cited

U.S. PATENT DOCUMENTS

| | | | |
|---|---|---|---|
| 2,684,967 A | 7/1954 | Berg | |
| 4,532,225 A | 7/1985 | Tsao et al. | |
| 5,160,500 A | 11/1992 | Chu et al. | |
| 5,208,335 A | 5/1993 | Ramprasad et al. | |
| 5,648,508 A | 7/1997 | Yaghi et al. | |
| 5,733,505 A | 3/1998 | Goldstein et al. | |
| 6,479,447 B2 | 11/2002 | Bijl et al. | |
| 6,501,000 B1 | 12/2002 | Stilbrany et al. | |
| 6,617,467 B1 | 9/2003 | Muller et al. | |
| 6,624,318 B1 | 9/2003 | Mueller et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Mueller et al. | |
| 7,343,747 B2 | 3/2008 | Mueller et al. | |
| 7,411,081 B2 | 8/2008 | Mueller et al. | |
| 7,524,444 B2 | 4/2009 | Hesse et al. | |
| 7,582,798 B2 | 9/2009 | Yaghi et al. | |
| 7,652,132 B2 | 1/2010 | Yaghi et al. | |
| 7,662,746 B2 | 2/2010 | Yaghi et al. | |
| 7,799,120 B2 | 9/2010 | Yaghi et al. | |
| 7,815,716 B2 | 10/2010 | Mueller et al. | |
| 2003/0004364 A1 | 1/2003 | Yaghi et al. | |
| 2003/0078311 A1 | 4/2003 | Muller et al. | |
| 2003/0148165 A1 | 8/2003 | Muller et al. | |
| 2003/0222023 A1 | 12/2003 | Mueller et al. | |
| 2004/0081611 A1 | 4/2004 | Muller et al. | |
| 2004/0225134 A1 | 11/2004 | Yaghi et al. | |
| 2004/0249189 A1 | 12/2004 | Mueller et al. | |
| 2004/0265670 A1 | 12/2004 | Muller et al. | |
| 2005/0004404 A1 | 1/2005 | Muller et al. | |
| 2005/0014371 A1 | 1/2005 | Tsapatsis | |
| 2005/0124819 A1 | 6/2005 | Yaghi et al. | |
| 2005/0154222 A1 | 7/2005 | Muller et al. | |
| 2005/0192175 A1 | 9/2005 | Yaghi et al. | |
| 2006/0057057 A1 | 3/2006 | Muller et al. | |
| 2006/0135824 A1 | 6/2006 | Mueller et al. | |
| 2006/0154807 A1 | 7/2006 | Yaghi et al. | |
| 2006/0185388 A1 | 8/2006 | Muller et al. | |
| 2006/0252641 A1 | 11/2006 | Yaghi et al. | |
| 2006/0252972 A1 | 11/2006 | Pilliod et al. | |
| 2006/0287190 A1 | 12/2006 | Eddaoudi et al. | |
| 2007/0068389 A1 | 3/2007 | Yaghi et al. | |
| 2007/0202038 A1 | 8/2007 | Yaghi et al. | |
| 2008/0017036 A1 | 1/2008 | Schultink et al. | |
| 2008/0184883 A1 | 8/2008 | Zhou et al. | |
| 2009/0155588 A1 | 6/2009 | Hesse et al. | |

(Continued)

FOREIGN PATENT DOCUMENTS

| DE | 102005023856 A1 | 11/2006 |
|---|---|---|
| DE | 102005054523 A1 | 5/2007 |

(Continued)

OTHER PUBLICATIONS

Doonan et al., "Exceptional ammonia uptake by a covalent organic framework", Nature Chemistry, vol. 2, Mar. 2, 2010, pp. 235-238.

Doonan, C., "Hydrogen Storage in Metal-Organic Frameworks," Annual Merit Review Proceedings of DOE Hydrogen Program, May 22, 2009.

Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.

(Continued)

*Primary Examiner* — Porfirio Nazario Gonzalez

(74) *Attorney, Agent, or Firm* — Joseph R. Baker, Jr.; Gavrilovich, Dodd & Lindsey LLP

(57) ABSTRACT

The disclosure provides multivariate metal organic frameworks comprising different functional ligands.

20 Claims, 31 Drawing Sheets

(56) References Cited

U.S. PATENT DOCUMENTS

| | | |
|---|---|---|
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2010/0286022 A1 | 11/2010 | Yaghi et al. |
| 2011/0137025 A1 | 6/2011 | Yaghi et al. |

FOREIGN PATENT DOCUMENTS

| | | |
|---|---|---|
| EP | 1674555 A1 | 6/2006 |
| KR | 10-2010-0055350 | 5/2010 |
| WO | 2004101575 A2 | 11/2004 |
| WO | 2006072573 A2 | 7/2006 |
| WO | 2006116340 A1 | 11/2006 |
| WO | 2006125761 A2 | 11/2006 |
| WO | 2007054581 A2 | 5/2007 |
| WO | 2007101241 A2 | 9/2007 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A9 | 2/2009 |
| WO | 2009042802 A1 | 4/2009 |
| WO | 2009056184 A1 | 5/2009 |
| WO | 2009149381 A2 | 12/2009 |
| WO | 2010078337 A1 | 7/2010 |
| WO | 2010080618 A1 | 7/2010 |
| WO | 2010083418 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011014503 A1 | 2/2011 |
| WO | 2011038208 A2 | 3/2011 |
| WO | 2011146155 A9 | 11/2011 |
| WO | 2012012495 A3 | 1/2012 |
| WO | 2012082213 A2 | 6/2012 |
| WO | 2012100224 A3 | 7/2012 |
| WO | 2012106451 A2 | 8/2012 |

OTHER PUBLICATIONS

Duren et al., "Design of New Materials for Methane Storage," Langmuir 20:2683-2689 (2004).

Eddaoudi et al., "Porous Germanates: Synthesis, Structure, and Inclusion Properties of Ge7O14.5F2.[(CH3)2NH2]3 (H20)0.86", J. Am. Chem. Soc. 1998, 120, 8567-8568.

Eddaoudi et al., "Design and Synthesis of Metal-Carboxylate Frameworks with Permanent Porosity," In Topics in Catalysis, G. A. Somorjai and J. M. Thomas, Eds., 9:105 (1999).

Eddaoudi et al., "Highly Porous and Stable Metal-Organic Framework: Structure Design and Sorption Properties," J. Am. Chem. Soc. 121:1391-1397 (2000).

Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).

Eddaoudi et al., "Modular Chemistry: Secondary Building Units as a Basis for the Design of Highly Porous and Robust Metal-Organic Carboxylate Frameworks" Acc. Chem. Res. 34:319-330 (2001).

Eddaoudi et al., "Geometric Requirements and Examples of Important Structures in the Assembly of Square Building Blocks," Proc. Natl. Acad. Sci. 99:4900-4904 (2002).

Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.

Eddaoudi et al., "Cu2[o-Br-C6H3(CO2)2]2(H2O)2•(DMF)8(H2O)2: A Framework Deliberately Designed to have the NbO Structure Type," J. Am. Chem. Soc.124:376-377 (2002).

El-Kaderi et al., "Designed Synthesis of 3D Covalent Organic Frameworks", Science 316, 268 (2007).

El-Kaderi et al., "Supporting Online Material for Designed Synthesis of 3D Covalent Organic Frameworks", Science 316, 268 (2007).

Ferragut et al., "Positronium Formation in Porous Materials for Antihydrogen Production", Journal of Physics: Conference Series 225 (2010), pp. 1-8.

Foster et al., "A High-Throughput Investigation of the Role of pH, Temperature, Concentration, and Time on the Synthesis of Hybrid Inorganic-Organic Materials", Angew. Chem. Int. Ed. 2005, 44, 7608-7611.

Fracaroli et al., "Isomers of Metal-Organic Complex Arrays", Inorg. Chem. 2012, 51, 6437-6439.

Furukawa et al., "Crystal Structure, Dissolution, and Deposition of a 5 nm Functionalized Metal-Organic Great Rhombicuboctahedron," J. Am. Chem. Soc. 128:8398-8399 (2006).

Furukawa et al., "Independent verification of the saturation hydrogen uptake in MOF-177 and establishment of a benchmark for hydrogen adsorption in metal-organic frameworks," J. Mater. Chem. 17:3197-3204 (2007).

Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).

Furukawa et al., "Storage of Hydrogen, Methane, and Carbon Dioxide in Highly Porous Covalent Organic Frameworks for Clean Energy Applications", J. Am. Chem. Soc. 2009, 131, 8875-8883.

Furukawa et al., "Ultra-High Porosity in Metal-Organic Frameworks," Science 239:424-428 (2010).

Furukawa et al., "Isoreticular Expansion of Metal-Organic Frameworks with Triangular and Square Building Units and the Lowest Calculated Density for Porous Crystals", Inorg. Chem. 2011, 50, 9147-9152.

Gadzikwa et al., "Selective Bifunctional Modification of a Non-catenated Metal-Organic Framework Material via "Click" Chemistry", J. Am. Chem. Soc. 2009, 131, 13613-13615.

Galli et al., "Adsorption of Harmful Organic Vapors by Flexible Hydrophobic Bis-pyrazolate Based MOFs", Chem. Mater 2010, 22, 1664-1672.

Gandara et al., "Porous, Conductive Metal-Triazolates and Their Structural Elucidation by the Charge-Flipping Method", Chem. Eur. J. 2012, 18, 10595-10601.

Gassensmith et al., "Strong and Reversible Binding of Carbon Dioxide in a Green Metal-Organic Framework", J. Am. Chem. Soc. 2011, 133, 15312-15315.

Glover et al., "MOF-74 building unit has a direct impact on toxic gas adsorption," J. Chem. Eng. Sci. 66:163-170 (2011).

Goebel, Matthias, Supplemental European Search Report and Written Opinion for EP08826913. Date of Completion of Search and Written Opinion: Nov. 10, 2010.

Goebel, Matthias, Supplemental European Search Report and Written Opinion for EP08754337. Date of Completion of Search and Written Opinion: Dec. 3, 2010.

Goto et al., ""Clickable" Metal-Organic Framework", J. Am. Chem. Soc. 2008, 130, 14354-14355.

Gould et al., "The Amphidynamic Character of Crystalline MOF-5: Rotational Dynamics in a Free-Volume Environment," J. Am. Chem. Soc. 130:3246-3247 (2008).

Grzesiak et al., "Polymer-Induced Heteronucleation for the Discovery of New Extended Solids," Angew. Chem. Int. Ed. 45:2553-2556 (2006).

Halper et al., "Topological Control in Heterometallic Metal-Organic Frameworks by Anion Templating and Metalloligand Design," J. Am. Chem. Soc. 128:15255-15268 (2006).

Han et al., "Improved Designs of Metal-Organic Frameworks for Hydrogen Storage", Angew. Chem. Int. Ed. 2007, 46, 6289-6292.

Han et al., "Covalent Organic Frameworks as Exceptional Hydrogen Storage Materials", J. Am. Chem. Soc. 2008, 130, 11580-11581.

Hayashi et al., "Zeolite A Imidazolate Frameworks," Nature Materials 6:501-506 (2007).

Hexiang et al., "Multiple Functional Groups of Varying Rations in Metal-Organic Frameworks," Science 327 (5967):846-850 (2010).

Hmadeh et al., "New Porous Crystals of Extended Metal-Catecholates", Chem. Mater. 2012, 24, 3511-3513.

(56) References Cited

OTHER PUBLICATIONS

Holler et al., "The first dinitrile frameworks of the rare earth elements: [LnCI3(1,4-Ph(CN)2] and [Ln2CI6(1,4Ph(CN)2], Ln = Sm, Gd, Tb, Y; Access to novel metal-organic frameworks by solvent free synthesis in molten 1,4-benodinitrile," Inorganic Chemistry 47(21): 10141-9 (2008).
Huang et al., "Ligand-Directed Stragegy for Zeolite-Type Metal-Organic Frameworks: Zinc(II) Imidazolates with Unusual Zeolitic Topologies", Angew. Chem. Int. Ed. 2006, 45, 1557-1559.
Huang et al., "Thermal Conductivity of Metal-Organic Framework 5 (MOF-5): Part II. Measurement," Int. J. Heat Mass Transfer 50:405-411 (2007).
Hunt et al., "Reticular Synthesis of Covalent Organic Borosilicate Frameworks", J. Am. Chem. Soc., 2008, 130, 11872-11873.
Jeong et al., "Asymmetric Catalytic Reactions by NbO-Type Chiral Metal-Organic Frameworks," Chem. Sci. 2:877-882 (2011).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Klein et al., "Combinatorial Material Libraries on the Microgram Scale with an Example of Hydrothermal Synthesis," Angew. Chem. Int. Ed. 1998, 37 No. 24, pp. 3369-3372.
Klemperer et al., "New Directions in Polyvanadate Chemistry: From Cages and Clusters to Baskets, Belts, Bowls, and Barrels", Angew. Chem. Int. Ed. Engl. 31 (1992) No. 1, pp. 49-51.
Koh et al., "A Crystalline Mesoporous Coordination Copolymer with High Microporosity", Angew. Chem. Int. Ed. 2008, 120, pp. 689-692.
Li et al., "Coordinatively Unsaturated Metal Centers in the Extended Porous Framewokr of Zn3(BDC)3-6CH3OH (BDC= 1,4-Benzenedicarboxylate)," J. Am. Chem. Soc. 2186-2187 (1998).
Plevert et al., "A Flexible Germanate Structure Containing 24-Ring Channels With Very Low Framework Density," J. Am. Chem. Soc. 123:12706-12707 (2001).
Plevert et al., "Synthesis and Characterization of Zirconogermanates," Inorg. Chem., 42:5954-5959 (2003).
Plevert et al., "Layered Structures Constructed from New Linkages of Ge7(O,OH,F)19 Clusters," Chem. Mater. 15:714-718 (2003).
Prajapati et al., "Metal-organic frameworks (MOFs) constructed from Znll/Cdll-2,2'-bipyridines and polycarboxylic acids: Synthesis, characterization and microstructural studies", Polyhedron 28 (2009) 600-608.
Queen et al., "Site-Specific CO2 Adsorption and Zero Thermal Expansion in an Anisotropic Pore Network," J. Phys. Chem. C 2011, 115, 24915-24919.
Reineke et al., "From Condensed Lanthanide Coordination Solids to Microporous Frameworks Having Accessible Metal Sites," J. Am. Chem. Soc 121:1651-1657 (1999).
Reineke et al., "A Microporous Lanthanide-Organic Frameworks," Angew. Chem. Int. Ed. 38:2590-2594 (1999).
Reineke et al., "Large Free Volume in Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).
Rosi et al., "Infinite Secondary Building Units and Forbidden Catenation in Metal-Organic Frameworks," Angew. Chem. Int. Ed. 41:294-297 (2002).
Rosi et al., "Advances in the Chemistry of Metal-Organic Frameworks," CrystEngComm 4:401-404 (2002).
Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.
Rosi et al., "Rod-Packings and Metal-Organic Frameworks Constructed from Rod-Shaped Secondary Building Units," J. Am. Chem. Soc. 127:1504-1518 (2005).
Rowsell et al., "Hydrogen Sorption in Functionalized Metal-Organic Frameworks," J. Am. Chem. Soc.126: 5666-5667 (2004).
Rowsell et al., "Metal-Organic Frameworks: A New Class of Porous Materials," Microporous Mesoporous Mater. 73:3-14 (2004).
Rowsell et al., "Strategies for Hydrogen Storage in Metal-Organic Frameworks," Angew. Chem. Int. Ed. 44: 4670-4679 (2005).
Rowsell et al., "Gas Adsorption Sites in a Large-Pore Metal-Organic Framework," Science 309:1350-1354 (2005).
Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).
Shi-Jie et al., "Synthesis and Structural Characterization of a New 3D Lead Coordination Polymer with a Tetrazole-1-acetate Ligand", Chinese J. Struct. Chem., vol. 30, No. 7, 2011, pp. 1049-1053.
Siberio-Perez, "Raman Spectroscopic Investigation of CH4 and N2 Adsorption in Metal-Organic Frameworks," Chem. Mater. 19:3681-3685 (2007).
Smaldone et al., "Metal-Organic Frameworks from Edible Nature Products," Angew. Chem. Int. Ed. 49:8630-8634 (2010).
Song et al., "Hydrothermal Synthesis and Structural Characterization of Three-dimensional Metal-organic Framework Zn3(C2H2N3)2(C7H5O2)4]", Chem. Res. Chinese Universities 2009, 25(1), 1-4.
Song et al., "A Multiunit Catalyst with Synergistic Stability and Reactivity: A Polyoxometalate-Metal Organic Framework for Aerobic Decontamination", J. Am. Chem. Soc. 2011, 133, 16839-16846.
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Spitler et al., "Lewis acid-catalysed formation of two-dimensional phthalocyanine covalent organic frameworks", Nature Chemistry, vol. 2, Aug. 2010, pp. 672-677.
Stallmach et al., "NMR Studies on the Diffusion of Hydrocarbons on the Metal-Organic Framework Material MOF-5," Angew. Chem. Int. Ed. 45:2123-2126 (2006).
Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).
Sudik et al., "Metal-Organic Frameworks Based on Trigonal Prismatic Building Blocks and the New "acs" Topology," Inorg. Chem. 44:2998-3000 (2005).
Sudik et al., "A Metal-Organic Framework with a Hierarchical System of Pores and Tetrahedral Bbuilding Blocks," Angew. Chem. Int. Ed. 45:2528-2533 (2006).
Tilford et al., "Facile Synthesis of a Highly Crystalline, Covalently Linked Porous Boronate Network", Chem. Mater. 2006, 18, 5296-5301.
Tranchemontagne et al. "Metal-Organic Frameworks with High Capacity and Selectivity for Harmful Gases," Proc. Natl. Acad. Sci. USA 105:11623-11627 (2008).
Tranchemontagne et al., "Reticular Chemistry of Metal-Organic Polyhedra," Angew. Chem. Int. Ed., 2008, 47:5136-5147 (2008).
Tranchemontagne et al., "Room Temperature Synthesis of Metal-organic Frameworks: MOF-5, MOF-74, MOF-177, MOF-199, and IRMOF-0," Tetrahedron 64:8553-8557 (2008).
Tranchemontagne et al. "Secondary Building Units, Nets and Bonding in the Chemistry of Metal-Organic Frameworks," Chem. Soc. Rev. 38:1257-1283 (2009).
Tranchemontagne et al., "Hydrogen Storage in New Metal-Organic Frameworks", J. Phys. Chem. C 2012, 116, 13143-13151.
Uribe-Romo et al., "A Crystalline Imine-Linked 3-D Porous Covalent Organic Framework", J. Am. Chem. Soc. 2009, 131 (13), 4570-4571.
Uribe-Romo et al., "Crystalline Covalent Organic Frameworks with Hydrazone Linkages", J. Am. Chem. Soc. 2011, 133, 11478-11481.
Vairaprakash et al., "Synthesis of Metal-Organic Complex Arrays," J. Am. Chem. Soc. 133:759-761 (2011).

(56) References Cited

OTHER PUBLICATIONS

Valente et al., "Metal-organic Frameworks with Designed Chiral Recognition Sites," Chem. Commun. 46: 4911-4913 (2010).
Vitillo et al., "Role of Exposed Metal Sites in Hydrogen Storage in MOFs", J. Am. Chem. Soc. 2008, 130, 8386-8396.
Vodak et al., "Metal-Organic Frameworks Constructed from Pentagonal Antiprismatic and Cuboctahedral Secondary Building Units," Chem. Commun. 2534-2535 (2001).
Vodak et al., "One-Step Synthesis and Structure of an Oligo(spiro-orthocarbonate)", J. Am. Chem. Soc. 2002, 124, 4942-4943.
Vodak et al., "Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wan et al., "A Belt-Shaped, Blue Luminescent, and Semiconducting Covalent Organic Framework," Angew. Chem. Int. Ed. 2008, 47, 8826-8830.
Wan et al., "Covalent Organic Frameworks with High Charge Carrier Mobility," Chem. Mater. 2011, 23, 4094-4097.
Wang et al., "Postsynthetic Covalent Modification of a Neutral Metal-Organic Framework", J. Am. Chem. Soc. 2007, 129, 12368-12369.
Wang et al., "Colossal Cages in Zeolitic Imidazolate Frameworks as Selective Carbon Dioxide Reservoirs," Nature 453:207-211 (2008).
Wang et al., "Tandem Modification of Metal-Organic Frameworks by a Postsynthetic Approach," Angew. Chem. Int. Ed. 2008, 47, 4699-4702.
Wang, Chinese Patent Application No. CN201080036940.6, Chinese Patent Office, Chinese Office Action, Dec. 24, 2013.
Akporiaye et al., "Combinatorial Approach to Hydrothermal Synthesis of Zeolites", Angew. Chem. Int. Ed., 1998, 37, No. 5, 609-611.
Baharlou, Simin. International Preliminary Report on Patentability for PCT/US2009/046463. Date of Mailing: Dec. 16, 2010.
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46: 7981-7983 (2010).
Barman et al., "Incorporation of active metal sites in MOFs via in situ generated ligand deficient metal-linker complexes", Chem. Comm., 2011, pp. 1-3.
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Metal-Organic frameworks with high capacity and selectivity for harmful gases", PNAS, 2008, vol. 105, No. 33, pp. 11623-11627.
Britt et al., "Highly efficient separation of carbon dioxide by a metal-organic framework replete with open metal sites," Proc. Natl. Acad. Sci. USA 106:20637-20640 (2009).
Britt et al., "Ring-Opening Reactions within Porous Metal-Organic Frameworks", Inorg. Chem. 2010, 49, 6387-6389.
Carlucci et al., "Nanoporous three-dimensional networks topologically related to cooperite from the self-assembly of copper(I)centres and teh 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).

Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 4, (3) New Scientist, Feb. 4.
Che et al., "Mono- and Diprotonation of the [(n5-C5H5)Ti(W5O18)]3- and [(n5-C5Me5)Ti(W5O18)]3- Anions," Inorg. Chem. 1992, 31, 2920-2928.
Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al. "Photoluminescent Metal-Organic Polymer Constructed from Trimetallic Clusters and Mixed Carboxylates", Inorg. Chem. 2003, 42, 944-946.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Chen et al., "Noncovalently Netted, Photoconductive Sheets with Extremely High Carrier Mobility and Conduction Anisotropy from Triphenylene-Fused Metal Trigon Conjugates", J. Am. Chem. Soc. 2009, 131, 7287-7292.
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Choi et al., "Reversible Interpenetration in a Metal-Organic Framework Triggered by Ligand Removal and Addition", Angew. Chem. Int. Ed., 2012, 51, 8791-8795.
Corma et al., "A large-cavity zeolite with wide pore windows and potential as an oil refining catalyst", Nature, vol. 418, Aug. 2002, pp. 514-517.
Coskun et al., "Metal-Organic Frameworks Incorporating Copper-Complexed Rotaxanes", Angew. Chem. Int. Ed. 2012, 51, 2160-2163.
Cote et al., "Reticular Synthesis of Microporous and Mesoporous 2D Covalent Organic Frameworks," J. Am. Chem. Soc. 2007, 129, 12914-12915.
Cote et al., "Porous, Crystalline, Covalent Organic Frameworks", Science, 310, 1166 (2005).
Cui et al., "In Situ Hydrothermal Growth of Metal-Organic Framework 199 Films on Stainless Steel Fibers for Solid-Phase Microextraction of Gaseous Benzene Homologues", Anal. Chem. 2009, 81, 9771-9777.
Czaja et al., "Industrial applications of metal-organic frameworks," Chemical Society Reviews 38(5):1284-1293 (2009).
Day et al., "A New Structure Type in Polyoxoanion Chemistry: Synthesis and Structure of the V5O143-Anion", J. Am. Chem. Soc. 1989, 111, 4518-4519.
Day et al., "Synthesis and Characterization of a Soluble Oxide Inclusion Complex, [CH3CNC(V12O324-)]", J. Am. Chem. Soc. 1989, 111, 5959-5961.

(56) References Cited

OTHER PUBLICATIONS

Delgado-Friedrichs et al., "Three-Periodic Nets and Tilings: Regular and Quasiregular Nets," Acta Cryst. A59: 22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Delgado-Friedrichs et al. "What Do We Know About Three-Periodic Nets?," J. Solid State Chem. 178: 2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Demessence et al., "Strong CO2 Binding in a Water-Stable, Triazolate-Bridged Metal-Organic Framework Functionalized with Ethylenediamine", J. Am. Chem. Soc. 2009, 131, 8784-8786.
Deng et al., "Robust dynamics" Nature Chem. 2:439-443 (2010).
Deng et al., "Large-Pore Apertures in a Series of Metal-Organic Frameworks", Science, 336, 1018 (2012).
Doonan et al., "Isoreticular Metalation of Metal-Organic Frameworks," J. Am. Chem. Soc. 131:9492-9493 (2009).
Li et al. "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).
Li et al., "Porous Germanates: Synthesis, Structure and Inclusion Properties of Ge7O14.5F2-[(CH3)2NH2]3(H2O)O.86," J. Am. Chem. Soc. 120:8567-8568 (1998).
Li et al., "Transformation of Germanium Dioxide to 4-Connected Porous Germanate Net," J. Am. Chem. Soc. 10569-10570 (1998).
Li et al., "An Open-Framework Germanate with Polycubane-Like Topology," Angew. Chem. INt. Ed., 38:653-655 (1999).
Li et al., "Supertetrahedral Sulfide Crystals with Giant Cavities and Channels," Science 283:1145-1147 (1999).
Li et al., "Non-interpenetrating Indium Sulfide with a Supertetrahedral Cristobalite Framework," J. Am. Chem. Soc. 121:6096-6097 (1999).
Li et al., "Design and Synthesis of an Exceptionally Stable and Highly Porous Metal-Organic Framework," Science 402:276-279 (1999); Featured in (1) Chemical and Engineering News (Nov. 22, 1999) and (2) Science News (Nov. 20, 1999).
Li et al., "Ge2ZrO6F2 (H2DAB)H2O: A 4-Connected Microporous Material with "Bow Tie" Building Units and an Exceptional Proportion of 3-Rings," J. Am. Chem. Soc. 122:12409-12410 (2000).
Li et al., "[Cd16In64S134]44—: 31-Å Tetrahedron with a Large Cavity," Angew. Chem. Int. Ed 42:1819-1821 (2003).
Li et al., "Hydrogen Storage in Metal-Organic and Covalent-Organic Frameworks by Spillover", AlChE Journal, Jan. 2008, vol. 54, No. 1, pp. 269-279.
Li et al., "Docking in Metal-Organic Frameworks", Science, 325, 855 (2009).
Li et al., "A metal-organic framework replete with ordered donor-acceptor catenanes," Chem. Commun. 46:380-382 (2010).
Li et al., "A Catenated Strut in a Catenated Metal-Organic Framework," Angew. Chem. Int. Ed. 49:6751-6755 (2010).
Loeb, "Rotaxanes as ligands: from molecules to materials", Chem. Soc. Rev., 2007, 36, 226-235.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).
McKeown et al., "Phthalocyanine-based nanoporous network polymers", Chem. Comm., 2002, 2780-2781.
McKeown et al., "Porphyrin-based nanoporous network polymers", Chem. Comm., 2002, pp. 2782-2783.
Mendoza-Cortes et al., "Adsorption Mechanism and Uptake of Methane in Covalent Organic Frameworks: Theory and Experiment", J. Phys. Chem. A 2010, 114, 10824-10833.

Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental—Computational Investigation of Carbon Dioxide Capture in a Series of Isoreticular Zeolitic Imidazolate Frameworks," J. Am. Chem. Soc. 132:11006-11008 (2010).
Morris et al., "Framework mobility in the metal-organic framework IRMOF-3: Evidence for aromatic ring and amine rotation", Journal of Molecular Structure 1004 (2011), pp. 94-1010.
Morris et al., "Postsynthetic Modification of a Metal-Organic Framework for Stabilization of a Hemiaminal and Ammonia Uptake," Inorg. Chem. 50:6853-6855 (2011).
Morris et al., "Synthesis, Structure and Metalation of Two New Highly Porous Zirconium Metal-Organic Frameworks", Inorg. Chem. 2012, 51, pp. 6443-6445.
Morris et al., "NMR and X-ray Study Revealing the Rigidity of Zeolitic Imidazolate Frameworks", J. Phys. Chem. C 2012, 116, 13307-13312.
Moyse, Ellen, International Preliminary Report on Patentability and Written Opinion, Date of Issuance of Report: Nov. 17, 2009, International Application No. PCT/US08/006008.
Mulfort et al., "Chemical Reduction of Metal-Organic Framework as a Method to Enhance Gas Uptake and Binding", J. Am. Chem. 2007, 129, 9604-9605.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Natarajan et al., "Non-carboxylate based metal-organic frameworks (MOFs) and related aspects", Current Opinion in Solid State and Materials Science 13 (2009), 46-53.
Ni et al,. "Porous Metal-Organic Truncated Octahedron Constructed from Paddle-Wheel Squares and Terthiophene Links," J. Am. Chem. Soc. 127:12752-12753 (2005).
Nickitas-Etienne, Athina, International Preliminary Report on Patentability and Written Opinion, Date of Issuance of Report: Jan. 19, 2010, International Application No. PCT/US08/70149.
Nickitas-Etienne, Athina. International Preliminary Report on Patentability for PCT/US2008/07741. Date of issuance of this report: Mar. 30, 2010.
Nickitas-Etienne, Athina. International Preliminary Report on Patentability for PCT/US2009/068731. Date of Issuance of the Report: Jun. 21, 2011.
Nickitas-Etienne, Athina. International Preliminary Report on Patentability for PCT/US2009/068849. Date of Mailing: Jun. 30, 2011.
Niu et al., "Synthesis and structural characterization of the one dimensional polymers [Rh2(OAc)4(NCPhCN)]S, S = CH3COCH3, CH3OH, C2H5OH, C4H8O, and C6H6," Polyhedron 17(23-24):4079-89 (1998).
Ockwig et al., "Reticular Chemistry: Occurrence and Taxonomy of Nets and Grammar for the Design of Frameworks", Acc. Chem. Res. 2005, 38, 176-182.
Oisaki et al., "A Metal-Organic Framework with Covalently Bound Organometallic Complexes," J. Am. Chem. Soc. 132:9262-9264 (2010).
O'Keefe et al., "Germanate Zeolites: Contrasting the Behavior of Germanate and Silicate Structures Built from Cubic T8O20 units (T = Si or Ge)," Chem. Eur. J. 5:2796-2801 (1999).
O'Keefe et al., "Frameworks for Extended Solids: Geometrical Design Principles," J. Solid State Chem. 152:3-20 (2000).
Okeeffe et al., "Reticular Chemistry—Present and Future Prospects—Introduction," J. Solid State Chem.178:V-VI (2005).
O'Keeffe et al., "The Reticular Chemistry Structure Resource (RCSR) Database of, and Symbols for, Crystal Nets," Acc. Chem. Res. 41:1782-1789 (2008).
O'Keeffe et al., "Deconstructing the Crystal Structures of Metal-Organic Frameworks and Related Materials into Their Underlying Nets", Chemical Reviews, 112, 675-702 (2012).

(56) References Cited

OTHER PUBLICATIONS

Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.

Park et al., "Synthesis, Structure Determination, and Hydrogen Sorption Studies of New Metal-Organic Frameworks Using Triazole and Naphthalenedicarboxylic Acid", Chem. Mater. 2007, 19, 1302-1308.

Pawsey et al., "Hyperpolarized 129Xe Nuclear Magnetic Resonance Studies of Isoreticular Metal-Organic Frameworks," Phys. Chem. 111:6060-6067 (2007).

Peterson et al., "Ammonia Vapor Removal by CU3(BTC)2 and its Characterization by MAS NMR", J. Phys Chem C Nanometer Interfaces, Jul. 1, 2009: 113(31): 13906-13917.

Phan et al., "Synthesis, Structure, and Carbon Dioxide Capture Properties of Zeolitic Imidazolate Frameworks," Acc. Chem. Res 43:58-67 (2009).

Phan et al., "Metal-Organic Frameworks of Vanadium as Catalysts for Conversion of Methane to Acetic Acid," Inorg. Chem. 50:7388-7390 (2011).

Wong-Foy et al., "Exceptional H2 Saturation Uptake in Microporous Metal-Organic Frameworks", J. Am. Chem. Soc. 2006, 128, 3494-3495.

Wu et al., "Structural study of new hydrocarbon nano-crystals by energy-filtered electron diffraction," Ultramicroscopy 98 (2004) 145-150.

Yaghi et al., "Rhenium-Selenium-Chlorine Solid Phases: Cluster Excision and Core Substitution Reactions of Molecular Species", Inorg. Chem. 1992, 31, 4778-4784.

Yaghi et al., "Directed Transformation of Molecules to Solids: Synthesis of a Microporous Sulfide from Molecular Germanium Sulfide Cages", J. Am. Chem. Soc. 1994, 116, 807-808.

Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).

Yaghi et al., "Selective binding and removal of guests in a microporous metal-organic framework," Nature, Dec. 1995, pp. 703-706, vol. 378.

Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.

Yaghi et al., "Mutually Interpenetrating Sheets and Channels in the Extended Structure of [Cu(4,4'-bpy)C]", Angew. Chem. Int. Ed. Engl. 1995, 34, No. 2, pp. 207-209.

Yaghi et al., "Hydrothermal Synthesis of a Metal-Organic Framework Containing Large Rectangular Channels", J. Am. Chem. Soc., 1995, 117, 10401-10402.

Yaghi et al., "Construction of Porous Solids from Hydrogen-Bonded Metal Complexes of 1,3,5-Benzenetricarboxylic Acid", J. Am. Chem. Soc. 1996, 118, 9096-9101.

Yaghi et al., "T-Shaped Molecular Building Units in the Porous Structure of Ag(4,4'-bpy) NO3," J. Am. Chem. Soc., 1996, 118, 295-296.

Yaghi et al., "Synthesis and Structure of a Metal-Organic Solid Having the Cadmium (II) Sulfate Net," Mater. Res. Soc. Symp. Proc. 453:127, (1997).

Yaghi et al., "Selective Guest Binding by Tailored Channels in a 3-D Porous Zinc(II)-Benzenetricarboxylate Network", J. Am. Chem. Soc. 1997, 119, 2861-2868.

Yaghi et al., "Crystal Growth of Extended Solids by Nonaqueous Gel Diffusion," Chem. Mater., 1997, 9, 1074-1076.

Yaghi et al., "A Molecular Railroad with Large Pores: Synthesis and Structure of Ni(4,4'-bpy)2.5(H2O)2(ClO4)2•1.5(4,4'-bpy)2(H2O)," Inorg. Chem., 1997, 36, 4292-4293.

Yaghi et al., "Construction of a new open-framework solid from 1,3,5-cyclohexane-tricarboxylate and zinc(II) building blocks", J. Chem. Soc., Dalton Trans., 1997, pp. 2383-2384.

Yaghi et al., "Synthetic Strategies, Structure Patterns, and Emerging Properties in the Chemistry of Modular Porous Solids," Acc. Chem. Res. 31:474-484 (1998).

Yaghi et al., "Transformation of Germanium Dioxide to 4-Connected Porous Germanate Net," J. Am. Chem. Soc., 20:10569-10570 (1998).

Yaghi et al., "Design of Solids from Molecular Building Blocks: Golden Opportunities for Solid State Chemistry," J. Solid State Chem. 152, 1-2 (2000).

Yaghi et al., "Reticular Synthesis and the Design of New Materials," Nature 423:705-714 (2003).

Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.

Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.

Yaghi et al., "Metal-Organic Frameworks: A Tale of Two Entanglements," Nature materials 6:92-93 (2007).

Yaghi et al., "Reticular Chemistry and Metal-Organic Frameworks for Clean Energy," MRS Bulletin 34:682-690 (2009).

Yang et al., "Four Novel Three-Dimensional Triazole-Based Zinc(II) Metal-Organic Frameworks Controlled by the Spacers of Dicarboxylate Ligands: Hydrothermal Synthesis, Crystal Structure, and Luminescent Properties", Crystal Growth & Design, 2007, vol. 7, No. 10, 2009-2015.

Young, Lee W., International Search Report and Written Opinion, Date of Mailing of Report: May 7, 2008, International Application No. PCT/US08/51859.

Young, Lee W., "International search Report and Written Opinion," PCT/US08/06008, United States Patent & Trademark Office, Aug. 20, 2008.

Young, Lee W., International Search Report and Written Opinion, Date of Mailing: Dec. 2, 2008, International Application No. PCT/US08/77741.

Young, Lee W., International Search Report and Written Opinion, Date of Mailing: Jan. 12, 2009, International Application No. PCT/US08/70149.

Young, Jung Doo. International Search Report for PCT/US2010/050170. Date of Mailing: Jun. 8, 2011.

Young, Jung Doo, International Search Report for PCT/US2011/053423, Date of Mailing: Jul. 23, 2012.

Zhang et al., "Crystal engineering of binary metal imidazolate and triazolate frameworks", Chem. Comm., 2006, 1689-1699.

Zhang et al., "Exceptional Framework Flexibility and Sorption Behavior of a Multifunctional Porous Cuprous Triazolate Framework", J. Am. Chem. Soc., 2008, 130, 6010-6017.

Zhang et al., "Docking in Metal-Organic Frameworks," Science 325:855-859 (2009).

Zhang et al., "Syntheses, Structures, and Porous/Luminescent Properties of Silver 3-Alkyl-1,2,4-Triazolate Frameworks with Rare 3-Connected Topologies," Crystal Growth & Design, 2011, vol. 11, 796-802.

Zhao et al., "Rigid-Strut-Containing Crown Ethers and [2]Catenanes for Incorporation into Metal-Organic Frameworks," Chem. Eur. J. 15:13356-13380 (2009).

Zhao, Office Action in Chinese Patent Application No. 20088031572, Aug. 5, 2011.

Zhofu et al., "A Nearly Planar Water Sheet Sandwiched between Strontium-Imidazolium Carboxylate Coordination Polymers," Inorg. Chem. 44:5200-5202 (2005).

Zhou et al., "Hydrothermal syntheses and structures of three novel coordination polymers assembled for 1,2,3-triazolate ligands", CrystEngComm, 2009, 11, 1964-1970.

Zhou et al., "Introduction to Metal-Organic Frameworks", Chem. Rev., 2012, 12, 673-674.

Zhu et al., "Isomeric Zinc(II) Triazolate Frameworks with 3-Connected Networks: Syntheses, Structures, and Sorption Properties", Inorg. Chem. 2009, 48, 3882-3889.

Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.

(56) References Cited

OTHER PUBLICATIONS

Banerjee et al., "High-Throughput Synthesis of Zeiolitic Imidazolate Frameworks and Application to CO2 Capture," Science, 2008, pp. 939-943, vol. 319.
Burrows et al., "Post-Synthetic Modivication fo Tagged Metal-Organic Frameworks," Angew. Chem Int'l., 2008, pp. 8482-8486, vol. 47.
Deng et al., "Multiple Functional Groups of Varying Ratios in Metal-Organic Frameworks," Science, 2010, pp. 846-850, vol. 327.
Isaeva et al., "Metal-Organic Frameworks—New Materials for Hydrogen Storage," Russian J. of General Chem., 2007, pp. 721-739, vol. 77, No. 4.
Koh et al., "A Crystalline Mesoporous Coordination Copolymer with High Microporosity," Angew Chem Int'l, 2008, pp. 677-680, vol. 47.
Kim, Su Mi, International Search Report and Written Opinion, PCT/US2010/039154, Korean Intellectual Property Office, Feb. 23, 2011.

COMPLEX MIXED LIGAND OPEN FRAMEWORK MATERIALS

CROSS REFERENCE TO RELATED APPLICATIONS

This application is a U.S. National Stage Application filed under 35 U.S.C. §371 based upon International Application No. PCT/US10/39154, filed Jun. 18, 2010, which application claims priority under 35 U.S.C. §119 from Provisional Application Serial Nos. 61/218,879, filed Jun. 19, 2009 and 61/246,004, filed Sep. 25, 2009, the disclosures of which are incorporated herein by reference.

STATEMENT AS TO FEDERALLY SPONSORED RESEARCH

This invention was made with Government support of Grant No. W911NF-06-1-0405: P00001 awarded by the Department of Defense. The U.S. government has certain rights in this invention.

TECHNICAL FIELD

The disclosure provides organic frameworks for gas separation, storage, for use as sensors comprising mixed ligands.

BACKGROUND

Crystalline extended structures tend to be 'simple' in that they are constructed from a small number of distinct building units.

SUMMARY

The structures of extended crystalline solids are fundamentally 'simple' in that they are typically built from small number of distinct building units. This is certainly the case in metal-organic frameworks (MOFs), where they are usually constructed from one kind of link, functionality and metal ion unit.

The disclosure provides metal organic frameworks comprising a plurality of different functional groups on a linking moiety or on at least two different linking moieties. The porous organic framework is multi-variant in that variations of the pore functionality can be readily modified by incorporating at least two different functional groups into an organic framework. In one embodiment, the linking moiety substructure is homogenous, however, a side-group on the linking moiety is varied.

The disclosure provides a porous organic framework comprising a plurality of linking moieties with different functional groups whose orientation, number, relative position and ratio along the backbone are controllable by virtue of the unchanged size of the linking moiety and the unaltered connectivity of the backbone and wherein the functional groups modify the chemical and physical properties of a pore in the framework. In one embodiment, the organic framework is constructed from n different organic links, wherein n≥2. In another embodiment, the functional groups are along a core comprising a metal-oxide and phenyl units. In yet another embodiment, the organic framework comprises repeating units of metal-oxide joints and organic linking moieties, and a plurality of functional groups which are covalently bound to the linking moieties, wherein the functional groups are heterogeneous and/or wherein the functional groups are differently spaced along a link. In one embodiment, the organic framework comprises a MOF topology substantially identical to a MOF-5 framework. In another embodiment, the framework comprises a metal selected from the group consisting of: $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof, along with corresponding metal salt counter-anions. In yet another embodiment, the linking moiety has a general structure selected from the group consisting of

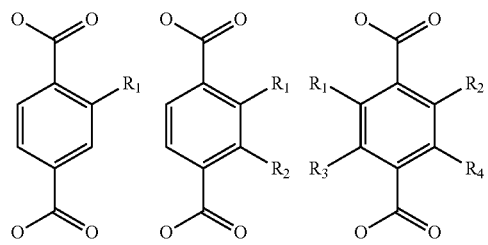

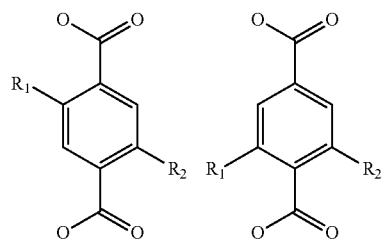

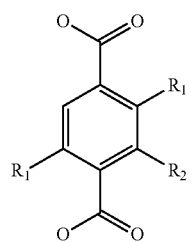

wherein $R_1$-$R_4$ are selected from the group consisting of —H, —$NH_2$, —BR, —Cl, —$NO_2$, —$CH_3$, —$OCH_2R_5$, and —O—$CH_2R_6$, wherein $R_5$ is an alkyl or alkene of from about 1-5 carbons, and $R_6$ is an aryl or substitute aryl, or wherein $R_1$-$R_2$ when adjacent can form a ring. In a further embodiment, the linking moiety comprises a member selected from the group consisting of:

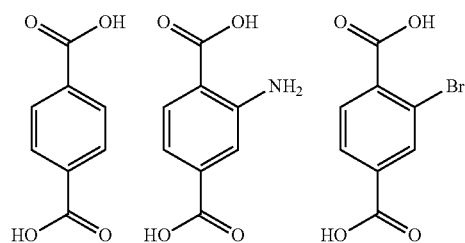

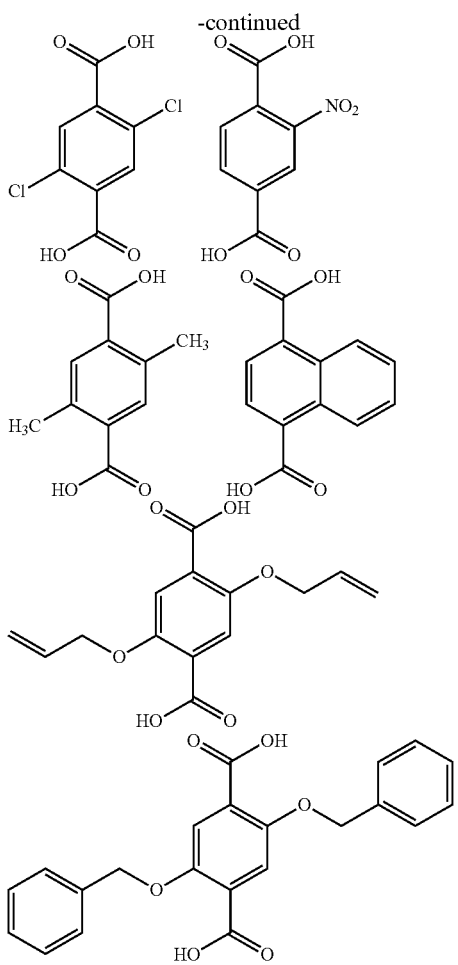

In yet another embodiment, the organic framework comprises a first linking moiety of the plurality of linking moieties comprising a first functional group and a second linking moiety of the plurality of linking moieties comprising a second functional group wherein the second functional group can undergo post-synthesis reaction with a post-reactant group to further functionalize the framework. In yet another embodiment the mvMOF comprises improved gas sorption capacity compared to a framework having the same topology but homogenous linking moieties.

The disclosure also provides a method of making a mvMOF comprising mixing a plurality of chemically functionalized linking moieties with a metal ion or metal nitrate, wherein the linking moieties are at a desired ratio to incorporate the desired ratio of a particular combination of linking moieties into the organic framework, purifying the crystals and removing the solvent. In one specific embodiment, the method comprises mixing a plurality of chemically functionalized linking moieties at desired ratios to incorporate the desired ratio of a particular combination of linking moieties into an organic framework comprising benzene dicarboxylic acids with zinc nitrate in DEF/DMF.

The disclosure also provides a gas separation device comprising an mvMOF. The disclosure also provides a gas storage device comprising an mvMOF.

The disclosure demonstrates in a specific embodiment a strategy for making more complex MOFs by using links of multiple functionalities to produce multivariate (MTV) structures. 1,4-benzenedicarboxylate (BDC, A) and its functionalized derivatives, —$NH_2$, —Br, —$(Cl)_2$, —$NO_2$, —$(CH_3)_2$, —$C_4H_4$, —$(C_3H_5O)_2$, and —$(C_7H_7O)_2$ (B-I, respectively), were used to build eighteen mvMOFs, each of which has the cubic MOF-5 type crystal structure and contains up to eight different functionalities (two: mvMOF-5-AB, -AC, -AD, -AE, -AF, -AG, -AH, -AI, -EI; three: mvMOF-5-ABC, -AHI, -EHI; four: mvMOF-5-ABCD, -ACEF; Five: mvMOF-5-ABCHI; six: mvMOF-5-ABCGHI; seven: mvMOF-5-AB-CEGHI; eight: mvMOF-5-ABCEFGHI). Single crystal diffraction studies of a typical member of this series (mvMOF-5-ACEF) confirm that the MOF backbone (metal-oxide and phenyl units) is ordered and the functionalities are unavoidably disordered, which rules out the possibility of these MOFs being solid solutions. Nuclear magnetic resonance spectroscopy was used to determine the presence of each functional group, their identity and ratio within the structure of each member of the mvMOF series. These measurements were also performed on several crystals selected from the solid products to confirm their bulk homogeneity, and on segments of single crystals to confirm the existence of an identical link ratio throughout the crystal. Although the latter observation may argue for a random distribution of functionalities within the crystal, it is probably that they are more likely to be arranged in a specific sequence because of link-link interactions which would inevitably create bias for a specific link at a specific unhindered location. This is supported by the observed relatively higher ratio of the least hindered link (A) in most of the respective mvMOFs. The 'complex' arrangement of functional groups within the pores results in up to 400% enhancement in the selectivity of mvMOF-5-EHI for CO2 over CO compared to that of the same link counterpart (MOF-5).

The disclosure provide a complex self-assembled open framework material constructed from n (where n≥2) different organic links. This disclosure encompasses all open framework materials that are constructed from organic links bridged by multidentate organic or inorganic cores. Including all classes of open framework materials; covalent organic frameworks (COFs), zeolitic imidazolate frameworks (ZIFs) and metal organic frameworks (MOFs) and all possible resulting net topologies as described within the reticular chemistry structure resource (http://rcsr.anu.edu.au/ By utilizing greater than 2 links in the framework, complex architectures can be synthesized engendering multifarious materials. Such materials will have a variety of uses in application such as gas storage and separation and catalysis.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
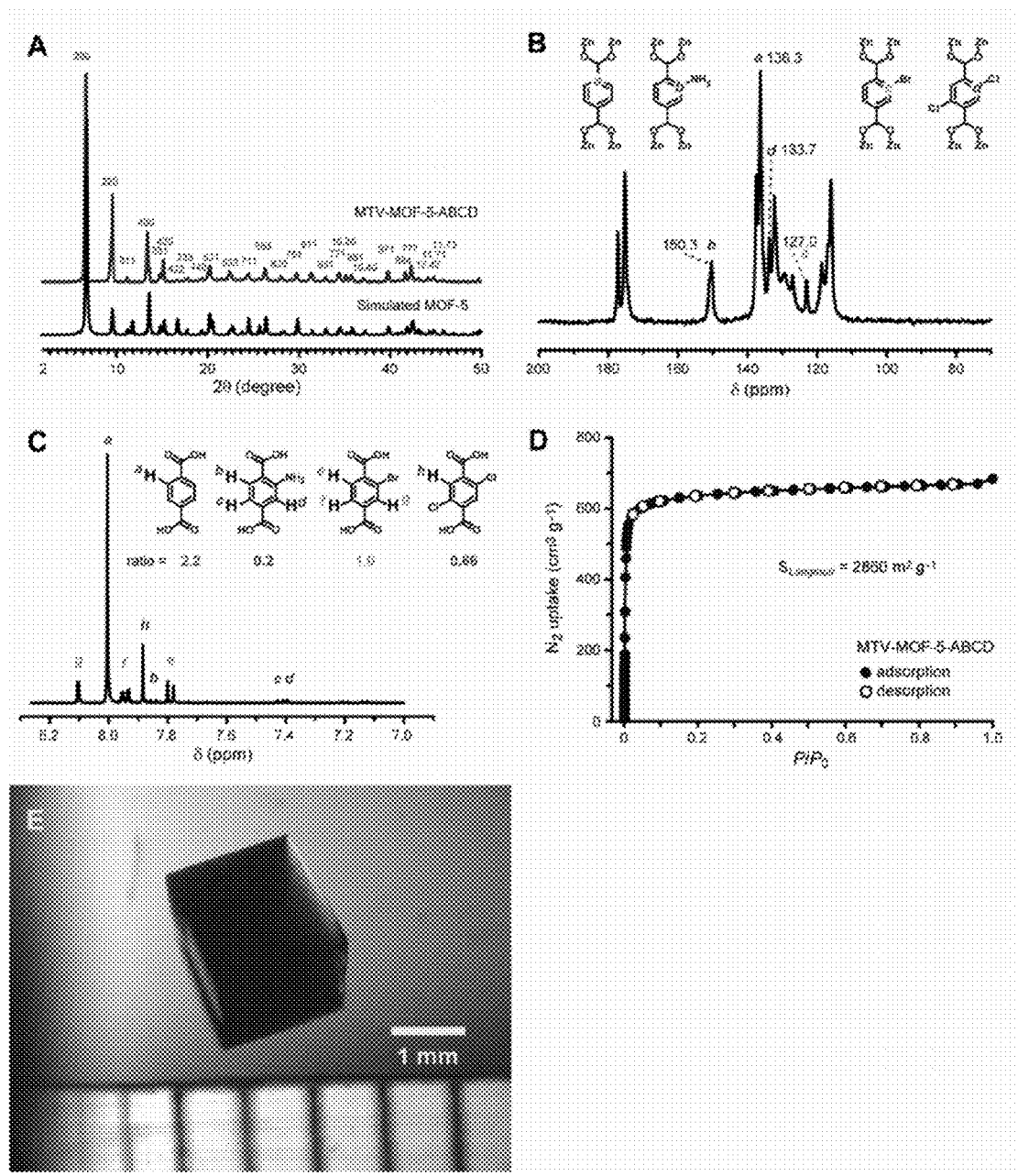
FIG. 1A-E shows a typical analysis performed on mvMOFs shown here for samples of mvMOF-5-ABCD. (A) X-ray diffraction patterns of the crystalline powder compared to the simulated one for MOF-5. (B)$^{13}$C CP/MAS NMR spectrum showing unique resonance for each link. (C) Solution $^1$H NMR spectrum used to determine the ratio of links. (D) $N_2$ adsorption isotherm at 77 K with adsorption and desorption points represented by closed circles and open circles, respectively. (E) A large crystal from which segments were analyzed for the ratio of links and found to be identical throughout.

As used herein and in the appended claims, the singular forms "a," "and," and "the" include plural referents unless the context clearly dictates otherwise. Thus, for example, reference to "a framework" includes a plurality of such frameworks and reference to "the metal" includes reference to one or more metals and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Crystalline extended structures tend to be 'simple' in that they are constructed from a small number of distinct building units. Increasing the number and diversity of such units provide the opportunity to improve the properties of the crystalline structures. Indeed one can imagine developing artificial materials wherein a specific arrangement of a large number of different building units codes for a specific function or leads to a new phenomena. To date, crystalline materials of this kind of 'complexity' do not exist because their synthesis generally yields either mixed phases, rather than a single phase of mixed units, or amorphous materials. Even in the well-established chemistry of block copolymers, slight changes in the functionality of the side chains lead to large undesirable changes in the polymer structure or to its phase separation; thus precluding expression of control over their structure and complexity.

Having developed methods of building rigid, ordered metal-organic frameworks (MOFs) in which metal-oxide units are linked by organic units, the disclosure demonstrates that the inherent regularity of the MOF backbone could be useful in achieving controlled complexity into MOFs. The disclosure demonstrates a strategy to introduce links with different functional groups whose orientation, number, relative position and ratio along the backbone are controllable by virtue of the unchanged size of the link and the unaltered connectivity of the backbone. Such a MOF can be viewed as having a primary structure comprised of the 'simple' repeating pattern of metal-oxide and organic link units, and a 'complex' secondary structure formed by widely varied arrangements of functional groups which are covalently bound to the links. In this way, each of the pores within the MOF would have an array of mixed functionalities pointing to their center. Accordingly, the sequence of such functionalities and the frequency with which certain of them appear in the sequence will endow the pores with a new level of complexity which far exceeds any held by that of the original single-link MOFs; an aspect that allows fine-tuning of the pore environment with favorable implications on properties.

The disclosure thus demonstrates that by combining the inherent rigidity of metal-organic frameworks (MOFs) and the functional flexibility of polymers, one can overcome these challenges and create a large number of single phase materials each of which has multi-variate (MTV) functionalities.

Figure 55:
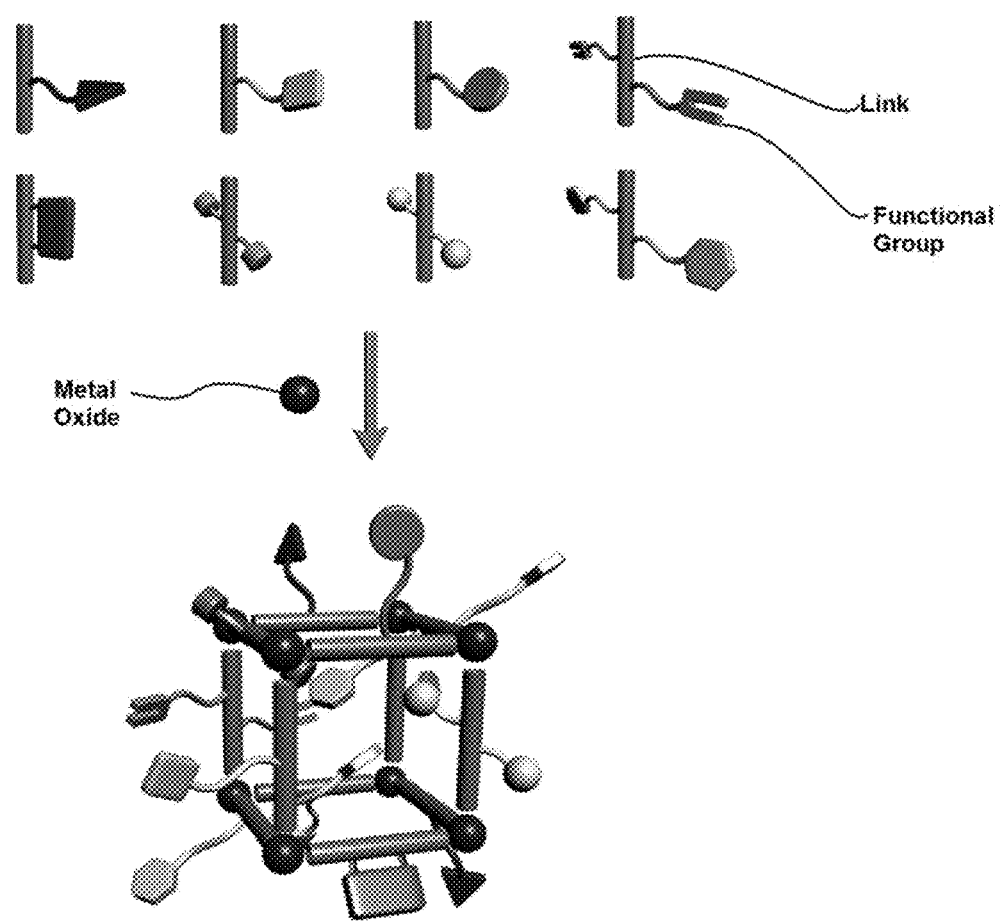
FIG. 55 depicts a cartoon showing variations for links making up mvMOFs.

The disclosure also provides methods of making multivariate metal organic frameworks (mvMOFs) by assembling their structures from links with different functional groups whose orientation, number, relative position and ratio, along the backbone (metal-oxide and phenyl units), can be controlled by virtue of the unchanged length of the link and its unaltered connectivity (see FIG. 55). Accordingly, the sequence of such functionalities and the frequency with which certain functional groups appear in the sequence will endow the pores with a new level of complexity which far exceeds any held by that of the original same-link MOFs—an aspect that will allow fine-tuning of the pore environment with favorable implications on properties.

The disclosure describes a general method for producing crystalline MOF materials which combine sets of two, three, four, five, six, seven, eight, nine, ten, eleven or twelve links of different functional groups, each of which is incorporated into a single structure where the ratio of links is controlled, and the material can be produced with bulk purity. The disclosure demonstrates the isolation of multi-variant MOFs as a single phase. The porosity of mvMOFs is diverse and show that multi-varied links can introduce various functionalities. For example, varied links that can be introduced into a MOF structure include, but are not limited to, $NO_2$-BDC and $(Cl)_2$-BDC, into the MOF-5 type structure (mvMOF-5-AD and -AE), that otherwise do not form this structure when used alone. The disclosure also demonstrates that members of this series (e.g, mvMOF-5-AHI and -EHI) show that the 'whole is better than the sum of its parts' as evidenced by the significant enhancement of gas adsorption and separation properties of the multi-varied link MOFs compared to their simple same-link analogues.

A multi-variant metal organic framework (mvMOF) refers to a MOF structure comprising at least 2, 3, 4, 5, 6, 7, 8, 9, 10, 11 or 12 different linking moieties having varied functionalities. The mvMOF comprises a metal conjugated to a linking moiety via a linking cluster. The substructure of the linking moiety comprises different functionality attributable by varying side-groups on the substructure. For example, an mvMOF comprises in cuboidal structure comprises at its corners metals (e.g., 4 metal atoms), each metal atom is conjugated to 3 linking clusters, each linking cluster conjugated to a linking moiety substructure. Accordingly, a cuboidal structure comprises 12 linking moieties. Variation in one or more side groups on the linking moiety generates varied functionality of the resulting cuboidal structure. Taken to the size of a MOF framework, the variation in the framework provides improved and diverse functions for gas storage, separation and purification.

As used herein, a "core" refers to a repeating unit or units found in a framework. Such a framework can comprise a homogenous repeating core or a heterogeneous repeating core structure. A core comprises a transition metal or cluster of transitions metals and a linking moiety. A plurality of cores linked together defines a framework.

The term "cluster" refers to identifiable associations of 2 or more atoms. Such associations are typically established by some type of bond—-ionic, covalent, Van der Waal, and the like.

A "linking cluster" refers to one or more reactive species capable of condensation comprising an atom capable of forming a bond between a linking moiety substructure and a metal group or between a linking moiety and another linking moiety. Examples of such species are selected from the group consisting of a boron, oxygen, carbon, nitrogen, and phosphorous atom. In some embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Typically linking clusters for binding metals in the generation of MOFs contain carboxylic acid functional groups.

The disclosure includes cycloalkyl or aryl substructures that comprise 1 to 5 rings that consist either of all carbon or a mixture of carbon, with nitrogen, oxygen, sulfur, boron, phosphorous, silicon and aluminum atoms making up the ring.

The term "covalent organic polyhedra" refers to a non-extended covalent organic network. Polymerization in such polyhedra does not occur usually because of the presence of capping ligands that inhibit polymerization. Covalent organic polyhedra are covalent organic networks that comprise a plurality of linking moieties linking together multidentate cores such that the spatial structure of the network is a polyhedron. Typically, the polyhedra of this variation are 2 or 3 dimensional structures.

A "linking moiety" refers to a mono-dentate or polydentate compound that bind a transition metal or a plurality of transition metals, respectively. Generally a linking moiety comprises a substructure comprising an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and a linking cluster at one or more positions of the substructure to facilitate condensation with a metal. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring.

Typically the linking moiety will comprise a substructure having one or more carboxylic acid linking clusters covalently attached. The substructure can be functionalized with reactive side groups.

As used herein, a line in a chemical formula with an atom on one end and nothing on the other end means that the formula refers to a chemical fragment that is bonded to another entity on the end without an atom attached. Sometimes for emphasis, a wavy line will intersect the line.

In one aspect, the linking moiety substructure is selected from any of the following:

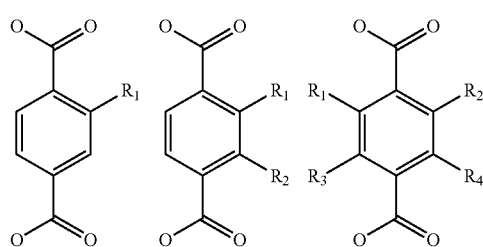

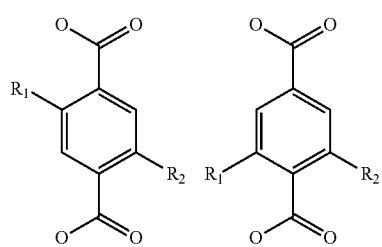

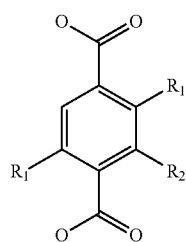

wherein $R_1$-$R_4$ are selected from the group consisting of —H, —NH$_2$, —BR, —Cl, —NO$_2$, —CH$_3$, —OCH$_2$R$_5$, and —O—CH$_2$R$_6$, wherein R$_5$ is an alkyl or alkene of from about 1-5 carbons, and R$_6$ is an aryl or substitute aryl, or wherein $R_1$-$R_2$ when adjacent can form a ring. In one embodiment, the linking ligand comprises a member selected from the group consisting of:

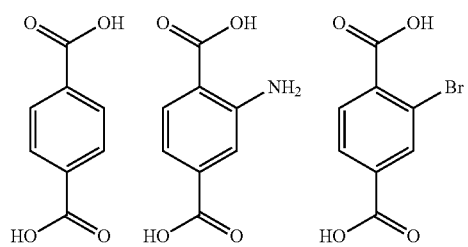

-continued

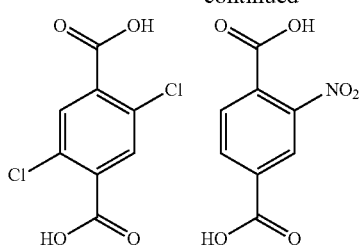

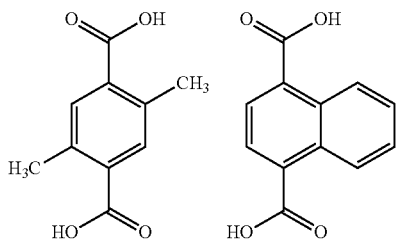

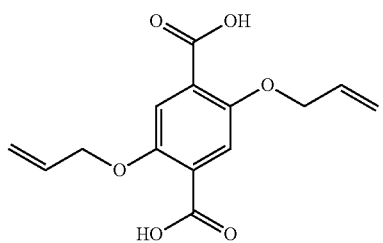

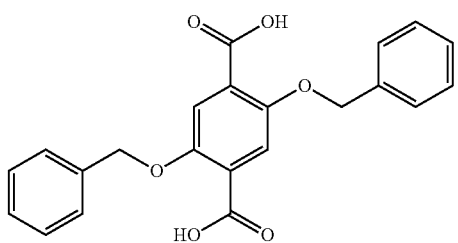

It is further contemplated that a mvMOF of the disclosure may be generated by first utilizing a plurality of linking moieties having different functional groups, wherein at least one functional group may be post-synthesis modified with a reacting group. In other words at least one linking moiety comprises a function group that may be post-synthesized reacted with a post framework reactant to further increase the diversity of the functional groups in the organic framework.

In yet another embodiment, the linking moiety can have a general structure as set forth below:

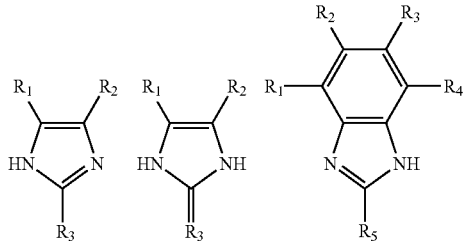

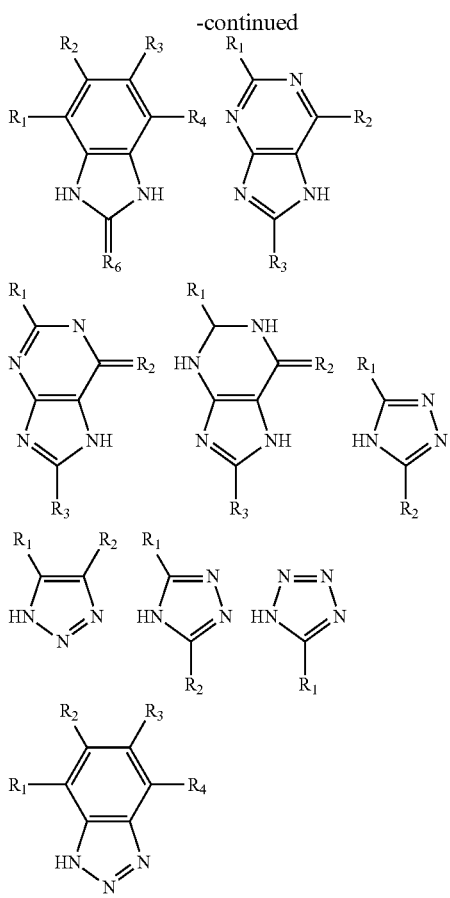

wherein $R_1$-$R_5$ is H, $NH_2$, COOH, CN, $NO_2$, F, Cl, Br, I, S, O, SH, $SO_3H$, $PO_3H_2$, OH, CHO, $CS_2H$, $SO_3H$, $Si(OH)_3$, $Ge(OH)_3$, $Sn(OH)_3$, $Si(SH)_4$, $Ge(SH)_4$, $PO_3H$, $AsO_3H$, $AsO_4H$, $P(SH)_3$, $As(SH)_3$, $CH(RSH)_2$, $C(RSH)_3$, CHN $(RNH_2)_2$, $C(RNH_2)_3$, $CH(ROH)_2$, $C(ROH)_3$, $CH(RCN)_2$, $C(RCN)_3$,

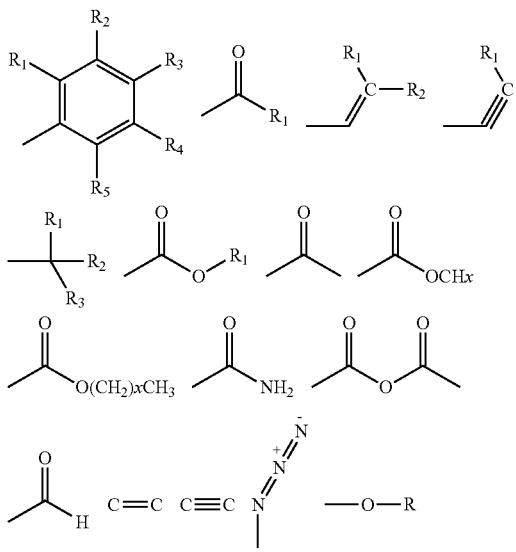

wherein X=1, 2, or 3.

All the aforementioned linking moieties that possess appropriate reactive functionalities can be chemically transformed by a suitable reactant post framework synthesis to add further functionalities to the pores. By modifying the organic links within the framework post-synthetically, access to functional groups that were previously inaccessible or accessible only through great difficulty and/or cost is possible and facile. Post framework reactants include all known organic transformations and their respective reactants; rings of 1-20 carbons with functional groups including atoms such as N, S, O. All metals that may chelate to and added functional group or a combination of previously existing and newly added functional groups. All reactions that result in tethering an organometallic complex to the framework for use, for example, as a heterogeneous catalysts. Some examples of post framework reactants include:

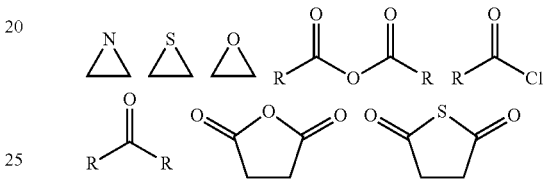

wherein R=H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones and aldehydes), halogen, nitro, amino, cyano, boron-containing groups, phosphorus-containing groups, carboxylic acids or esters.

In addition, metal and metal containing compounds that may chelate to and add functional groups or a combination of previously existing and newly added functional groups are also useful. Reactions that result in the tethering of organometallic complexes to the framework for use as, for example, a heterogeneous catalyst can be used. Examples of post framework reactants include, but are not limited to, heterocyclic compounds.

In one embodiment, the post framework reactant can be a saturated or unsaturated heterocycle. The term "heterocycle" used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings that share two atoms therebetween. A heterocycle may have aromatic character or may not have aromatic character. The terms "heterocyclic group", "heterocyclic moiety", "heterocyclic", or "heterocyclo" used alone or as a suffix or prefix, refers to a radical derived from a heterocycle by removing one or more hydrogens therefrom. The term "heterocyclyl" used alone or as a suffix or prefix, refers a monovalent radical derived from a heterocycle by removing one hydrogen therefrom. The term "heteroaryl" used alone or as a suffix or prefix, refers to a heterocyclyl having aromatic character. A heterocycle includes, for example, a monocyclic heterocycle such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, a heterocycle includes aromatic heterocycles (heteroaryl groups), for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

Metal ions that can be used in the synthesis of frameworks of the disclosure include $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $CO^{3+}$, $CO^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof, along with corresponding metal salt counter-anions.

The disclosure also provides a method of making a mvMOF of the disclosure. The methods comprises mixing a plurality of chemically functionalized linking moieties at desired ratios to incorporate the desired ratio of a particular combination of linking moieties into an organic framework with a metal ion or metal-nitrate in an appropriate buffer. The resultant crystalline material is then purified and the solvent removed. In one embodiment, the method comprises mixing a plurality of chemically functionalized linking moieties at desired ratios to incorporate the desired ratio of a particular combination of linking moieties into an organic framework comprising benzene dicarboxylic acids with zinc nitrate in DEF/DMF at 85-100° C. for 24-48 h. The resultant crystalline material is then immersed in DMF for 24 h and then sequentially in chloroform for three 24 h periods. Finally, this porous material is activated by removing the solvent under vacuum for 24 h at room temperature or heat up to 120° C.

The preparation of the frameworks of the disclosure can be carried out in either an aqueous or non-aqueous system. The solvent may be polar or non-polar as the case may be. The solvent can comprise the templating agent or the optional ligand containing a monodentate functional group. Examples of non-aqueous solvents include n-alkanes, such as pentane, hexane, benzene, toluene, xylene, chlorobenzene, nitrobenzene, cyanobenzene, aniline, naphthalene, naphthas, n-alcohols such as methanol, ethanol, n-propanol, isopropanol, acetone, 1,3,-dichloroethane, methylene chloride, chloroform, carbon tetrachloride, tetrahydrofuran, dimethylformamide, dimethylsulfoxide, N-methylpyrollidone, dimethylacetamide, diethylformamide, thiophene, pyridine, ethanolamine, triethylamine, ethlenediamine, and the like. Those skilled in the art will be readily able to determine an appropriate solvent based on the starting reactants and the choice of solvent is not believed to be crucial in obtaining the materials of the disclosure.

Templating agents can be used in the methods of the disclosure. Templating agents employed in the disclosure are added to the reaction mixture for the purpose of occupying the pores in the resulting crystalline base frameworks. In some variations of the disclosure, space-filling agents, adsorbed chemical species and guest species increase the surface area of the metal-organic framework. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

Crystallization can be carried out by leaving the solution at room temperature or in isothermal oven for up to 300° C.; adding a diluted base to the solution to initiate the crystallization; diffusing a diluted base into the solution to initiate the crystallization; and/or transferring the solution to a closed vessel and heating to a predetermined temperature.

Also provided are devices for the sorptive uptake of a chemical species. The device includes a sorbent comprising a framework provided herein or obtained by the methods of the disclosure. The uptake can be reversible or non-reversible.

In some embodiments, the sorbent is included in discrete sorptive particles. The sorptive particles may be embedded into or fixed to a solid liquid- and/or gas-permeable three-dimensional support. In some embodiments, the sorptive particles have pores for the reversible uptake or storage of liquids or gases and wherein the sorptive particles can reversibly adsorb or absorb the liquid or gas.

In some embodiments, a device provided herein comprises a storage unit for the storage of chemical species such as ammonia, carbon dioxide, carbon monoxide, hydrogen, amines, methane, oxygen, argon, nitrogen, argon, organic dyes, polycyclic organic molecules, and combinations thereof.

Also provided are methods for the sorptive uptake of a chemical species. The method includes contacting the chemical species with a sorbent that comprises a framework provided herein. The uptake of the chemical species may include storage of the chemical species. In some aspects, the chemical species is stored under conditions suitable for use as an energy source.

Natural gas is an important fuel gas and it is used extensively as a basic raw material in the petrochemical and other chemical process industries. The composition of natural gas varies widely from field to field. Many natural gas reservoirs contain relatively low percentages of hydrocarbons (less than 40%, for example) and high percentages of acid gases, principally carbon dioxide, but also hydrogen sulfide, carbonyl sulfide, carbon disulfide and various mercaptans. Removal of acid gases from natural gas produced in remote locations is desirable to provide conditioned or sweet, dry natural gas either for delivery to a pipeline, natural gas liquids recovery, helium recovery, conversion to liquefied natural gas (LNG), or for subsequent nitrogen rejection. $CO_2$ is corrosive in the presence of water, and it can form dry ice, hydrates and can cause freeze-up problems in pipelines and in cryogenic equipment often used in processing natural gas. Also, by not contributing to the heating value, $CO_2$ merely adds to the cost of gas transmission.

An important aspect of any natural gas treating process is economics. Natural gas is typically treated in high volumes, making even slight differences in capital and operating costs of the treating unit significant factors in the selection of process technology. Some natural gas resources are now uneconomical to produce because of processing costs. There is a continuing need for improved natural gas treating processes that have high reliability and represent simplicity of operation.

In addition, removal of carbon dioxide from the flue exhaust of power plants, currently a major source of anthropogenic carbon dioxide, is commonly accomplished by chilling and pressurizing the exhaust or by passing the fumes through a fluidized bed of aqueous amine solution, both of which are costly and inefficient. Other methods based on chemisorption of carbon dioxide on oxide surfaces or adsorption within porous silicates, carbon, and membranes have been pursued as means for carbon dioxide uptake. However, in order for an effective adsorption medium to have long term viability in carbon dioxide removal it should combine two features: (i) a periodic structure for which carbon dioxide uptake and release is fully reversible, and (ii) a flexibility with which chemical functionalization and molecular level fine-tuning can be achieved for optimized uptake capacities.

A number of processes for the recovery or removal of carbon dioxide from gas steams have been proposed and practiced on a commercial scale. The processes vary widely, but generally involve some form of solvent absorption, adsorption on a porous adsorbent, distillation, or diffusion through a semipermeable membrane.

The following examples are intended to illustrate but not limit the disclosure. While they are typical of those that might be used, other procedures known to those skilled in the art may alternatively be used.

EXAMPLES

The following examples are exemplary only and are not intended to limit the diversity of the MOF structures that may be modified to include various ligands and functional groups. In one embodiment, the cubic MOF-5 structure was used and combined with the acid form of 1,4-benzenedicarboxylate (BDC), $NH_2$-BDC, Br-BDC, $(Cl)_2$-BDC, $NO_2$-BDC, $(CH_3)_2$-BDC, $C_4H_4$-BDC, $(C_3H_5O)_2$-BDC, and $(C_7H_7O)_2$-BDC links (FIG. 56 —A-I, respectively) to form the corresponding sets of eighteen mvMOFs each having two or more different functionalities (two: mvMOF-5-AB, -AC, -AD, -AE, -AF, -AG, -AH, -AI, -EI; three: mvMOF-5-ABC, -AHI, -EHI; four: mvMOF-5-ABCD, -ACEF; Five: mvMOF-5-ABCHI; six: mvMOF-5-ABCGHI; seven: mvMOF-5-AB-CEGHI; eight: mvMOF-5-ABCEFGHI, FIG. 56). The disclosure demonstrates the isolation as single phases, the structure of MOF-5 backbone, and their porosity, and show that this multi-varied link synthetic strategy is useful in introducing functionalities, such as $NO_2$-BDC and $(Cl)_2$-BDC, into the MOF-5 type structure (mvMOF-5-AD and -AE), that otherwise do not form this structure when used alone. The data also demonstrate that members of this series (mvMOF-5-AHI and -EHI) show that the 'whole is better than the sum of its parts' as evidenced by the significant enhancement of gas adsorption and separation properties of the multi-varied link MOFs compared to their simple same-link analogues.

Crystals of mvMOFs were obtained by adding $Zn(NO_3)_2 \cdot 4H_2O$ to a N,N-dimethylformamide (DMF) solution mixture of the acid form of the selected organic links under conditions previously used in the synthesis of MOF-5. All the compounds were characterized by powder X-ray diffraction (PXRD), $^{13}C$ cross polarization magic angle spinning (CP/MAS) NMR, $^1H$ NMR on acid-digested solutions of their crystals, and thermogravimetric analysis (TGA), to assess their crystallinity, link composition, link ratio, and thermal stability, respectively. The porosity of a subset of these compounds (all containing two, three, or four different links, and mvMOF-5-ABCEFGHI) was evaluated by nitrogen gas adsorption measurements. Although the complete characterization procedure and the data acquired on all the compounds was performed, the particulars of mvMOF-5-ABCD is provided as an illustrative example.

Figure 56:
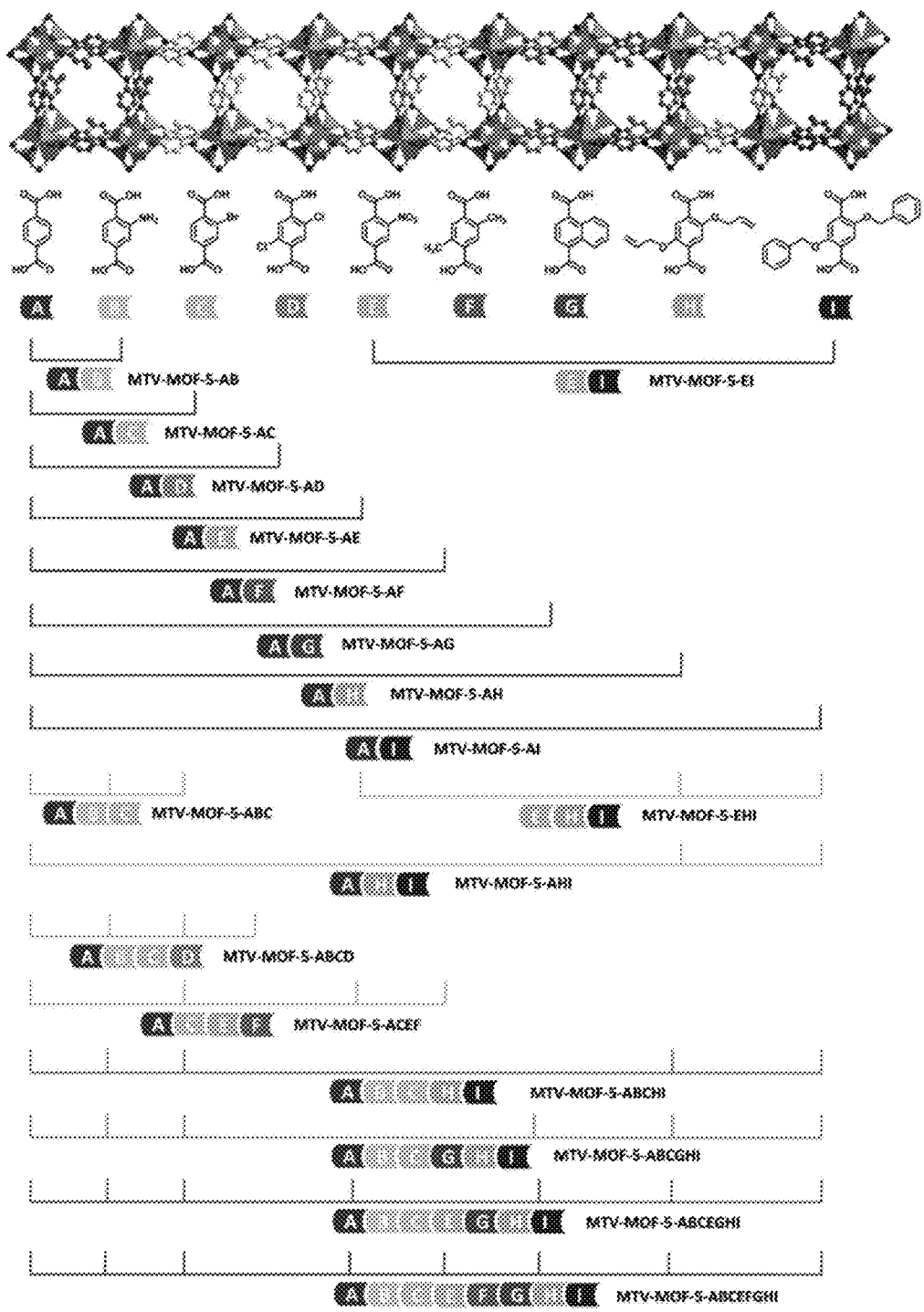
FIG. 56 demonstrates multi-layered links used to generated mvMOFs as well as examples of mvMOFs.

The compound was synthesized from equimolar amounts of link A, B, C and D (as set forth in FIG. 56). Its high crystallinity was evident from the PXRD pattern of the as-synthesized samples which gave sharp diffraction lines matching those of the parent MOF-5 structure (FIG. 1A). In order to determine the ratio of the four types of link in mvMOF-5-ABCD, the sample was evacuated by heating at 50° C. under vacuum (10 mTorr) for 24 hours to remove any guest solvent molecules from the pores that were occluded during synthesis. TGA performed on this sample showed no weight loss up to 400° C., confirming that all guest molecules were removed from the pores and that the evacuated framework is thermally stable.

$^{13}$C CP/MAS NMR spectra of evacuated samples of mvMOF-5-ABCD showed resonances at 150.3, 127.0, 133.7 and 136.3 ppm which are characteristic of the unique carbon atoms of $NH_2$-BDC, Br-BDC, $(Cl)_2$-BDC and BDC links, respectively (FIG. 1B). These spectra clearly indicate their presence in the MOF backbone. Additionally, the same experiment was performed on a mixture of the constituent free links of mvMOF-5-ABCD, where a distinct shift of 2 ppm was observed between the carbonyl carbons of the free links and those of the links that are incorporated into the framework, thus confirming that no unbound organic link is present within the MOF crystals. Similar analyses on all the remaining mvMOFs led to the same conclusion.

Figure 28:
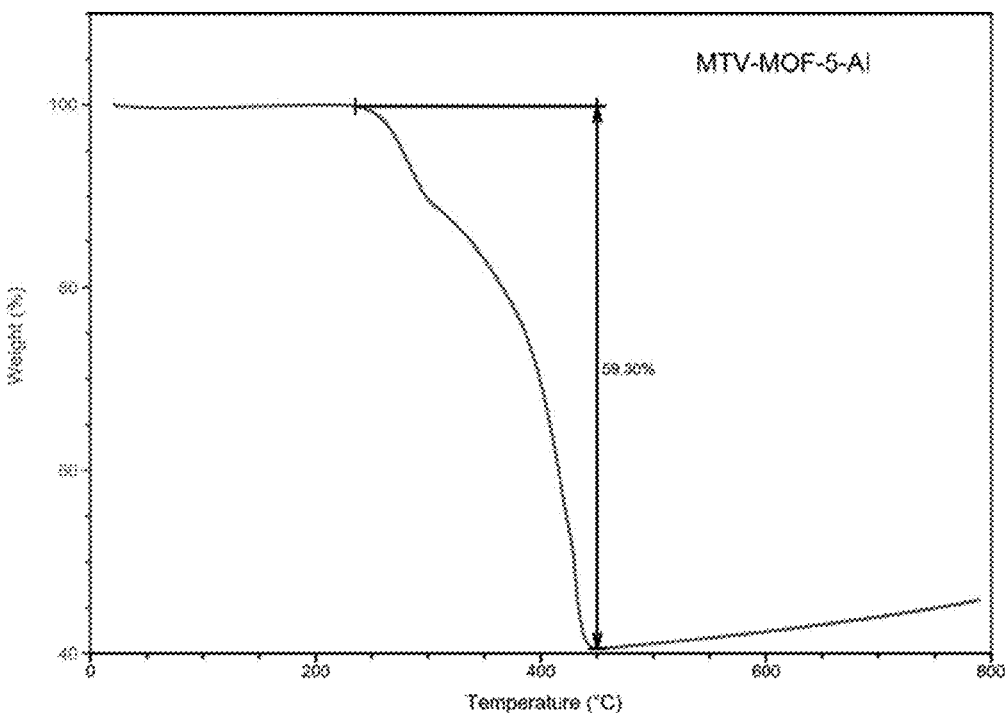
FIG. 28 is a TGA trace of activated MOF-5-AI.
Figure 29:
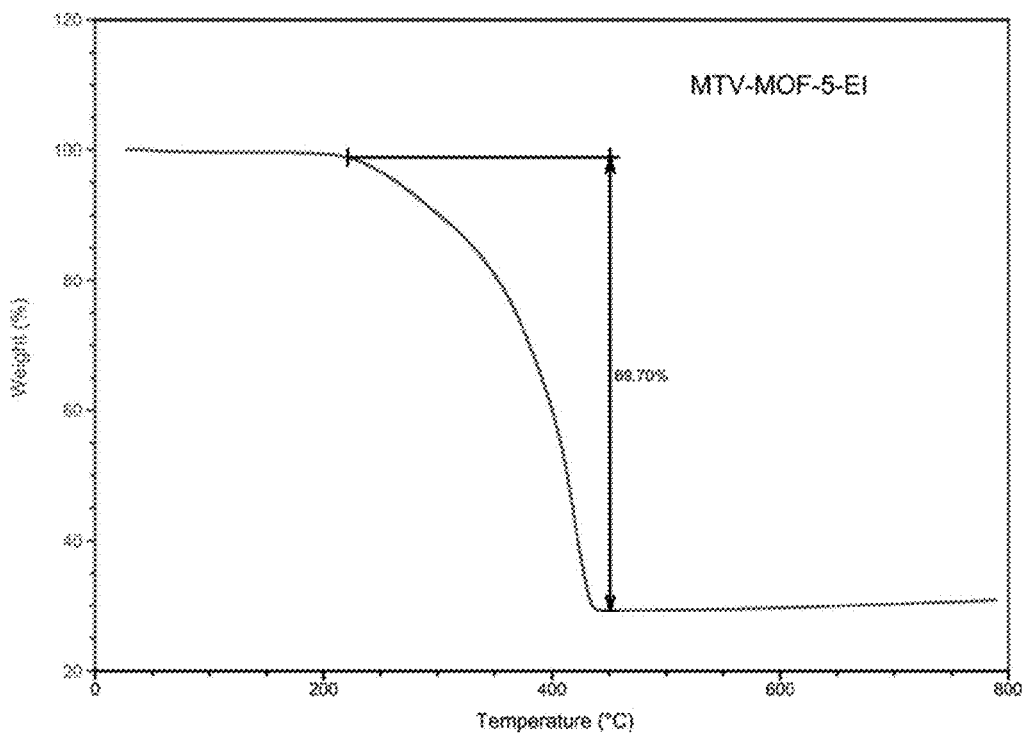
FIG. 29 is a TGA trace of activated mvMOF-5-EI.
Figure 30:
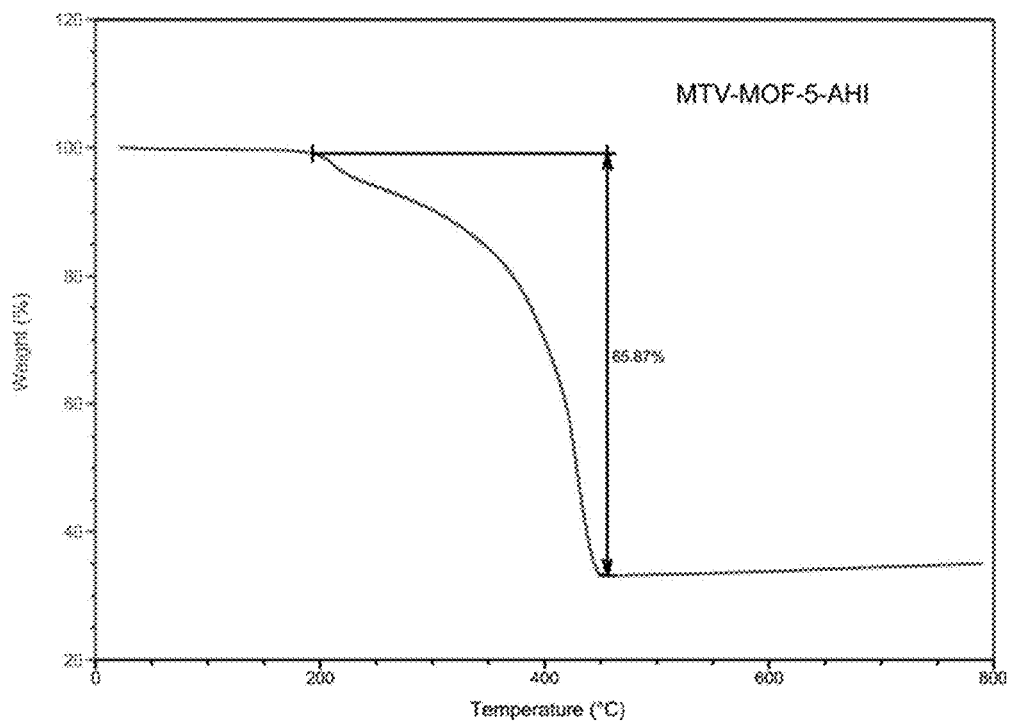
FIG. 30 is a TGA trace of activated MOF-5-AHI.
Figure 31:
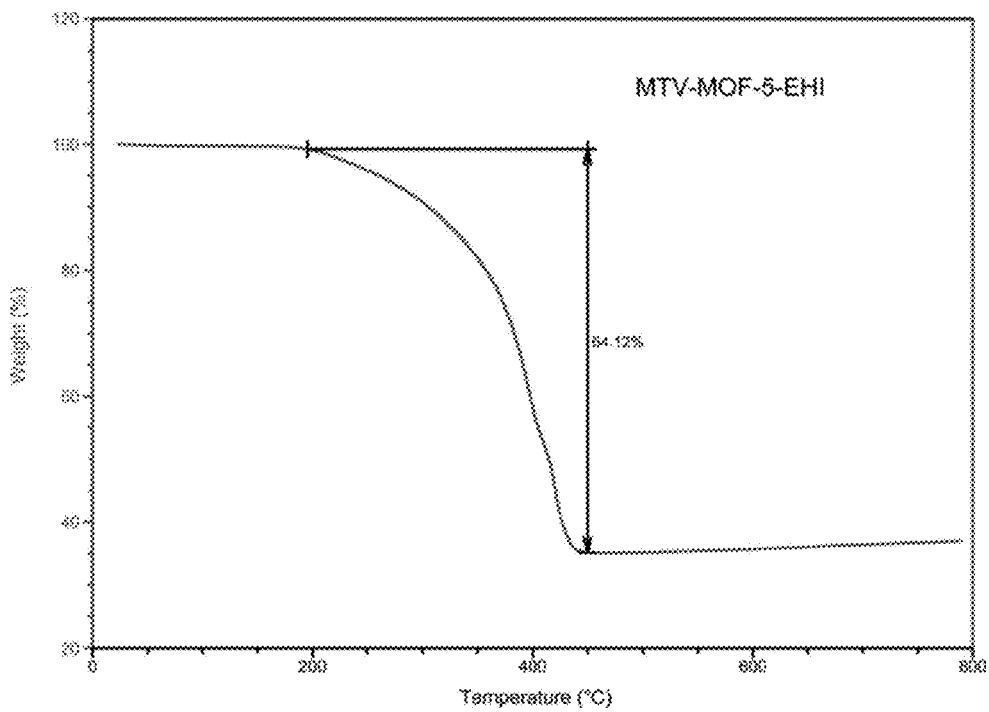
FIG. 31 is a TGA trace of activated mvMOF-5-EHI.
Figure 32:
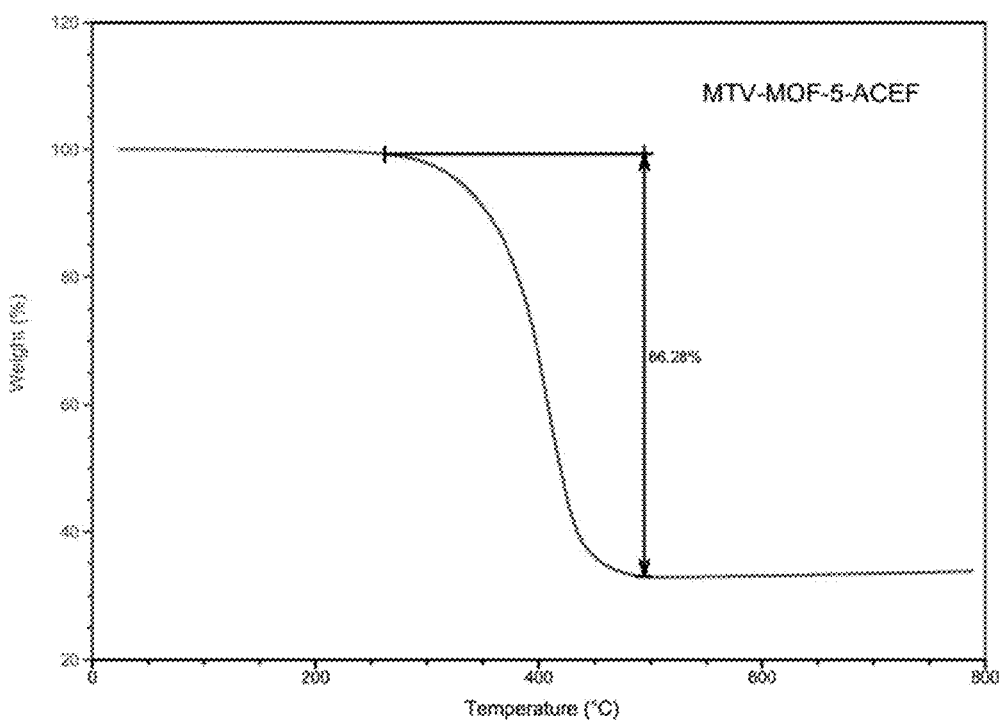
FIG. 32 is a TGA trace of activated mvMOF-5-ACEF.
Figure 33:
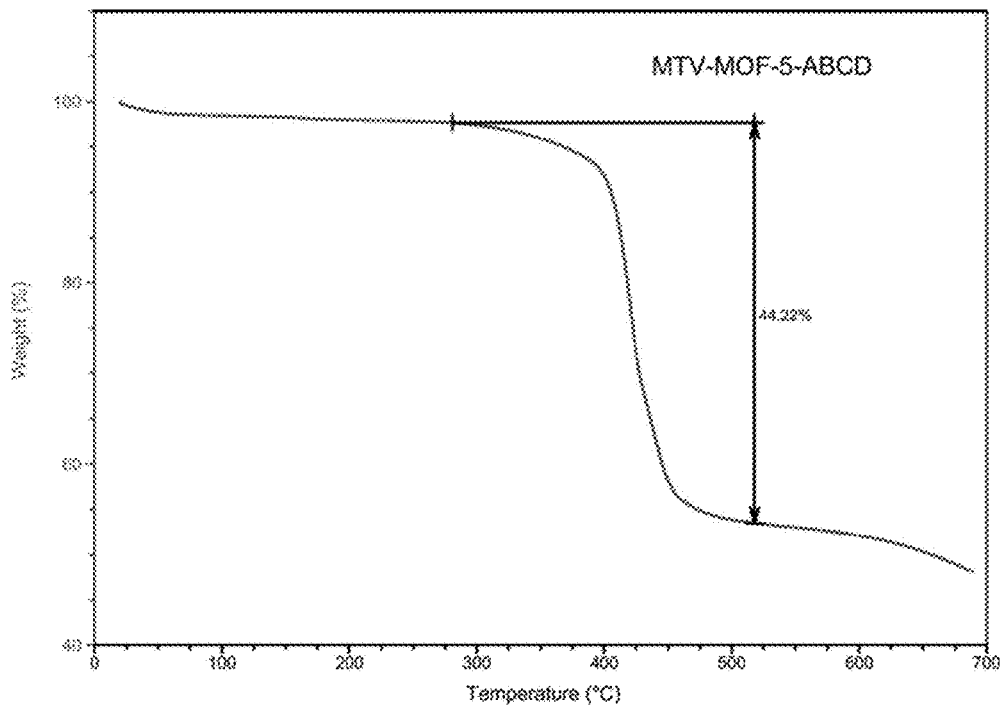
FIG. 33 is a TGA trace of activated mvMOF-5-ABCD.
Figure 34:
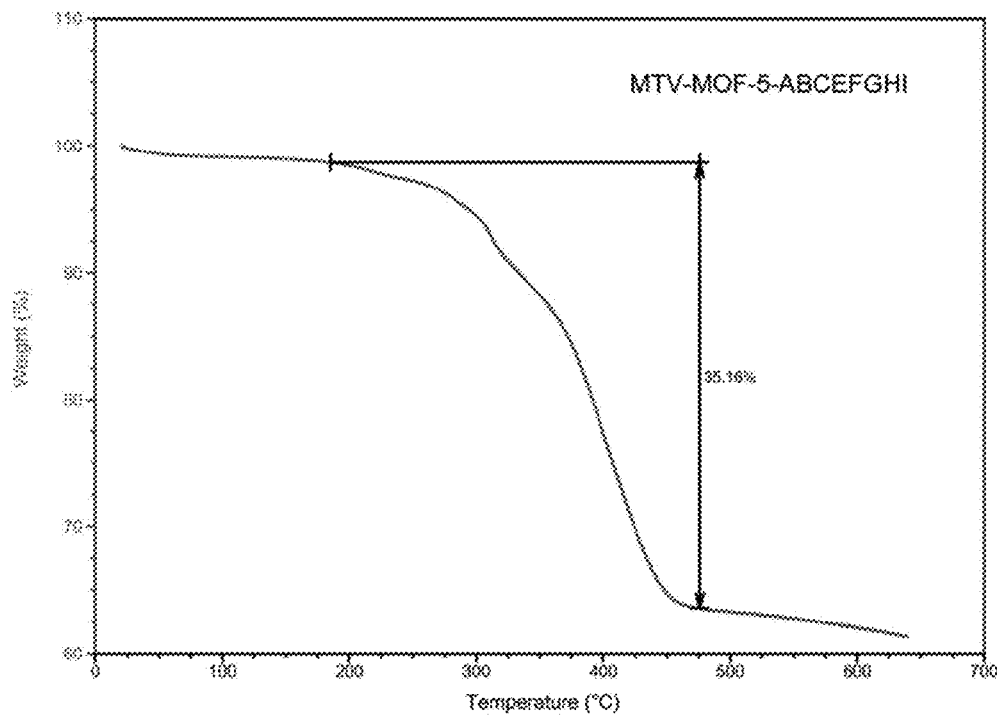
FIG. 34 is a TGA trace of activated MOF-5-ABCEFGHI.

The precise link ratio was obtained from the $^1$H NMR spectra of a DCl digested solution of the mvMOF-5-ABCD solid (Table 1, Link Composition). Resonances with the predicted coupling patterns were observed in the expected regions for each of the unique protons of the links (FIG. 1C). By integrating resonance peak intensities, the links are demonstrated to be present in the MOF in the proportion 1.00:0.12:0.56:0.40, respectively. To show that these ratios are the same in the crystal as in the bulk solid, the solution $^1$H NMR experiments discussed above were performed on 4 different crystals randomly selected from the mvMOF-5-ABCD bulk sample, and showed that the ratios are nearly identical. The same experiment was also performed on mvMOF-5-AB, and -ABCEFGHI, again confirming the bulk homogeneity of the mvMOF series (Table 1, Bulk Homogeneity). Furthermore the porosity and architectural stability of the original MOF-5 structure are preserved in the mvMOF compounds as illustrated by the Type I nitrogen adsorption isotherm, shown in FIG. 1D for mvMOF-5-ABCD, and its high surface area (2860 m$^2$ g$^{-1}$). In addition, by synthesizing mvMOF-ABCD, from a variety of link molar ratios the data demonstrated that, in a given mvMOF, the link ratio can be controlled by modifying the reaction stoichiometry (Table 1, Control of Link Ratio). In essence, this type of control in link ratios translates into control of the population and diversity of functional groups pointing into the pores without altering the underlying connectivity of the primary structure as evidenced by their preserved PXRD patterns (FIG. 28).

X-ray crystallographic studies performed on single crystals of mvMOF-5-AC and -ACEF revealed, as expected, an ordered cubic MOF-5 structure composed of rigid phenyl units joined by $Zn_4O(CO_2)_6$ vertices. The non-hydrogen atoms of the functional groups on the phenyl units in these materials are all present at very low occupancy. Each functional group is required by symmetry to be disordered over two (dimethyl groups of link F) or four (Br group of link C, or nitro group of link E) positions because of an equal probability of their location on the four carbon atoms of the phenyl ring. Br in mvMOF-5-AC can be refined despite its low occupancy and the low contribution to the intensity of the data. In mvMOF-5-ACEF, the occupancies of functional group atoms are also quite low; however, because there is overlap of the positions of Br (link C), N (link E) and C (link F) atoms the difference peak could be located. Given that phenyl unit atoms are present in all mvMOFs, all of these parameters were successfully refined for the backbone non-hydrogen atoms. This clearly indicates that the structures of mvMOFs are not solid solutions but rather they represent a system of varied functional groups covalently linked to an ordered framework.

Figure 24:
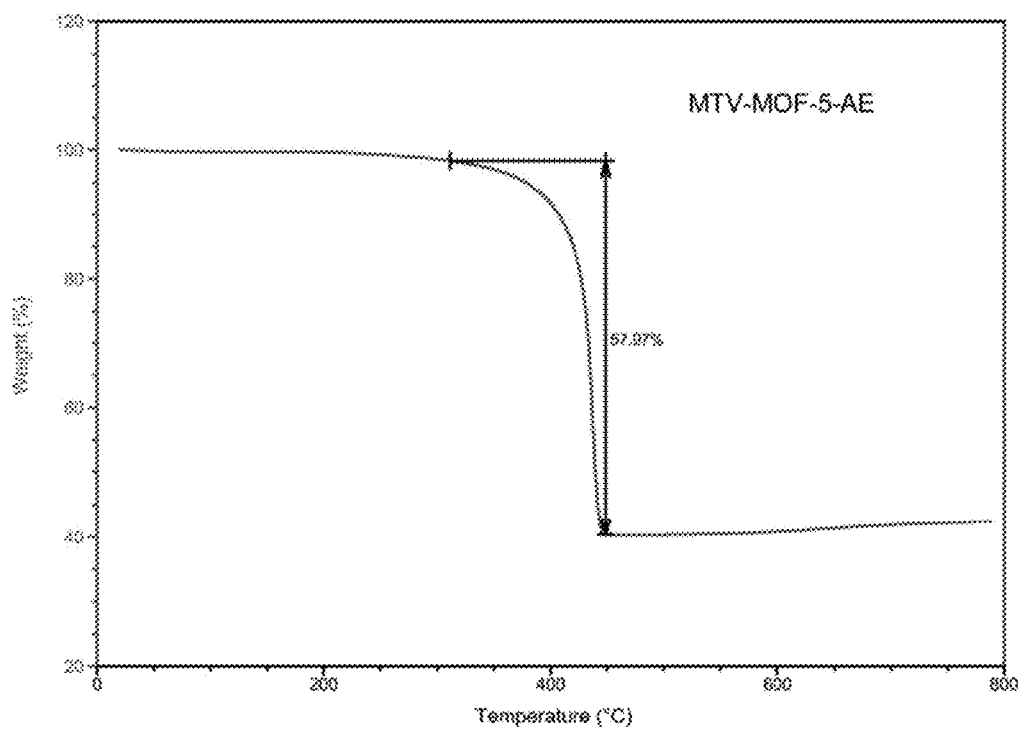
FIG. 24 is a TGA trace of activated mvMOF-5-AE.
Figure 25:
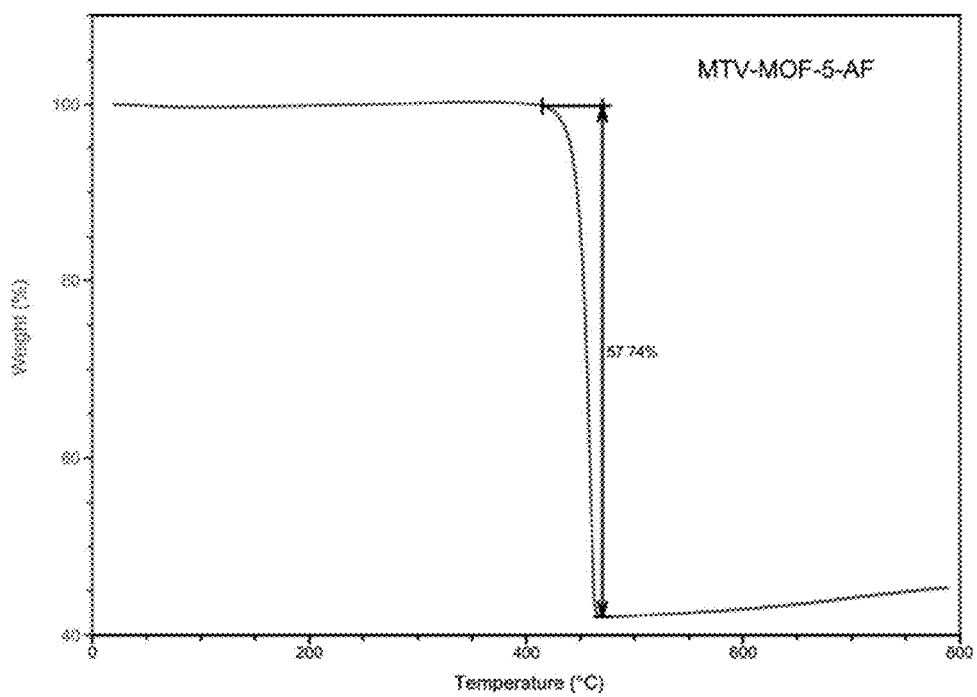
FIG. 25 is a TGA trace of activated mvMOF-5-AF.
Figure 26:
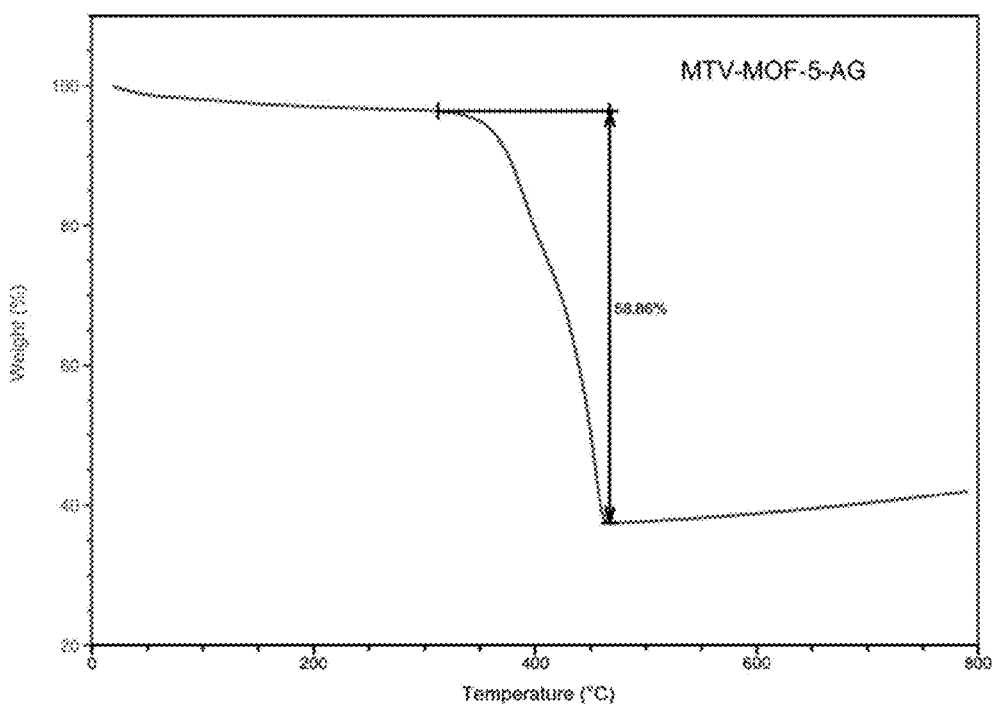
FIG. 26 is a TGA trace of activated MOF-5-AG.
Figure 27:
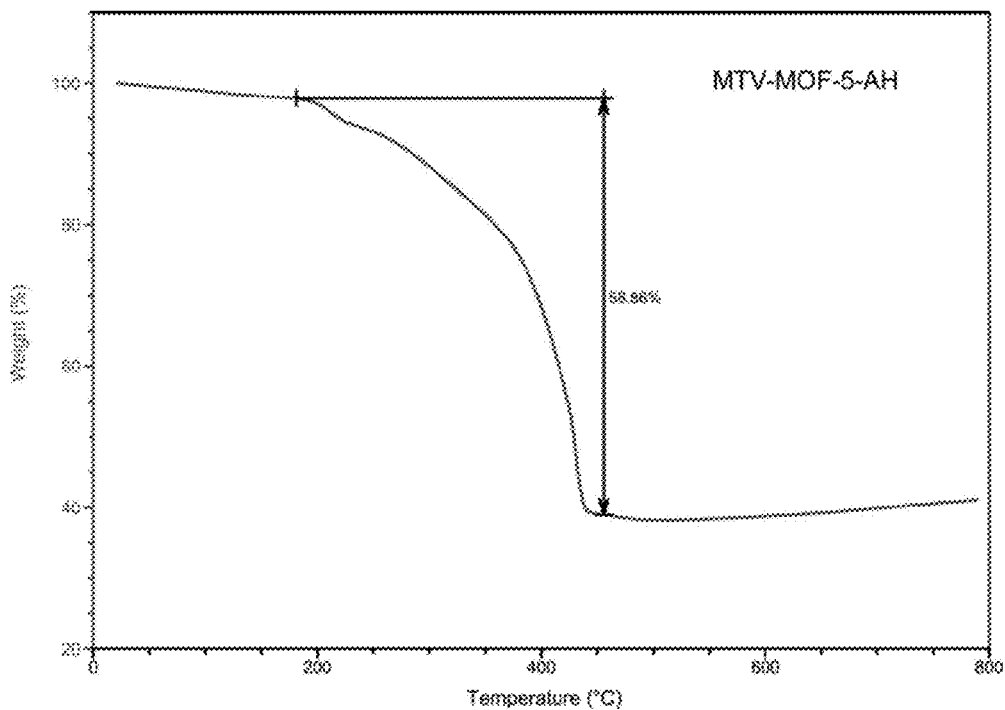
FIG. 27 is a TGA trace of activated mvMOF-5-AH.

Given the uniqueness of the mvMOFs' construct, a significant question that arises is whether the crystals are comprised of macroscopic domains of functionalities, or distinct sequences of functional units repeated throughout the framework backbone. To distinguish these two possibilities large single crystals were prepared of mvMOF-5-AB, -ABCD (FIG. 1E) and -ABCEFGHI of dimensions of 4.0×4.0×2.0 mm, 2.0×2.0×2.0 mm and 2.0×2.0×1.0 mm, respectively. In each case the structure of each single crystal was confirmed by its PXRD pattern (FIG. 24-26). Each crystal was dissected into three equal segments and then the solution $^1$H NMR spectra were collected on acid digested samples of each segment of each crystal, respectively. If macroscopic domains of homogeneous links were present within a single crystal of the mvMOF, a different link ratio would be expected for each of the three segments of the respective parent crystal. However, the data clearly show that the link distribution ratios are identical for each segment of the three mvMOFs studied (Table 1, Segments of Single Crystals), thus suggesting the absence of macroscopic domains. Further evidence supporting this conclusion is the absence of a narrow pore size distribution for mvMOF-5-AI as one would observe for MOF-5 or any other same-link MOF, which suggests that link I is distributed throughout the pores. This does not preclude the presence of microscopic domains where one might expect the dominance of a specific functionality (or a subset of functionalities) over the nanometer scale.

TABLE 1

Ratio of links found in mvMOF crystals (bold) compared to the added ratio. Numerical value of link A was normalized to 1 in each case.

| Compound | A, A | B, B | C, C | D, D | E, E | F, F | G, G | H, H | I, I |
|---|---|---|---|---|---|---|---|---|---|
| Link composition | | | | | | | | | |
| MTV-MOF-5-AB | 1.0, 1 | 0.57, 1 | | | | | | | |
| MTV-MOF-5-AC | 1.0, 1 | | 0.61, 1 | | | | | | |
| MTV-MOF-S-AD | 1.0, 1 | | | 0.63, 1 | | | | | |
| MTV-MOF-5-AE | 1.0, 1 | | | | 0.40, 1 | | | | |
| MTV-MOF-5-AF | 1.0, 1 | | | | | 1.24, 1 | | | |
| MTV-MOF-5-AG | 1.0, 1 | | | | | | 0.52, 1 | | |
| MTV-MOF-5-AH | 1.0, 1 | | | | | | | 0.46, 1 | |
| MTV-MOF-5-AI | 1.0, 1 | | | | | | | | 0.40, 1 |
| MTV-MOF-5-EI* | | | | | 0.20, 1 | | | | 1, 1 |
| MTV-MOF-5-ABC | 1.0, 1 | 0.052, 1 | 0.52, 1 | | | | | | |

TABLE 1-continued

Ratio of links found in mvMOF crystals (bold) compared to the added ratio. Numerical value of link A was normalized to 1 in each case.

| Compound | A, A | B, B | C, C | D, D | E, E | F, F | G, G | H, H | I, I |
|---|---|---|---|---|---|---|---|---|---|
| MTV-MOF-F-AHI | 1.0, 1 | | | | | | | 0.48, 1 | 0.50, 1 |
| MTV-MOF-5-EHI* | | | | | 0.62, 1 | | | 0.89, 1 | 1, 1 |
| MTV-MOF-5-ABCD | 1.0, 1 | 0.12, 1 | 0.56, 1 | 0.40, 1 | | | | | |
| MTV-MOF-5-ACEF | 1.0, 1 | | 0.49, 1 | | 0.22, 1 | 0.62, 1 | | | |
| MTV-MOF-5-ABCHI | 1.0, 1 | 0.017, 1 | 0.22, 1 | | | | | 0.62, 1 | 0.32, 1 |
| MTV-MOF-5-ABCGHI | 1.0, 1 | 0.093, 1 | 0.87, 1 | | | | 0.67, 1 | 0.73, 1 | 0.80, 1 |
| MTV-MOF-5-ABCEGHI | 1.0, 1 | 0.077, 1 | 1.0, 1 | | 0.69, 1 | | 0.77, 1 | 0.73, 1 | 0.96, 1 |
| MTV-MOF-5-ABCEFGHI | 1.0, 1 | 0.14, 1 | 0.56, 1 | | 0.29, 1 | 0.67, 1 | 0.56, 1 | 0.48, 1 | 0.56, 1 |
| Bulk Homogeneity | | | | | | | | | |
| MTV-MOF-5-AB set 1 | 1.0, 1 | 0.58, 1 | | | | | | | |
| MTV-MOF-5-AB set 2 | 1.0, 1 | 0.58, 1 | | | | | | | |
| MTV-MOF-5-AB set 3 | 1.0, 1 | 0.57, 1 | | | | | | | |
| MTV-MOF-5-ABCD set 1 | 1.0, 1 | 0.12, 1 | 0.59, 1 | 0.39, 1 | | | | | |
| MTV-MOF-5-ABCD set 2 | 1.0, 1 | 0.11, 1 | 0.56, 1 | 0.38, 1 | | | | | |
| MTV-MOF-5-ABCD set 3 | 1.0, 1 | 0.11, 1 | 0.53, 1 | 0.36, 1 | | | | | |
| MTV-MOF-5-ABCEFGHI set 1 | 1.0, 1 | 0.12, 1 | 0.56, 1 | | 0.28, 1 | 0.67, 1 | 0.56, 1 | 0.48, 1 | 0.54, 1 |
| MTV-MOF-5-ABCEFGHI set 2 | 1.0, 1 | 0.12, 1 | 0.56, 1 | | 0.28, 1 | 0.67, 1 | 0.56, 1 | 0.51, 1 | 0.56, 1 |
| MTV-MOF-5-ABCEFGHI set 3 | 1.0, 1 | 0.14, 1 | 0.56, 1 | | 0.29, 1 | 0.67, 1 | 0.56, 1 | 0.48, 1 | 0.54, 1 |
| Control of Link Ratio | | | | | | | | | |
| MTV-MOF-5-ABCD-a | 1.0, 1 | 0.12, 1 | 0.56, 1 | 0.40, 1 | | | | | |
| MTV-MOF-5-ABCD-b | 1.0, 0.5 | 0.26, 1 | 1.24, 1 | 1.99, 1.5 | | | | | |
| MTV-MOF-5-ABCD-c | 1.0, 1.5 | 0.06, 1 | 0.43, 1 | 0.30, 0.5 | | | | | |
| MTV-MOF-5-ABCD-d | 1.0, 1 | 0.32, 1.5 | 0.26, 0.5 | 0.44, 1 | | | | | |
| MTV-MOF-5-ABCD-e | 1.0, 1 | 0.03, 0.5 | 1.0, 1.5 | 0.67, 1 | | | | | |
| Segments of a Single Crystal | | | | | | | | | |
| MTV-MOF-5-AB segment 1 | 1.0, 1 | 0.57, 1 | | | | | | | |
| MTV-MOF-5-AB segment 2 | 1.0, 1 | 0.58, 1 | | | | | | | |
| MTV-MOF-5-AB segment 3 | 1.0, 1 | 0.54, 1 | | | | | | | |
| MTV-MOF-5-ABCD segment 1 | 1.0, 1 | 0.10, 1 | 0.48, 1 | 0.31, 1 | | | | | |
| MTV-MOF-5-ABCD segment 2 | 1.0, 1 | 0.11, 1 | 0.50, 1 | 0.31, 1 | | | | | |
| MTV-MOF-5-ABCD segment 3 | 1.0, 1 | 0.11, 1 | 0.51, 1 | 0.34, 1 | | | | | |
| MTV-MOF-5-ABCEFGHI segment 1 | 1.0, 1 | 0.05, 1 | 0.52, 1 | | 0.15, 1 | 0.46, 1 | 0.48, 1 | 0.42, 1 | 0.57, 1 |
| MTV-MOF-5-ABCEFGHI segment 2 | 1.0, 1 | 0.06, 1 | 0.53, 1 | | 0.15, 1 | 0.48, 1 | 0.49, 1 | 0.45, 1 | 0.59, 1 |
| MTV-MOF-5-ABCEFGHI segment 3 | 1.0, 1 | 0.05, 1 | 0.50, 1 | | 0.14, 1 | 0.45, 1 | 0.47, 1 | 0.40, 1 | 0.58, 1 |

*Numerical value of link E was normalized to 1.

Figure 2:
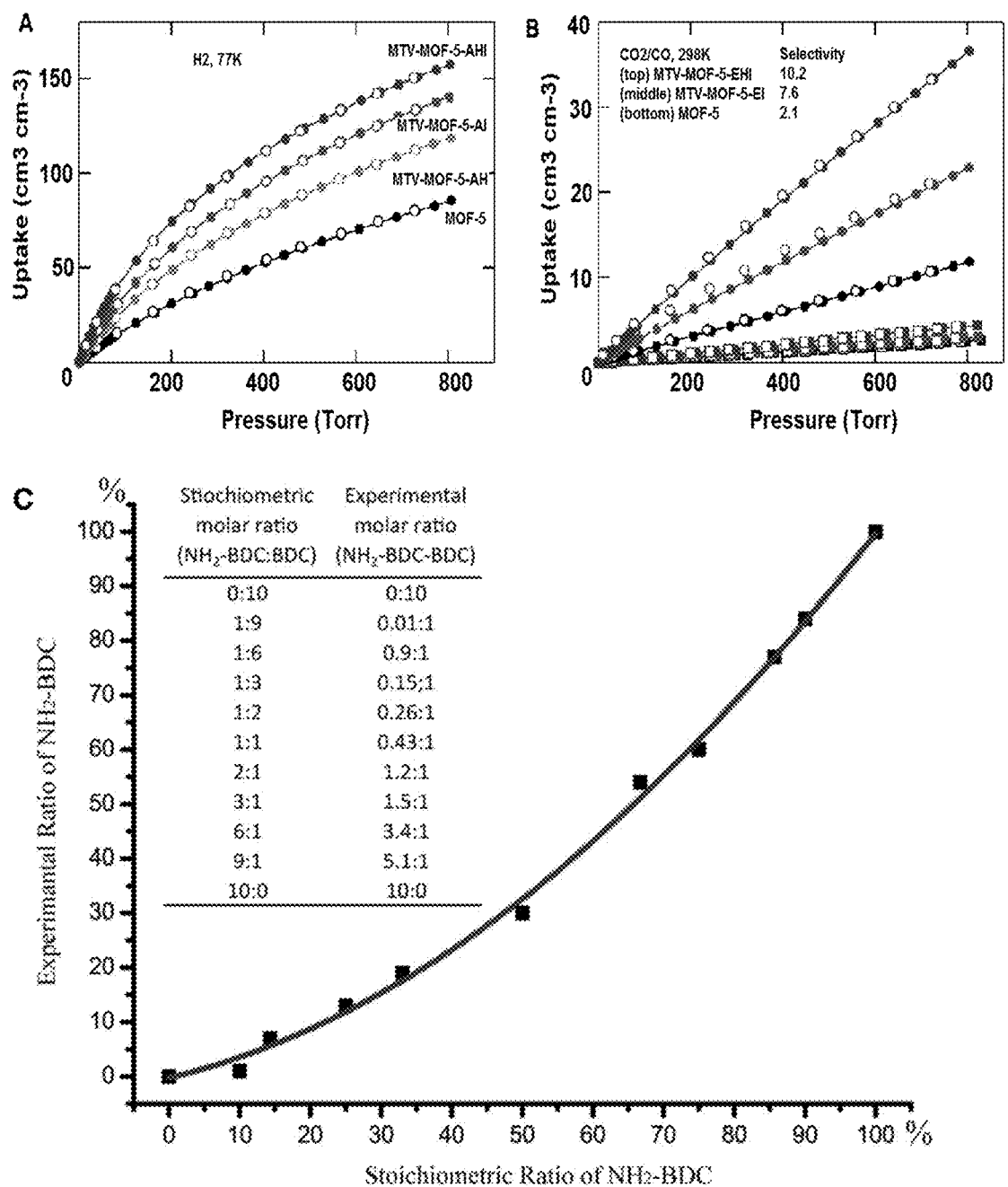
FIG. 2A-C shows (A) $H_2$ adsorption isotherm at 77 K of mvMOF-5-AH, -AI, -AHI and MOF-5. (B) $CO_2$ (circles) and CO (squares) adsorption isotherms at 298 K of mvMOF-5-EI, -EHI and MOF-5. Adsorption and desorption branches are represented by closed circles (squares for CO) and open circles (squares for CO), respectively. (C) Plot of the percent ratio of $NH_2$-BDC in MOF-5-AB determined by solution $^1H$ NMR versus the stoichiometric ratio used in the synthesis together with the tabulated data of the molar ratio of $NH_2$-BDC versus BDC.
Figure 3:
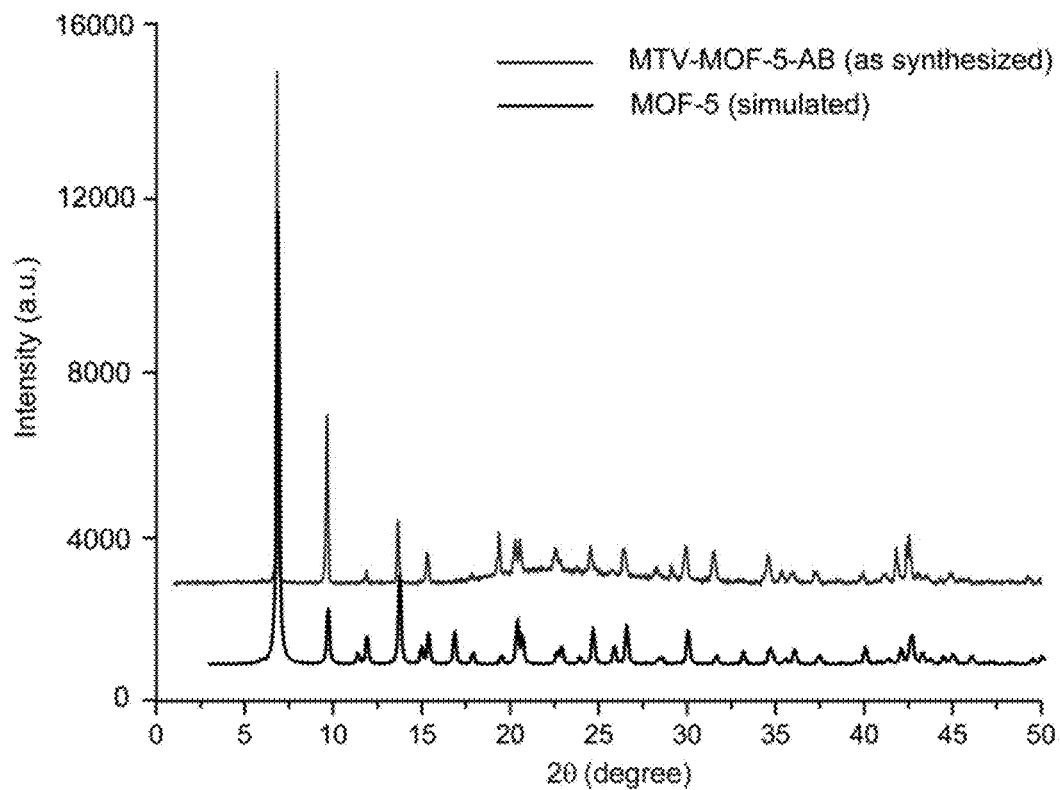
FIG. 3 shows a comparison of the experimental PXRD pattern of as-prepared mvMOF-5-AB (top) with the simulated MOF-5 diffraction pattern (bottom). The very high degree of correspondence between the patterns indicates that the bulk material has the same topology as MOF-5.

The possible presence of distinct sequences of functionalities along the MOF backbone would inevitably lead to a complex pore environment and provide opportunities for uncovering unusual properties. Since same-link MOF-5 structure is known to take up a significant amount of gases (e.g., $H_2$, $CO_2$), the mvMOFs were tested in these applications, and to determine whether their performance is greater than that of their constituents. In FIG. 2A, a comparison between the $H_2$ storage capacities of mvMOF-5-AHI, -AH, -HI and MOF-5 is shown. Remarkably, the isotherms clearly demonstrate that the uptake capacity of mvMOF-5-AHI is greater than that of mvMOF-5-AH, -HI and -A (MOF-5) by a maximum of 84%. Similarly, an unusual increase in the selective uptake capacity of $CO_2$ over CO was observed: 400% better selectivity in the case of mvMOF-5-EHI for $CO_2$ compared to MOF-5 (FIG. 2B).

These findings demonstrate that the properties of mvMOFs are not simple linear combinations of their constituents, thus supporting the notion that the sequence of functionalities within mvMOF can be useful as code for the enhancement of a specific property or achieving a new property.

Detailed synthetic procedures for the preparation of mvMOF including multi-gram scale products, and experimental and simulated PXRD patterns.

Terephthalic acid (Benzene-1,4-dicaboxylic acid or $BDCH_2$), 2-aminoterephthalic acid ($NH_2$-$BDCH_2$), 2-bromoterephthalic acid (Br-$BDCH_2$), 2,5-dichloroterephthalic acid (($Cl)_2$-$BDCH_2$), 2-nitroterephthalic acid ($NO_2$-$BDCH_2$), naphthalene-1,4-dicarboxylic acid ($C_4H_4$-$BDCH_2$) were purchased from the Aldrich Chemical Co. N,N-dimethylformamide (DMF) is purchased from the Fisher Scientific International Inc. Zinc nitrate tetrahydrate $Zn(NO_3)_2 \cdot 4H_2O$ was purchased from EM Science. 2,5-dimethylterephthalic acid (($CH_3)_2$-$BDCH_2$) was purchased from TCI America. All starting materials above were used without further purification. N,N-diethylformamide (DEF, BASF) solvent was purified by filtration through a column filled with activated carbon (Calgon) and silica gel (EMD, silica gel 60), and chloroform (Fisher, HPLC grade, pentene stabilized) was dried over freshly activated molecular sieves 4A prior to use. 2,5-Bis(allyloxy)terephthalic acid (($C_3H_5O)2$-$BDCH_2$), 2,5-bis(benzyloxy)terephthalic acid (($C_7H_7O)_2$-$BDCH_2$) were synthesized.

Multi-variate metal-organic framework (mvMOFs) are synthesized by mixing varied amounts of chemically functionalized benzene dicarboxylic acids with zinc nitrate in DEF/DMF at 85-100° C. for 24-48 h. The resultant crystalline material is then immersed in DMF for 24 h and then sequentially in chloroform for three 24 h periods. Finally, this porous material is activated by removing the solvent under vacuum for 24 h at room temperature or heat up to 120° C.

In order to precisely control the amount of starting material, a solution of teraphthalic acid link in DMF/DEF (0.025-0.10 M (1 M=1 mol $dm^{-3}$)) and a solution of zinc nitrate tetrahydrate in DMF/DEF (0.10 M) were used as stock solutions. DMF and DEF have been chosen as the solvents of synthesis due to their high boiling points, which are suitable for the solvothermal synthesis. A lower boiling solvent may result in the precipitation of the reactants rather than of the product. After reaction, the crystals were examined under optical microscope, collected, and characterized by powder X-ray diffraction (PXRD). PXRD data of a crushed large single cubic crystal was recorded on a Bruker AXS D8 Advance diffractometer operated at 40 kV, 40 mA for Cu Kα, ($\lambda$=1.5406 Å) with a scan speed of 3°/min and a step size of 0.050° in 2θ. Simulated MOF-5 PXRD pattern was calculated using software Powder Cell v.2.2 from the single crystal structure published earlier.

$^1$H NMR of digested mvMOFs: In general, 8 mg of dried (or solvent exchanged with DMF) mvMOF was digested and dissolved with sonication in 1.0 mL dilute DCl solution (prepared from 200 μL of 20% DCl/D$_2$O solution (Aldrich) and 10 mL DMSO-d6). The digestion solution was used directly for $^1$H-NMR.

Figure 4:
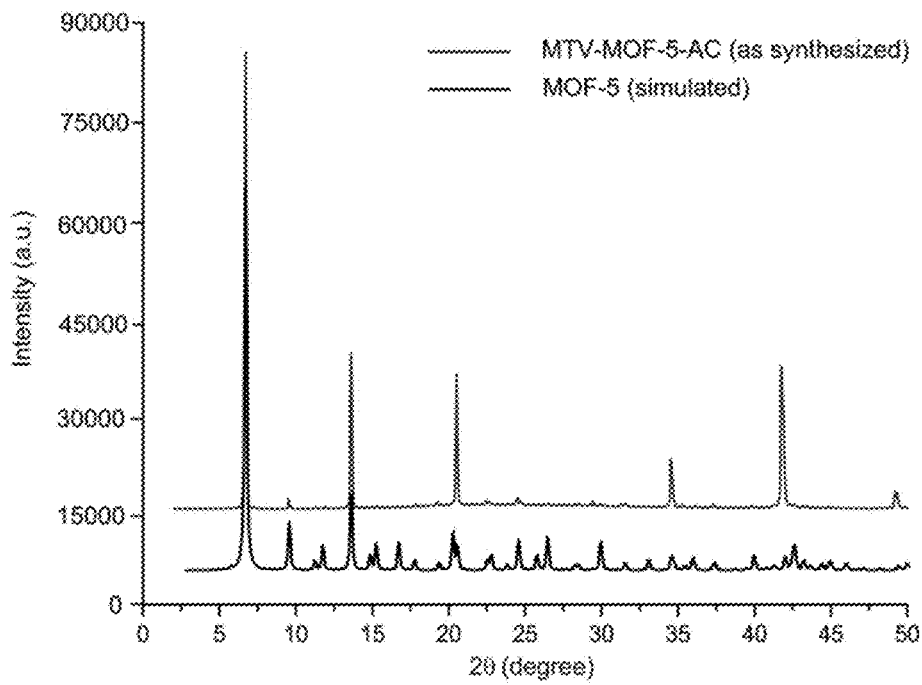
FIG. 4 shows a comparison of the experimental PXRD pattern of as-prepared mvMOF-5-AC (top) with the simulated MOF-5 diffraction pattern (bottom). The very high degree of correspondence between the patterns indicates that the bulk material has the same topology as MOF-5.

Synthesis of mvMOFs: mvMOF-5-AB, $Zn_4O(BDC)_{1.92}(NH_2\text{-}BDC)_{1.08}$: 0.10 mL of BDCH$_2$ stock solution (0.10 M, 1.0×10$^{-5}$ mol), 0.10 mL of NH$_2$-BDCH$_2$ stock solution (0.10 M, 1.0×10$^{-5}$ mol), 0.20 mL of Zn(NO$_3$)$_2$.4H$_2$O stock solution (0.30 M, 6.0×10-5 mol) and 0.60 mL of DEF were added in sequence in to a 4 mL glass vial. The vial was sealed and heated in an isothermal oven at 100° C. and allowed to react solvothermally for 48 h. The product was in the form of cubic shaped brown single crystals. PXRD was checked, it matches the simulated MOF-5 powder diffraction pattern (FIG. 4).

$^1$H NMR of the digested mvMOF-5-AB crystals (400 MHz, DMSO-d6). BDCH$_2$ δ: 8.00 (s, 4H). NH$_2$-BDCH$_2$ δ: 7.03 (d, 1H), 7.38 (s, 1H), 7.74 (d, 1H). Molar ratio based on integration of the peaks: BDC:NH$_2$-BDC=1:0.57.

mvMOF-5-AC, $Zn_4O(BDC)_{1.86}(Br\text{-}BDC)_{1.14}$:

0.10 mL of Br-BDCH$_2$ stock solution (0.10 M, 1.0×10$^{-5}$ mol), 0.10 mL of BDCH$_2$ stock solution (0.10 M, 1.0×10$^{-5}$ mol), 0.20 mL of Zn(NO$_3$)$_2$.4H$_2$O stock solution (0.30 M, 6.0×10$^{-5}$ mol) and 0.60 mL of DEF were added in sequence in to a 4 mL glass vial. The vial was sealed and heated in an isothermal oven at 100° C. and allowed to react solvothermally for 24 h. The product was in the form of cubic shaped pale yellow single crystals. PXRD was checked, it matches the simulated MOF-5 structure (FIG. 4).

Figure 5:
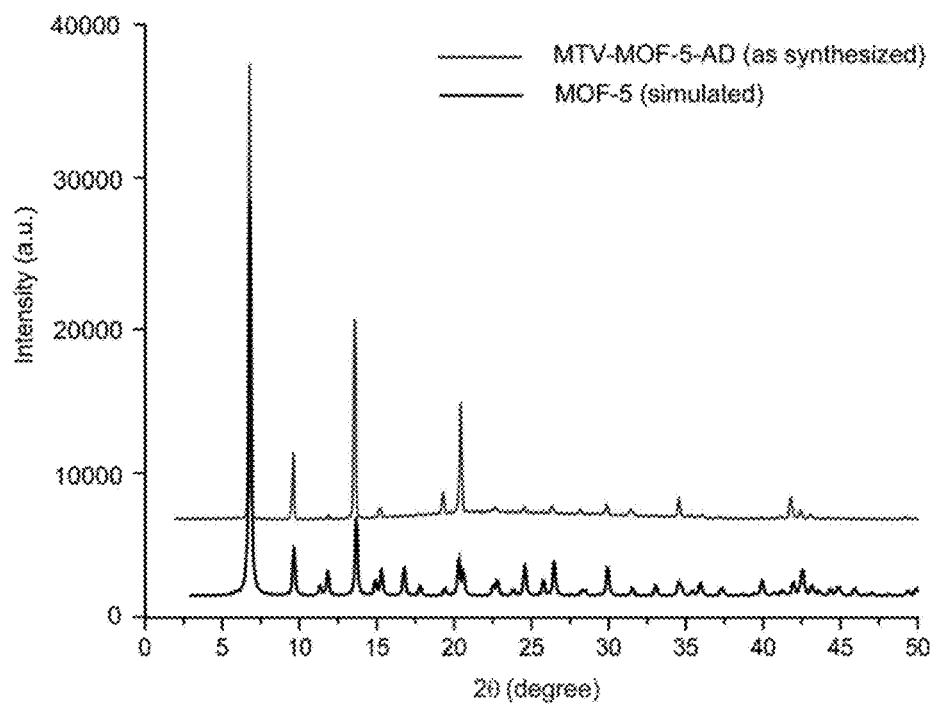
FIG. 5 shows a comparison of the experimental PXRD pattern of as-prepared mvMOF-5-AD (top) with the simulated MOF-5 diffraction pattern (bottom). The very high degree of correspondence between the patterns indicates that the bulk material has the same topology as MOF-5.

$^1$H NMR of the digested mvMOF-5-AC crystals (400 MHz, DMSO-d6). BDCH$_2$ δ: 8.00 (s, 4H). Br-BDCH$_2$ δ: 7.78 (d, 1H), 7.94 (d, 1H), 8.10 (s, 1H). Molar ratio based on integration of the peaks: BDC:NH$_2$-BDC=1:0.61.

mvMOF-5-AD, $Zn_4O(BDC)_{1.83}((Cl)_2\text{-}BDC)_{1.17}$:

0.10 mL of (Cl)$_2$-BDCH$_2$ stock solution (0.10 M, 1.0×10$^{-5}$ mol), 0.10 mL of BDCH$_2$ stock solution (0.10 M, 1.0×10$^{-5}$ mol), 0.20 mL of Zn(NO$_3$)$_2$.4H$_2$O stock solution (0.30 M, 6.0×10$^{-5}$ mol) and 0.60 mL of DEF were added in sequence in to a 4 mL glass vial. The vial was sealed and heated in an isothermal oven at 100° C. and allowed to react solvothermally for 24 h. The product was in the form of cubic shaped pale yellow single crystals. PXRD was checked, it matches the simulated MOF-5 structure (FIG. 5).

Figure 6:
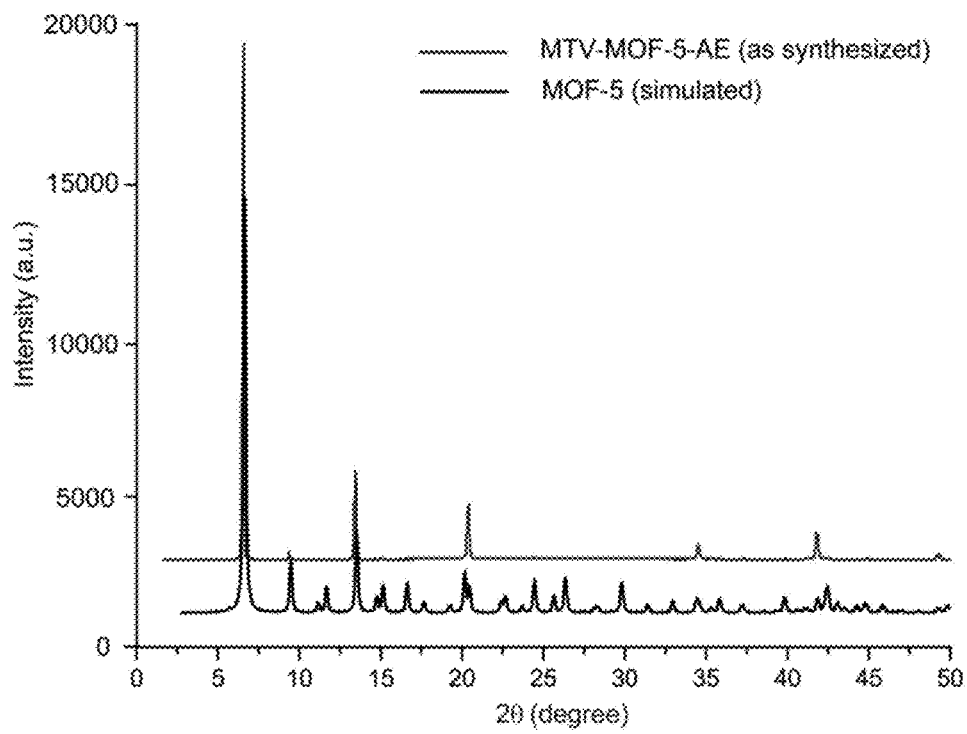
FIG. 6 shows a comparison of the experimental PXRD pattern of as-prepared mvMOF-5-AE (top) with the simulated MOF-5 diffraction pattern (bottom). The very high degree of correspondence between the patterns indicates that the bulk material has the same topology as MOF-5.

$^1$H NMR of the digested mvMOF-5-AD crystals (400 MHz, DMSO-d6). BDCH$_2$ δ: 8.00 (s, 4H). (Cl)$_2$-BDCH$_2$ δ: 7.90 (s, 2H). Molar ratio based on integration of the peaks: BDC:(Cl)$_2$-BDC=1:0.63.

mvMOF-5-AE, $Zn_4O(BDC)_{2.13}(NO_2\text{-}BDC)_{0.87}$:

0.10 mL of NO$_2$-BDCH$_2$ stock solution (0.10 M, 1.0×10$^{-5}$ mol), 0.10 mL of BDCH$_2$ stock solution (0.10 M, 1.0×10$^{-5}$ mol), 0.20 mL of Zn(NO$_3$)$_2$.4H$_2$O stock solution (0.30 M, 6.0×10$^{-5}$ mol) and 0.60 mL of DEF were added in sequence in to a 4 mL glass vial. The vial was sealed and heated in an isothermal oven at 100° C. and allowed to react solvothermally for 48 h. The product was in the form of cubic shaped brown single crystals. PXRD was checked, it matches the simulated MOF-5 structure (FIG. 6).

Figure 7:
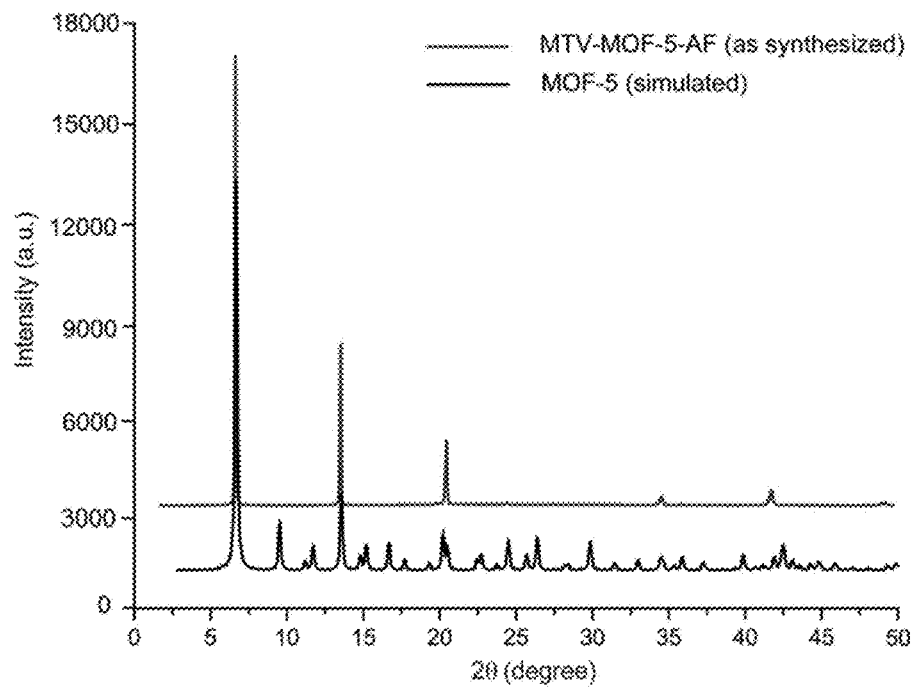
FIG. 7 shows a comparison of the experimental PXRD pattern of as-prepared mvMOF-5-AF (top) with the simulated MOF-5 diffraction pattern (bottom). The very high degree of correspondence between the patterns indicates that the bulk material has the same topology as MOF-5.

$^1$H NMR of the digested mvMOF-5-AE crystals (400 MHz, DMSO-d6). BDCH$_2$ δ: 8.00 (s, 4H). NO$_2$-BDCH$_2$ δ: 7.92 (d, 1H), 8.25 (d, 1H), 8.35 (s, 1H). Molar ratio based on integration of the peaks: BDC:NO$_2$-BDC=1:0.40.

mvMOF-5-AF, $Zn_4O(BDC)_{1.35}((CH_3)_2\text{-}BDC)_{1.65}$:

0.10 mL of (CH$_3$)$_2$-BDCH$_2$ stock solution (0.10 M, 1.0×10$^{-5}$ mol), 0.10 mL of BDCH$_2$ stock solution (0.10 M, 1.0×10$^{-5}$ mol), 0.20 mL of Zn(NO$_3$)$_2$.4H$_2$O stock solution (0.30 M, 6.0×10$^{-5}$ mol) and 0.60 mL of DEF were added in sequence in to a 4 mL glass vial. The vial was sealed and heated in an isothermal oven at 100° C. and allowed to react solvothermally for 24 h. The product was in the form of cubic shaped pale yellow single crystals. PXRD was checked, it matches the simulated MOF-5 structure (FIG. 7).

Figure 8:
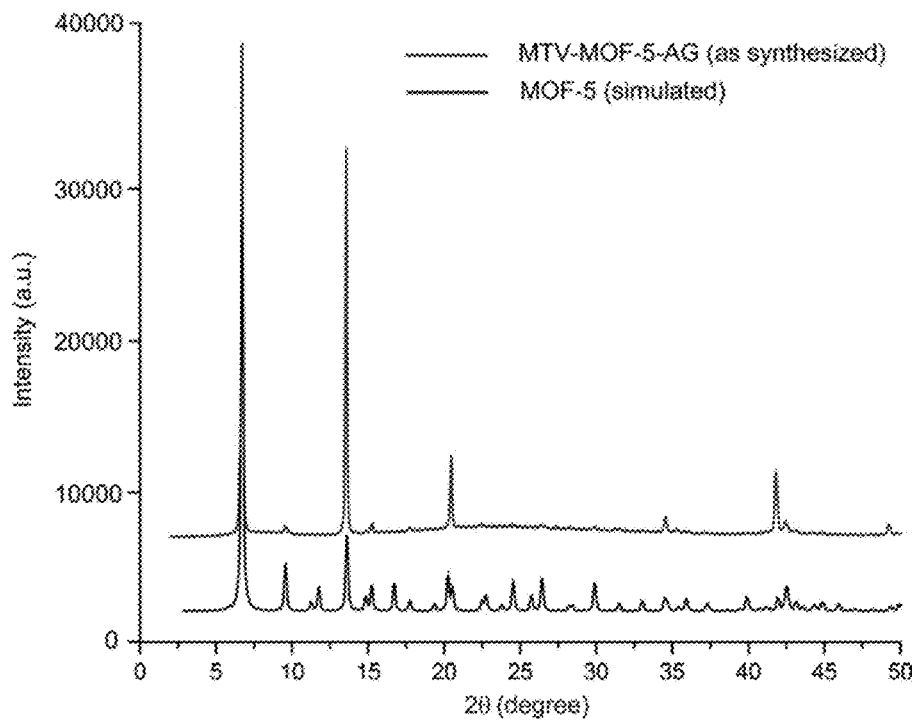
FIG. 8 shows a comparison of the experimental PXRD pattern of as-prepared mvMOF-5-AG (top) with the simulated MOF-5 diffraction pattern (bottom). The very high degree of correspondence between the patterns indicates that the bulk material has the same topology as MOF-5.

$^1$H NMR of the digested mvMOF-5-AF crystals (400 MHz, DMSO-d6). BDCH$_2$ δ: 8.00 (s, 4H). (CH$_3$)$_2$-BDCH$_2$ δ: 2.43 (s, 6H), 7.64 (s, 2H). Molar ratio based on integration of the peaks: BDC:(CH$_3$)$_2$-BDC=1:1.24.

mvMOF-5-AG, $Zn_4O(BDC)_{1.98}(C_4H_4\text{-}BDC)_{1.02}$:

0.40 mL of C$_4$H$_4$-BDCH$_2$ stock solution (0.025 M, 1.0×10$^{-5}$ mol), 0.10 mL of BDCH$_2$ stock solution (0.10 M, 1.0×10$^{-5}$ mol), 0.20 mL of Zn(NO$_3$)$_2$.4H$_2$O stock solution (0.30 M, 6.0×10$^{-5}$ mol) and 0.30 mL of DEF were added in sequence in to a 4 mL glass vial. The vial was sealed and heated in an isothermal oven at 100° C. and allowed to react solvothermally for 24 h. The product was in the form of cubic shaped pale green single crystals. PXRD was checked, it matches the simulated MOF-5 structure (FIG. 8).

Figure 9:
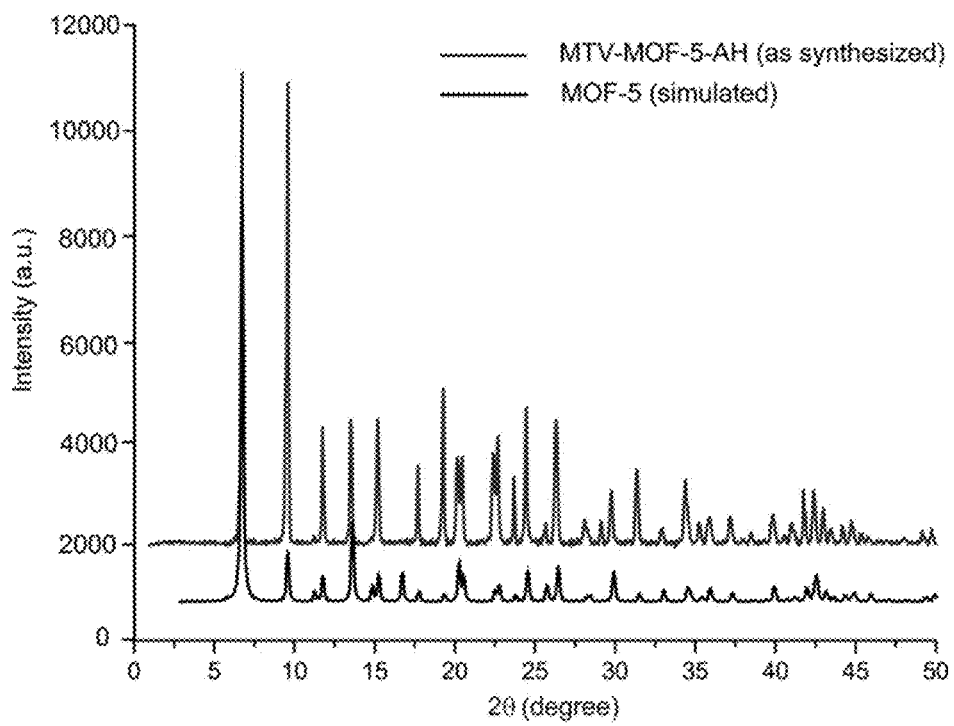
FIG. 9 shows a comparison of the experimental PXRD pattern of as-prepared mvMOF-5-AH (top) with the simulated MOF-5 diffraction pattern (bottom). The very high degree of correspondence between the patterns indicates that the bulk material has the same topology as MOF-5.

$^1$H NMR of the digested mvMOF-5-AG crystals (400 MHz, DMSO-d6). BDCH$_2$ δ: 8.00 (s, 4H). C$_4$H$_4$-BDCH$_2$ δ: 7.64-7.68 (m, 2H), 8.05 (s, 2H), 8.70-8.74 (m, 2H). Molar ratio based on integration of the peaks: BDC:C$_4$H$_4$-BDC=1:0.52.

mvMOF-5-AH, $Zn_4O(BDC)_{2.04}((C_3H_5O)_2\text{-}BDC)_{0.96}$:

0.10 mL of (C$_3$H$_5$O)$_2$-BDCH$_2$ stock solution (0.10 M, 1.0×10$^{-5}$ mol), 0.10 mL of BDCH$_2$ stock solution (0.10 M, 1.0×10$^{-5}$ mol), 0.20 mL of Zn(NO$_3$)$_2$.4H$_2$O stock solution (0.30 M, 6.0×10$^{-5}$ mol) and 0.60 mL of DEF were added in sequence in to a 4 mL glass vial. The vial was sealed and heated in an isothermal oven at 100° C. and allowed to react solvothermally for 24 h. The product was in the form of cubic shaped brown single crystals. PXRD was checked, it matches the simulated MOF-5 structure (FIG. 9).

$^1$H NMR of the digested mvMOF-5-AH crystals (400 MHz, DMSO-d6). BDCH$_2$ δ: 8.00 (s, 4H). (C$_3$H$_5$O)$_2$-BDCH$_2$ δ: 4.54 (d, 4H), 5.19 (d, 2H), 5.40 (d, 2H), 5.94-6.01 (m, 2H), 7.30 (s, 2H).

Figure 10:
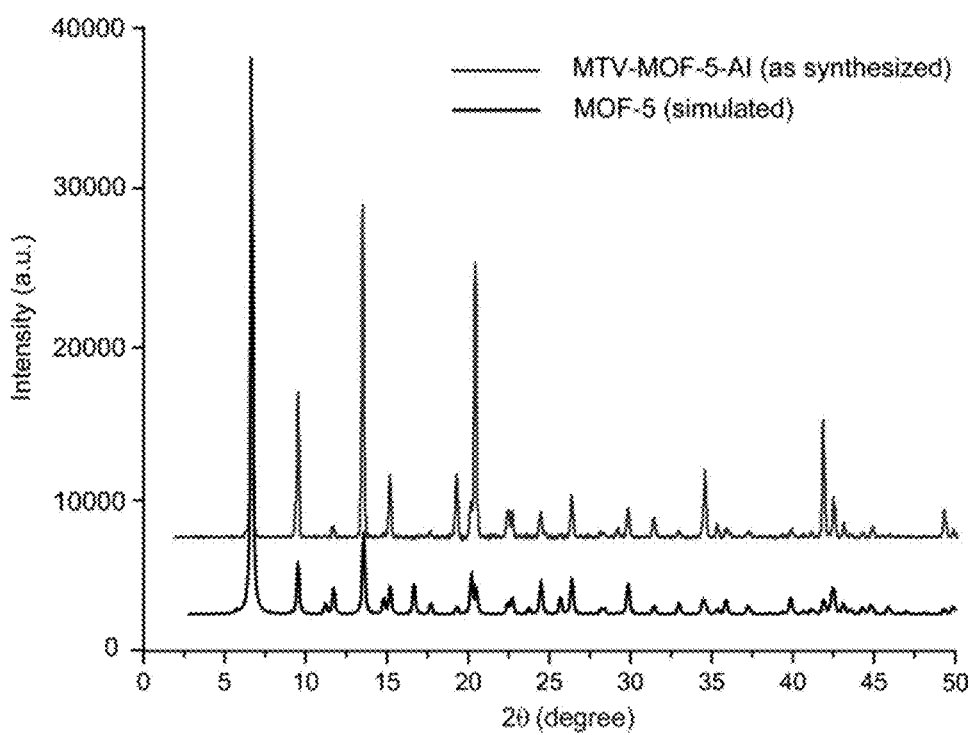
FIG. 10 shows a comparison of the experimental PXRD pattern of as-prepared mvMOF-5-AI (top) with the simulated MOF-5 diffraction pattern (bottom). The very high degree of correspondence between the patterns indicates that the bulk material has the same topology as MOF-5.

Molar ratio based on integration of the peaks: BDC:(C$_3$H$_5$O)$_2$-BDC=1:0.46.

mvMOF-5-AI, $Zn_4O(BDC)_{2.13}((C_7H_7O)_2\text{-}BDC)_{0.87}$:

0.10 mL of (C$_7$H$_7$O)$_2$-BDCH$_2$ stock solution (0.10 M, 1.0×10$^{-5}$ mol), 0.10 mL of BDCH$_2$ stock solution (0.10 M, 1.0×10$^{-5}$ mol), 0.20 mL of Zn(NO$_3$)$_2$.4H$_2$O stock solution (0.30 M, 6.0×10$^{-5}$ mol) and 0.60 mL of DEF were added in sequence in to a 4 mL glass vial. The vial was sealed and heated in an isothermal oven at 100° C. and allowed to react solvothermally for 24 h. The product was in the form of cubic shaped pale yellow single crystals. PXRD was checked, it matches the simulated MOF-5 structure (FIG. 10).

Figure 11:
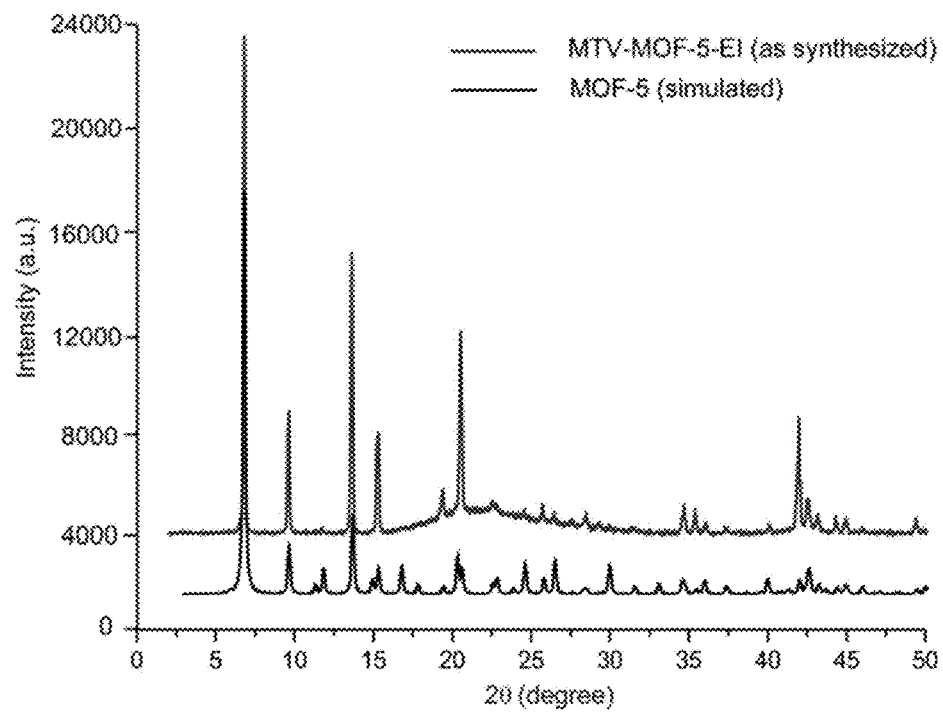
FIG. 11 shows a comparison of the experimental PXRD pattern of as-prepared mvMOF-5-EI (top) with the simulated MOF-5 diffraction pattern (bottom). The very high degree of correspondence between the patterns indicates that the bulk material has the same topology as MOF-5.

¹H NMR of the digested mvMOF-5-AI crystals (400 MHz, DMSO-d6). BDCH₂ δ: 8.00 (s, 4H). (C₇H₇O)₂-BDCH₂ δ: 5.12 (s, 4H), 7.25-7.44 (m, 12H). Molar ratio based on integration of the peaks: BDC:(C₇H₇O)₂-BDC=1:0.40.

mvMOF-5-EI, $Zn_4O((C_7H_7O)_2\text{-BDC})_{2.49}(NIDC)_{0.51}$:

0.10 mL of (C₇H₇O)₂-BDCH₂ stock solution (0.10 M, 1.0×10⁻⁵ mol), 0.40 mL of NO₂-BDCH₂ stock solution (0.025 M, 1.0×10⁻⁵ mol), 0.20 mL of Zn(NO₃)₂.4H₂O stock solution (0.30 M, 6.0×10⁻⁵ mol) and 0.30 mL of DEF were added in sequence in to a 4 mL glass vial. The vial was sealed and heated in an isothermal oven at 100° C. and allowed to react solvothermally for 48 h. The product was in the form of cubic shaped brown single crystals. PXRD was checked, it matches the simulated MOF-5 structure (FIG. 11).

Figure 12:
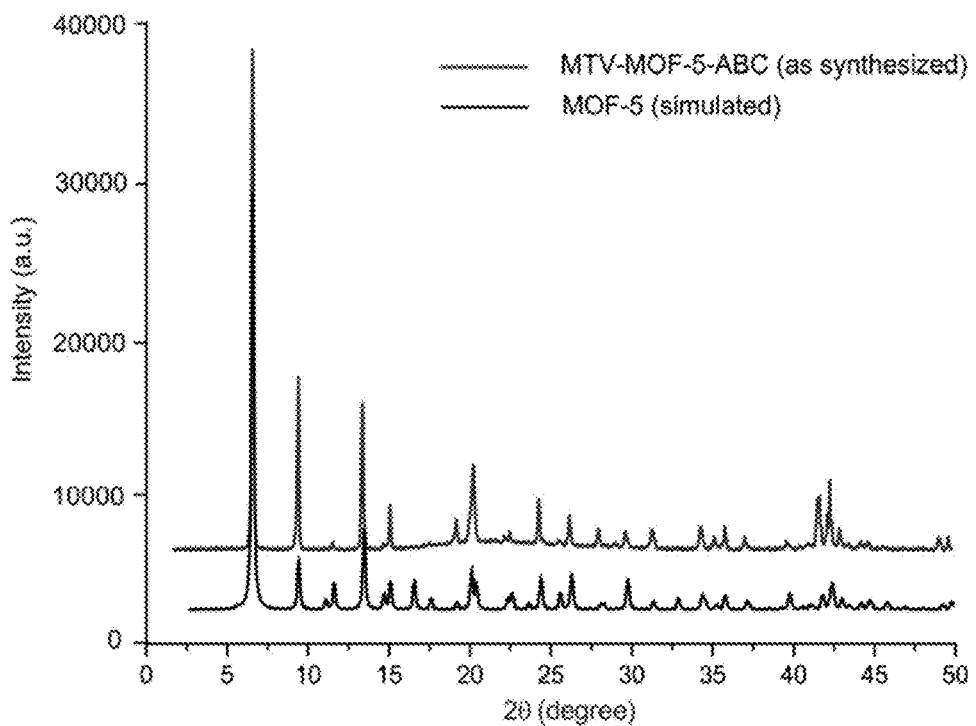
FIG. 12 shows a comparison of the experimental PXRD pattern of as-prepared mvMOF-5-ABC (top) with the simulated MOF-5 diffraction pattern (bottom). The very high degree of correspondence between the patterns indicates that the bulk material has the same topology as MOF-5.

¹H NMR of the digested mvMOF-5-EI crystals (400 MHz, DMSO-d6). NO₂-BDCH₂ δ: 7.92 (d, 1H), 8.25 (d, 1H), 8.35 (s, 1H). (C₇H₇O)₂-BDCH₂ δ: 5.12 (s, 4H), 7.25-7.44 (m, 12H). Molar ratio based on integration of the peaks: NO₂-BDC:(C₇H₇O)₂-BDC=0.20:1.

mvMOF-5-ABC, $Zn_4O(BDC)_{1.90}(NH_2\text{-BDC})_{0.11}(\text{Br-BDC})_{0.99}$:

0.133 mL of BDCH₂ stock solution (0.10 M, 1.33×10⁻⁵ mol), 0.133 mL of NH₂-BDCH₂ stock solution (0.10 M, 1.33×10⁻⁵ mol), 0.133 mL of Br-BDCH₂ stock solution (0.10 M, 1.33×10⁻⁵ mol), 0.40 mL of Zn(NO₃)₂.4H₂O stock solution (0.30 M, 1.2×10⁻⁴ mol) and 1.20 mL of DEF were added in sequence in to a 4 mL glass vial. The vial was sealed and heated in an isothermal oven at 100° C. and allowed to react solvothermally for 48 h. The product was in the form of cubic shaped brown single crystals. PXRD was checked, it matches the simulated MOF-5 structure (FIG. 12).

Figure 13:
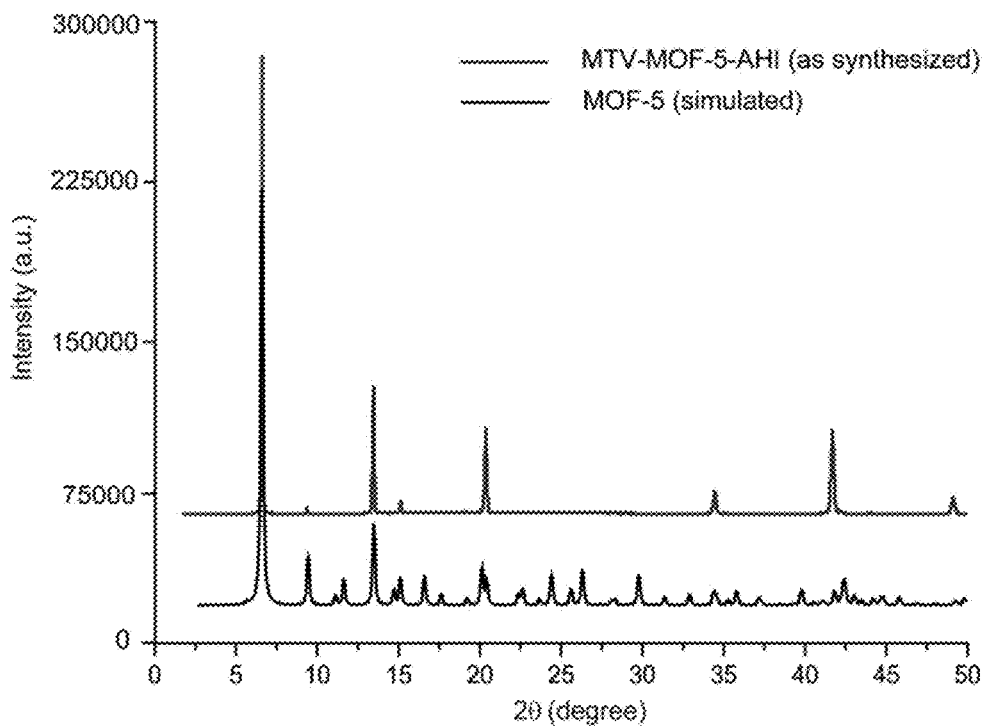
FIG. 13 shows a comparison of the experimental PXRD pattern of as-prepared mvMOF-5-AHI (top) with the simulated MOF-5 diffraction pattern (bottom). The very high degree of correspondence between the patterns indicates that the bulk material has the same topology as MOF-5.

¹H NMR of the digested mvMOF-5-ABC crystals (400 MHz, DMSO-d6). BDCH₂ δ: 8.00 (s, 4H). NH₂-BDCH₂ δ: 7.03 (d, 1H), 7.40 (d, 1H), 7.38 (s, 1H). Br-BDCH₂ δ: 7.78 (d, 1H), 7.94 (d, 1H), 8.10 (s, 1H). Molar ratio based on integration of the peaks: BDC:NH₂-BDC:Br-BDC=1:0.052:0.52.

mvMOF-5-AHI, $Zn_4O(BDC)_{1.52}((C_3H_5O)_2\text{-BDC})_{0.73}((C_7H_7O)_2\text{-BDC})_{0.75}$:

0.133 mL of BDCH₂ stock solution (0.10 M, 1.33×10⁻⁵ mol), 0.133 mL of (C₃H₅O)₂-BDCH₂ stock solution (0.10 M, 1.33×10⁻⁵ mol), 0.133 mL of (C₇H₇O)₂-BDCH₂ stock solution (0.10 M, 1.33×10⁻⁵ mol), 0.40 mL of Zn(NO₃)₂.4H₂O stock solution (0.30 M, 1.2×10⁻⁴ mol) and 1.20 mL of DEF were added in sequence in to a 4 mL glass vial. The vial was sealed and heated in an isothermal oven at 100° C. and allowed to react solvothermally for 24 h. The product was in the form of cubic shaped brown single crystals. PXRD was checked, it matches the simulated MOF-5 structure (FIG. 13).

Figure 14:
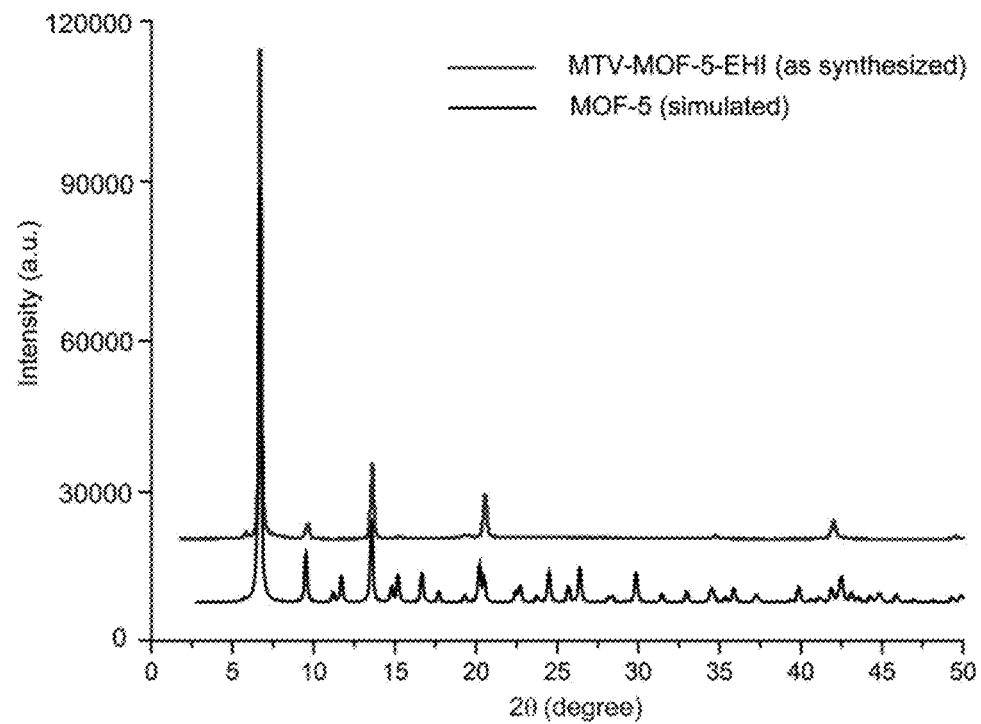
FIG. 14 shows a comparison of the experimental PXRD pattern of as-prepared mvMOF-5-EHI (top) with the simulated MOF-5 diffraction pattern (bottom). The very high degree of correspondence between the patterns indicates that the bulk material has the same topology as MOF-5.

¹H NMR of the digested mvMOF-5-AHI crystals (400 MHz, DMSO-d6). BDCH₂ δ: 8.00 (s, 4H). (C₃H₅O)₂-BDCH₂ δ: 4.55 (d, 4H), 5.20 (d, 2H), 5.38 (d, 2H), 5.93-6.00 (m, 2H). (C₇H₇O)₂-BDCH₂ δ: 5.12 (s, 4H), 7.26-7.44 (m, 12H). Molar ratio based on integration of the peaks: BDC:(C₃H₅O)₂-BDC:(C₇H₇O)₂-BDC=1:0.48:0.50.

mvMOF-5-EHI, $Zn_4O(NO_2\text{-BDC})_{1.19}((C_3H_5O)_2\text{-BDC})_{1.07}((C_7H_7O)_2\text{-BDC})_{0.74}$:

0.133 mL of (C₇H₇O)₂-BDCH₂ stock solution (0.10 M, 1.33×10⁻⁵ mol), 0.133 mL of NO₂-BDCH₂ stock solution (0.10 M, 1.33×10⁻⁵ mol), 0.133 mL of (C₃H₅O)₂-BDCH₂ stock solution (0.10 M, 1.33×10⁻⁵ mol), 0.40 mL of Zn(NO₃)₂.4H₂O stock solution (0.30 M, 1.2×10⁻⁴ mol) and 1.20 mL of DEF were added in sequence in to a 4 mL glass vial. The vial was sealed and heated in an isothermal oven at 100° C. and allowed to react solvothermally for 24 h. The product was in the form of cubic shaped brown single crystals. PXRD was checked, it matches the simulated MOF-5 structure (FIG. 14).

Figure 15:
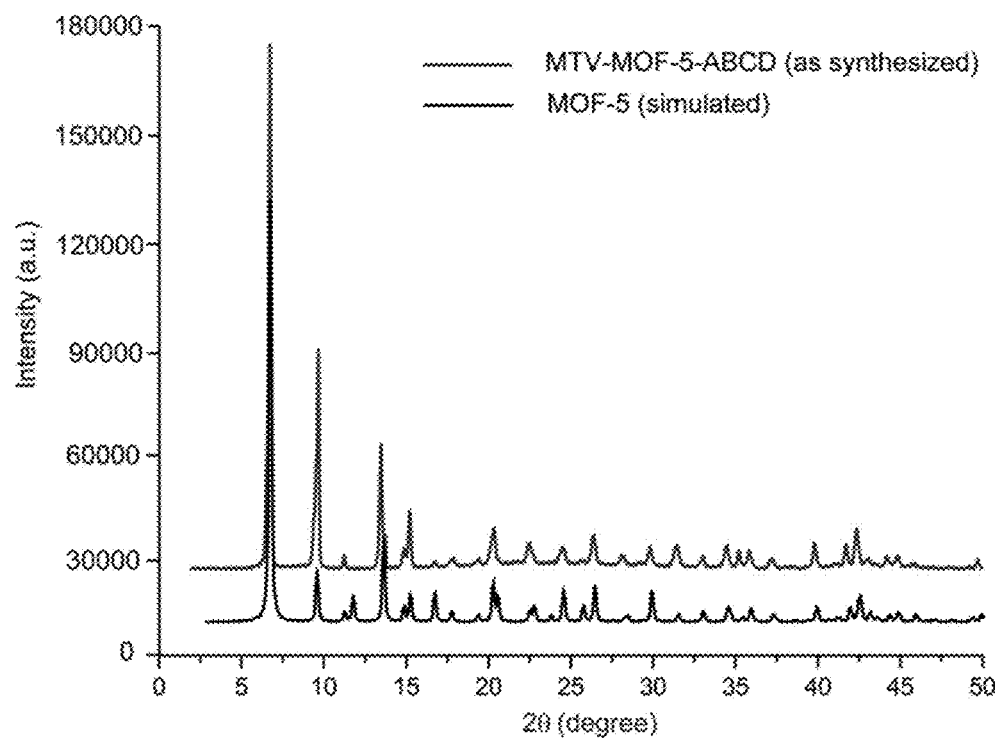
FIG. 15 shows a comparison of the experimental PXRD pattern of as-prepared mvMOF-5-ABCD (top) with the simulated MOF-5 diffraction pattern (bottom). The very high degree of correspondence between the patterns indicates that the bulk material has the same topology as MOF-5.

¹H NMR of the digested mvMOF-5-EHI crystals (400 MHz, DMSO-d6). NO₂-BDCH₂ δ: 7.93 (d, 1H), 8.25 (d, 1H), 8.35 (s, 1H). (C₃H₅O)₂-BDCH₂ δ: 4.55 (d, 4H), 5.20 (d, 2H), 5.38 (d, 2H), 5.93-6.00 (m, 2H). (C₇H₇O)₂-BDCH₂ δ: 5.12 (s, 4H), 7.26-7.44 (m, 12H). Molar ratio based on integration of the peaks: NO₂-BDC:(C₃H₅O)₂-BDC:(C₇H₇O)₂-BDC=1:0.89:0.62.

mvMOF-5-ABCD, $Zn_4O(BDC)_{1.44}(NH_2\text{-BDC})_{0.18}(\text{Br-BDC})_{0.81}((Cl)_2\text{-BDC})_{0.57}$:

0.10 mL of BDCH₂ stock solution (0.10 M, 1.0×10⁻⁵ mol), 0.10 mL of NH₂-BDCH₂ stock solution (0.10 M, 1.0×10⁻⁵ mol), 0.10 mL of Br-BDCH₂ stock solution (0.10 M, 1.0×10⁻⁵ mol), 0.10 mL of (Cl)₂-BDCH₂ stock solution (0.10 M, 1.0×10⁻⁵ mol), 0.40 mL of Zn(NO₃)₂.4H₂O stock solution (0.30 M, 1.2×10⁻⁴ mol) and 1.20 mL of DEF were added in sequence in to a 4 mL glass vial. The vial was sealed and heated in an isothermal oven at 100° C. and allowed to react solvothermally for 48 h. The product was in the form of cubic shaped dark brown single crystals. PXRD was checked, it matches the simulated MOF-5 structure (FIG. 15).

Figure 16:
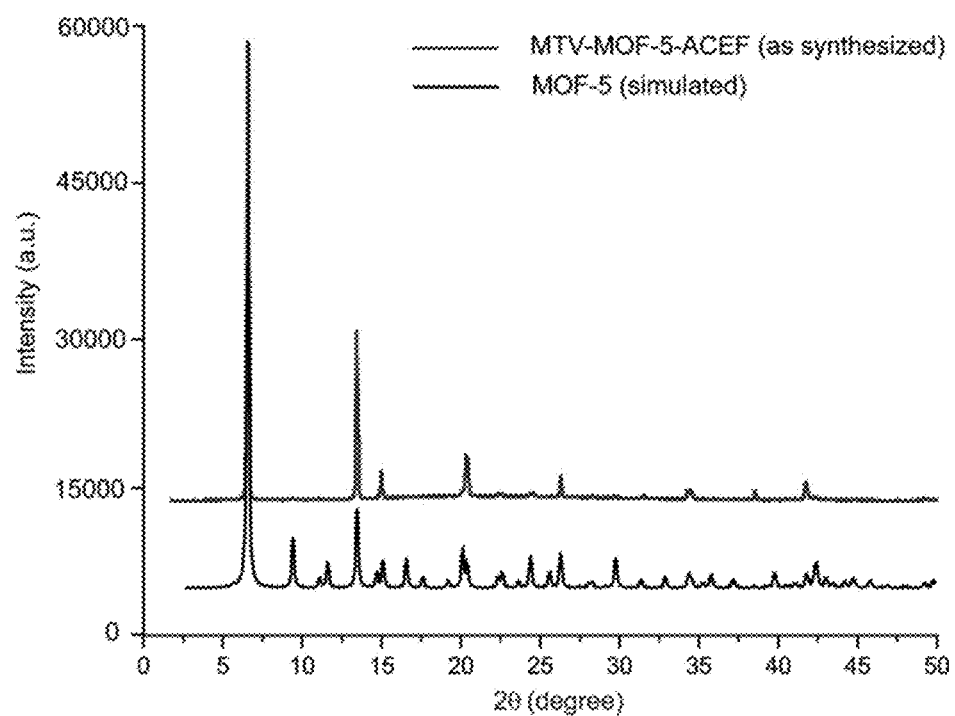
FIG. 16 shows a comparison of the experimental PXRD pattern of as-prepared mvMOF-5-ACEF (top) with the simulated MOF-5 diffraction pattern (bottom). The very high degree of correspondence between the patterns indicates that the bulk material has the same topology as MOF-5.

¹H NMR of the digested mvMOF-5-ABCD crystals (400 MHz, DMSO-d6). BDCH₂ δ: 8.00 (s, 4H). NH₂-BDCH₂ δ: 7.03 (d, 1H), 7.40 (d, 1H), 7.38 (s, 1H). Br-BDCH₂ δ: 7.78 (d, 1H), 7.94 (d, 1H), 8.10 (s, 1H). (Cl)₂-BDCH₂ δ: 7.90 (s, 2H). Molar ratio based on integration of the peaks: BDC:NH₂-BDC:Br-BDC:(Cl)₂-BDC=1:0.12:0.56:0.40.

mvMOF-5-ACEF, $Zn_4O((BDC)_{1.29}(\text{Br-BDC})_{0.63}(NO_2\text{-BDC})_{0.28}((CH_3)_2\text{-BDC})_{0.80}$:

0.10 mL of BDCH₂ stock solution (0.10 M, 1.0×10⁻⁵ mol), 0.10 mL of Br-BDCH₂ stock solution (0.10 M, 1.0×10⁻⁵ mol), 0.10 mL of NO₂-BDCH₂ stock solution (0.10 M, 1.0×10⁻⁵ mol), 0.10 mL of (CH₃)₂-BDCH₂ stock solution (0.10 M, 1.0×10⁻⁵ mol), 0.40 mL of Zn(NO₃)₂.4H₂O stock solution (0.30 M, 1.2×10⁻⁴ mol) and 1.20 mL of DEF were added in sequence in to a 4 mL glass vial. The vial was sealed and heated in an isothermal oven at 100° C. and allowed to react solvothermally for 24 h. The product was in the form of cubic shaped dark brown single crystals. PXRD was checked, it matches the simulated MOF-5 structure (FIG. 16).

Figure 17:
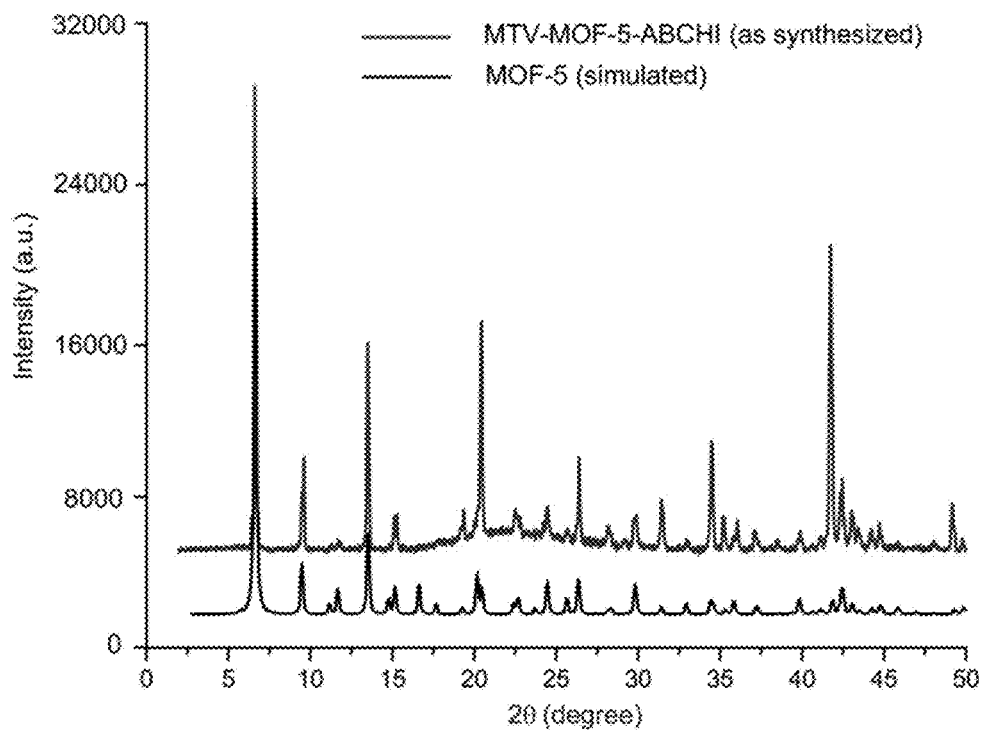
FIG. 17 shows a comparison of the experimental PXRD pattern of as-prepared mvMOF-5-ABCHI (top) with the simulated MOF-5 diffraction pattern (bottom). The very high degree of correspondence between the patterns indicates that the bulk material has the same topology as MOF-5.

¹H NMR of the digested mvMOF-5-ACEF crystals (400 MHz, DMSO-d6). BDCH₂ δ: 8.00 (s, 4H). Br-BDCH₂ δ: 7.78 (d, 1H), 7.94 (d, 1H), 8.10 (s, 1H). NO₂-BDCH₂ δ: 7.92 (d, 1H), 8.25 (d, 1H), 8.35 (s, 1H). (CH₃)₂-BDCH₂ δ: 2.43 (s, 6H), 7.64 (s, 2H). Molar ratio based on integration of the peaks: BDC:Br-BDC:(CH₃)₂-BDC:NO₂-BDC=1:0.49:0.62:0.22.

mvMOF-5-ABCHI, $Zn_4O(BDC)_{1.38}(NH_2\text{-BDC})_{0.03}(\text{Br-BDC})_{0.30}((C_3H_5O)_2\text{-BDC})_{0.86}((C_7H_7O)_2\text{-BDC})_{0.43}$:

80 μL of BDCH₂ stock solution (0.10 M, 8.0×10⁻⁶ mol), 80 μL of NH₂-BDCH₂ stock solution (0.10 M, 8.0×10⁻⁶ mol), 80 μL of Br-BDCH₂ stock solution (0.10 M, 8.0×10⁻⁶ mol), 80 μL of (C₃H₅O)₂-BDCH₂ stock solution (0.10 M, 8.0×10⁻⁶ mol), 80 μL of (C₇H₇O)₂-BDCH₂ stock solution (0.10 M, 8.0×10⁻⁶ mol), 0.40 mL of Zn(NO₃)₂.4H₂O stock solution (0.30 M, 1.2×10⁻⁴ mol) and 1.20 mL of DEF were added in sequence in to a 4 mL glass vial. The vial was sealed and heated in an isothermal oven at 100° C. and allowed to react solvothermally for 48 h. The product was in the form of cubic shaped dark brown single crystals. PXRD was checked, it matches the simulated MOF-5 structure (FIG. 17).

Figure 18:
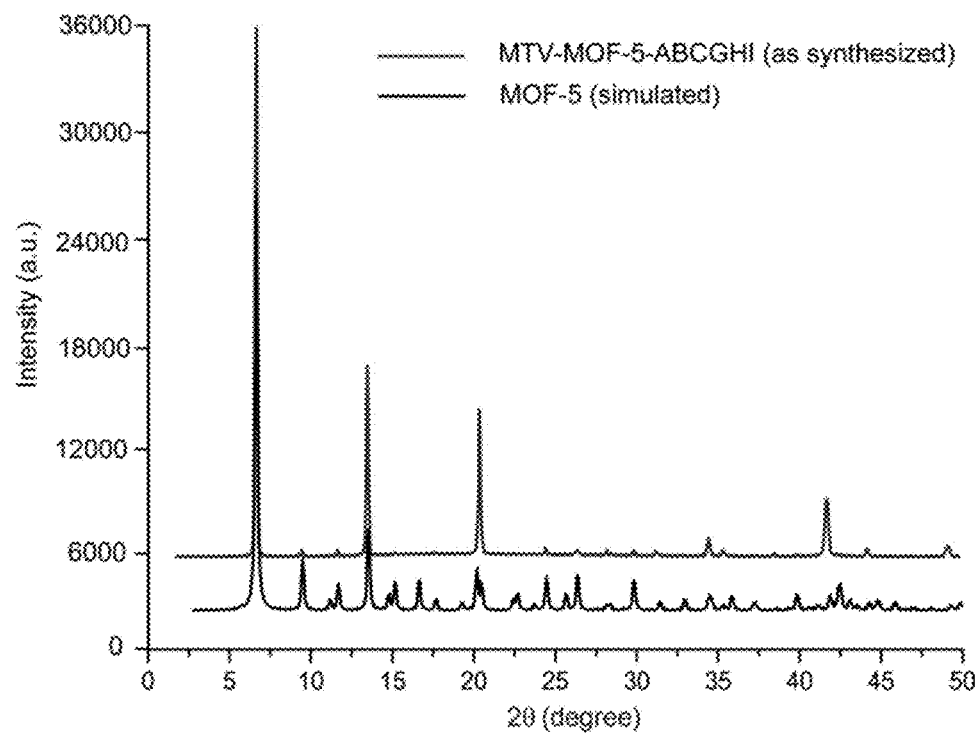
FIG. 18 shows a comparison of the experimental PXRD pattern of as-prepared mvMOF-5-ABCGHI (top) with the simulated MOF-5 diffraction pattern (bottom). The very high degree of correspondence between the patterns indicates that the bulk material has the same topology as MOF-5.

¹H NMR of the digested mvMOF-5-ABCHI crystals (400 MHz, DMSO-d6). BDCH₂ δ: 8.00 (s, 4H). NH₂-BDCH₂. δ: 7.03 (d, 1H). Br-BDCH₂ δ: 7.78 (d, 1H), 7.94 (d, 1H), 8.10 (s, 1H). (C₃H₅O)₂-BDCH₂ δ: 4.54 (d, 4H), 5.19 (d, 2H), 5.40 (d, 2H), 5.94-6.01 (m, 2H). (C₇H₇O)₂-BDCH₂ δ: 5.12 (s, 4H), 7.25-7.44 (m, 12H). Molar ratio based on integration of the peaks: BDC:NH$_2$-BDC:Br-BDC:(C$_3$H$_5$O)$_2$-BDC:(C$_7$H$_7$O)$_2$-BDC=1:0.017:0.22:0.62:0.32.

mvMOF-5-ABCGHI, Zn$_4$O(BDC)$_{0.72}$(NH$_2$-BDC)$_{0.08}$(Br-BDC)$_{0.63}$(C$_4$H$_4$-BDC)$_{0.48}$((C$_3$H$_5$O)$_2$-BDC)$_{0.52}$((C$_7$H$_7$O)$_2$-BDC)$_{0.57}$:

67 µL of BDCH$_2$ stock solution (0.10 M, 6.7×10$^{-6}$ mol), 67 µL of NH$_2$-BDCH$_2$ stock solution (0.10 M, 6.7×10$^{-6}$ mol), 67 µL of Br-BDCH$_2$ stock solution (0.10 M, 6.7×10$^{-6}$ mol), 267 µL of C$_4$H$_4$-BDCH$_2$ stock solution (0.10 M, 6.7×10$^{-6}$ mol), 67 µL of (C$_3$H$_5$O)$_2$-BDCH$_2$ stock solution (0.10 M, 6.7×10$^{-6}$ mol), 67 µL of (C$_7$H$_7$O)$_2$-BDCH$_2$ stock solution (0.10 M, 6.7×10$^{-6}$ mol), 0.40 mL of Zn(NO$_3$)$_2$.4H$_2$O stock solution (0.30 M, 1.2×10$^{-4}$ mol) and 1.0 mL of DEF were added in sequence in to a 4 mL glass vial. The vial was sealed and heated in an isothermal oven at 100° C. and allowed to react solvothermally for 48 h. The product was in the form of cubic shaped dark brown single crystals. PXRD was checked, it matches the simulated MOF-5 structure (FIG. 18).

Figure 19:
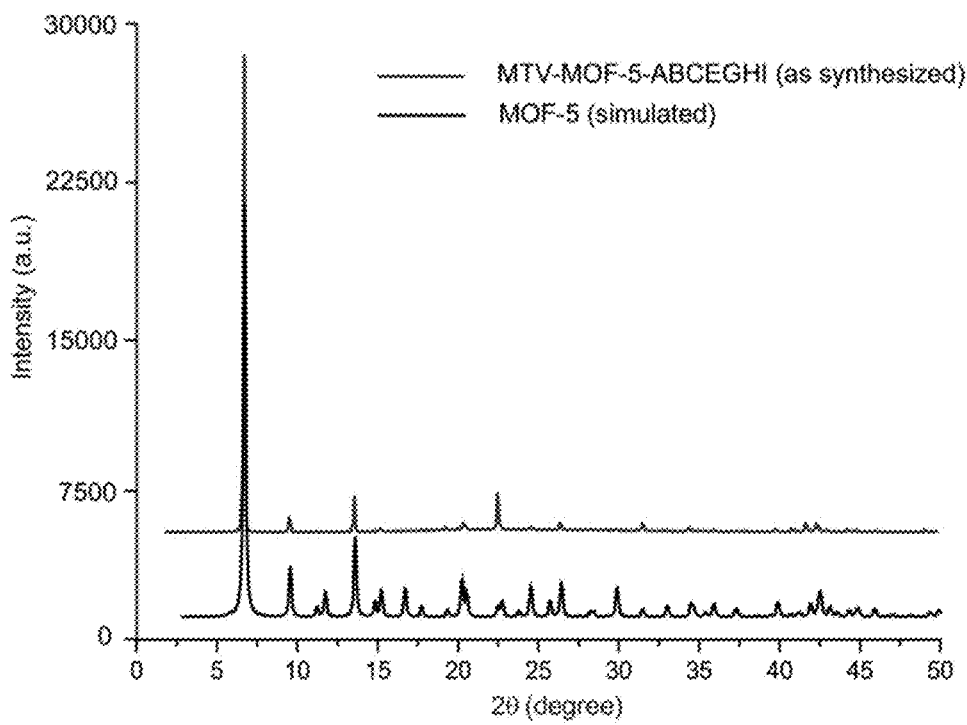
FIG. 19 shows a comparison of the experimental PXRD pattern of as-prepared mvMOF-5-ABCEGHI with the simulated MOF-5 diffraction pattern (bottom). The very high degree of correspondence between the patterns indicates that the bulk material has the same topology as MOF-5.

$^1$H NMR of the digested mvMOF-5-ABCGHI crystals (400 MHz, DMSO-d6). BDCH$_2$ δ: 8.00 (s, 4H). NH$_2$-BDCH$_2$ δ: 7.03 (d, 1H). Br-BDCH$_2$ δ: 7.78 (d, 1H), 7.94 (d, 1H), 8.10 (s, 1H). C$_4$H$_4$-BDCH$_2$ δ: 7.64-7.68 (m, 2H), 8.05 (s, 2H), 8.70-8.74 (m, 2H). (C$_3$H$_5$O)$_2$-BDCH$_2$ δ: 4.54 (d, 4H), 5.19 (d, 2H), 5.40 (d, 2H), 5.94-6.01 (m, 2H). (C$_7$H$_7$O)$_2$-BDCH$_2$ δ: 5.12 (s, 4H), 7.25-7.44 (m, 12H). Molar ratio based on integration of the peaks: BDC:NH$_2$-BDC:Br-BDC:C$_4$H$_4$-BDC:(C$_3$H$_5$O)$_2$-BDC:(C$_7$H$_7$O)$_2$-BDC=1:0.093:0.87:0.67:0.73:0.80.

mvMOF-5-ABCEGHI, Zn$_4$O (BDC)$_{0.57}$(NH$_2$-BDC)$_{0.05}$(Br-BDC)$_{0.57}$(NO$_2$-BDC)0.39(C$_4$H$_4$-BDC)$_{0.44}$((C$_3$H$_5$O)$_2$-BDC)$_{0.42}$((C$_7$H$_7$O)$_2$-BDC)$_{0.56}$:

57 µL of BDCH$_2$ stock solution (0.10 M, 5.7×10$^{-6}$ mol), 57 µL of NH$_2$-BDCH$_2$ stock solution (0.10 M, 5.7×10$^{-6}$ mol), 57 µL of Br-BDCH$_2$ stock solution (0.10 M, 5.7×10$^{-6}$ mol), 57 µL of NO$_2$-BDCH$_2$ stock solution (0.10 M, 5.7×10$^{-6}$ mol), 228 µL of C$_4$H$_4$-BDCH$_2$ stock solution (0.10 M, 5.7×10$^{-6}$ mol), 57 µL of (C$_3$H$_5$O)$_2$-BDCH$_2$ stock solution (0.10 M, 5.7×10$^{-6}$ mol), 57 µL of (C$_7$H$_7$O)$_2$-BDCH$_2$ stock solution (0.10 M, 5.7×10$^{-6}$ mol), 0.40 mL of Zn(NO$_3$)$_2$.4H$_2$O stock solution (0.30 M, 1.2×10$^{-4}$ mol) and 1.03 mL of DEF were added in sequence in to a 4 mL glass vial. The vial was sealed and heated in an isothermal oven at 100° C. and allowed to react solvothermally for 48 h. The product was in the form of cubic shaped dark brown single crystals. PXRD was checked, it matches the simulated MOF-5 structure (FIG. 19).

Figure 20:
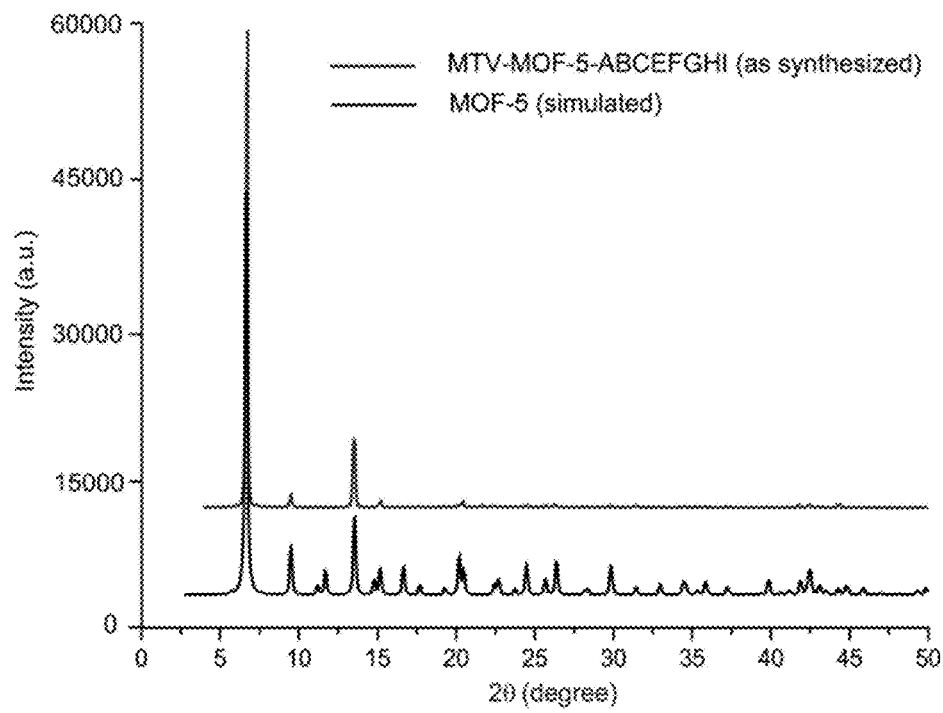
FIG. 20 shows a comparison of the experimental PXRD pattern of as-prepared mvMOF-5-ABCEFGHI (top) with the simulated MOF-5 diffraction pattern (bottom). The very high degree of correspondence between the patterns indicates that the bulk material has the same topology as MOF-5.
Figure 21:
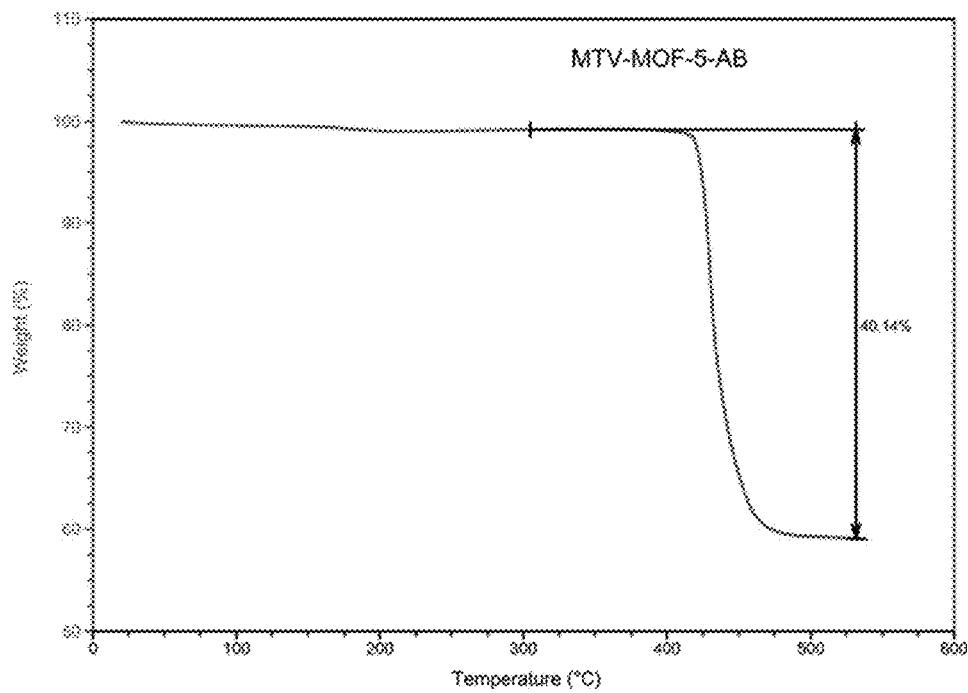
FIG. 21 is a TGA trace of activated mvMOF-5-AB.
Figure 22:
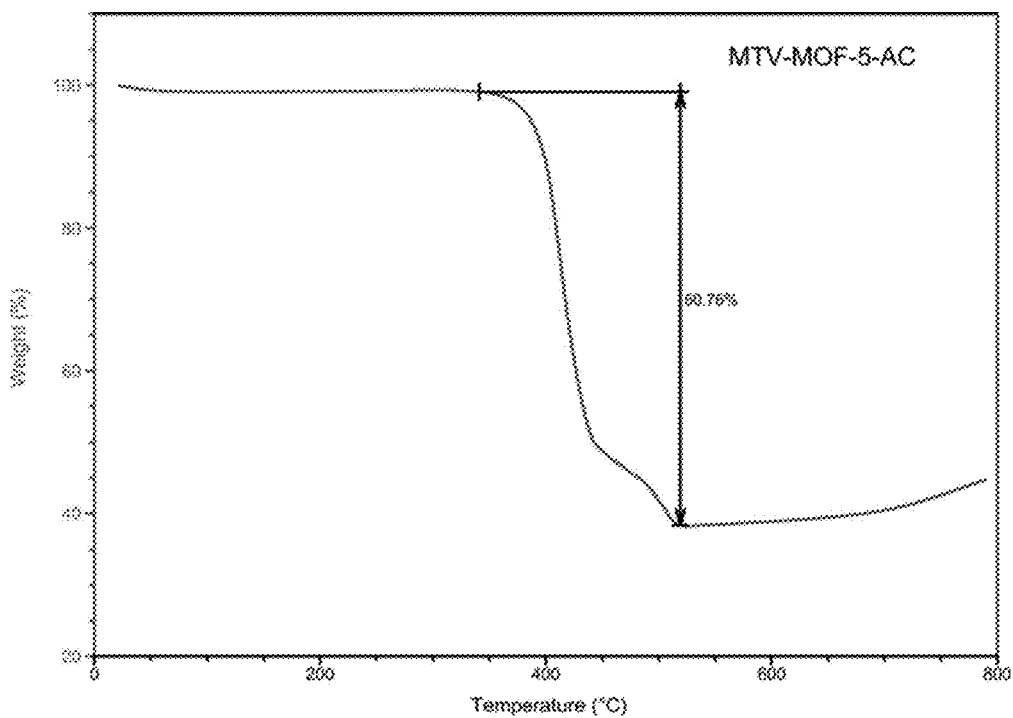
FIG. 22 is a TGA trace of activated mvMOF-5-AC.
Figure 23:
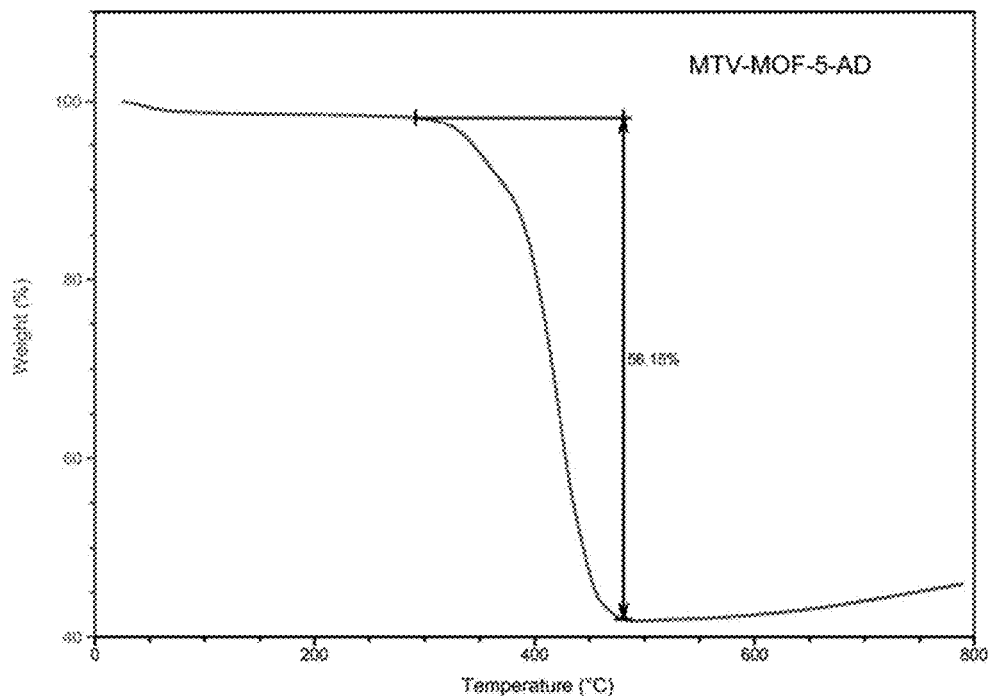
FIG. 23 is a TGA trace of activated mvMOF-5-AD.

$^1$H NMR of the digested mvMOF-5-ABCEGHI crystals (400 MHz, DMSO-d6). BDCH$_2$ δ: 8.00 (s, 4H). NH$_2$-BDCH$_2$ δ: 7.03 (d, 1H). Br-BDCH$_2$ δ: 7.78 (d, 1H), 7.94 (d, 1H), 8.10 (s, 1H). NO$_2$-BDCH$_2$ δ: 7.92 (d, 1H), 8.25 (d, 1H), 8.35 (s, 1H). C$_4$H$_4$-BDCH$_2$ δ: 7.64-7.68 (m, 2H), 8.05 (s, 2H), 8.70-8.74 (m, 2H). (C$_3$H$_5$O)$_2$-BDCH$_2$ δ: 4.54 (d, 4H), 5.19 (d, 2H), 5.40 (d, 2H), 5.94-6.01 (m, 2H). (C$_7$H$_7$O)$_2$-BDCH$_2$ δ: 5.12 (s, 4H), 7.25-7.44 (m, 12H). Molar ratio based on integration of the peaks: BDC:NH$_2$-BDC:Br-BDC:NO$_2$-BDC:C$_4$H$_4$-BDC:(C$_3$H$_5$O)$_2$-BDC:(C$_7$H$_7$O)$_2$-BDC=1:0.077:1:0.69:0.77:0.73:0.96.

mvMOF-5-ABCEFGHI, Zn$_4$O (BDC)$_{0.70}$(NH$_2$-BDC)$_{0.011}$(Br-BDC)$_{0.39}$(NO$_2$-BDC)$_{0.21}$((CH$_3$)$_2$-BDC)$_{0.46}$(C$_4$H$_4$-BDC)$_{0.39}$((C$_3$H$_5$O)$_2$-BDC)$_{0.35}$((C$_7$H$_7$O)$_2$-BDC)$_{0.39}$:

50 µL of BDCH$_2$ stock solution (0.10 M, 5.0×10$^{-6}$ mol), 50 µL of NH$_2$-BDCH$_2$ stock solution (0.10 M, 5.0×10$^{-6}$ mol), 50 µL of Br-BDCH$_2$ stock solution (0.10 M, 5.0×10$^{-6}$ mol), 50 µL of NO$_2$-BDCH$_2$ stock solution (0.10 M, 5.0×10$^{-6}$ mol), 50 µL of (CH$_3$)$_2$-BDCH$_2$ stock solution (0.10 M, 5.0×10$^{-6}$ mol), 200 µL of C$_4$H$_4$-BDCH$_2$ stock solution (0.10 M, 5.0×10$^{-6}$ mol), 50 µL of (C$_3$H$_5$O)$_2$-BDCH$_2$ stock solution (0.10 M, 5.0×10$^{-6}$ mol), 50 µL of (C$_7$H$_7$O)$_2$-BDCH$_2$ stock solution (0.10 M, 5.0×10$^{-6}$ mol), 0.40 mL of Zn(NO$_3$)$_2$.4H$_2$O stock solution (0.30 M, 1.2×10$^{-4}$ mol) and 1.05 mL of DEF were added in sequence in to a 4 mL glass vial. The vial was sealed and heated in an isothermal oven at 100° C. and allowed to react solvothermally for 48 h. The product was in the form of cubic shaped dark brown single crystals. PXRD was checked, it matches the simulated MOF-5 structure (FIG. 20).

$^1$H NMR of the digested mvMOF-5-ABCEFGHI crystals (400 MHz, DMSO-d6). BDCH$_2$ δ: 8.00 (s, 4H). NH$_2$-BDCH$_2$ δ: 7.03 (d, 1H). Br-BDCH$_2$ δ: 7.78 (d, 1H), 7.94 (d, 1H), 8.10 (s, 1H). NO$_2$-BDCH$_2$ δ: 7.92 (d, 1H), 8.25 (d, 1H), 8.35 (s, 1H). (CH$_3$)$_2$-BDCH$_2$ δ: 2.43 (s, 6H), 7.64 (s, 2H). C$_4$H$_4$-BDCH$_2$ δ: 7.64-7.68 (m, 2H), 8.05 (s, 2H), 8.70-8.74 (m, 2H). (C$_3$H$_5$O)$_2$-BDCH$_2$ δ: 4.54 (d, 4H), 5.19 (d, 2H), 5.40 (d, 2H), 5.94-6.01 (m, 2H). (C$_7$H$_7$O)$_2$-BDCH$_2$ δ: 5.12 (s, 4H), 7.25-7.44 (m, 12H). Molar ratio based on integration of the peaks: BDC:NH$_2$-BDC:Br-BDC:(CH$_3$)$_2$-BDC:NO$_2$-BDC:C$_4$H$_4$-BDC:(C$_3$H$_5$O)$_2$-BDC:(C$_7$H$_7$O)$_2$-BDC=1:0.14:0.56:0.29:0.67:0.56:0.48:0.56.

All compounds containing two, three or four different links, and mvMOF-5-ABCEFGHI were scaled up to gram scale with the same concentration as described above. PXRD of scaled-up sample are identical with the small scale samples. In addition, the bulk homogeneity of scaled-up sample was checked by solution $^1$H NMR of randomly selected crystals, and showed identical link ratios in each compound.

Thermalgravimetry.

All samples were run on a TA Instruments Q-500 series thermal gravimetric analyzer with samples held in platinum pans in a continuous air flow atmosphere. Samples were heated at a constant rate of 5° C./min during all TGA experiments.

Due to the loss of dangling double bond and benzene ring in the links, mvMOFs containing link H and link I will lose weight gradually from 200° C., followed by a steep drop at 400° C. All other mvMOFs will have not lose weight until 400° C.

Solid State $^{13}$C MAS NMR of Activated mvMOFs.

High resolution solid-state nuclear magnetic resonance (NMR) spectra were recorded at ambient temperature on a Bruker DSX-300 spectrometer using a standard Bruker magic angle spinning (MAS) probe with 4 mm (outside diameter) zirconia rotors. Cross-polarization with MAS (CP/MAS) was used to acquire $^{13}$C data at 75.47 MHz. The $^1$H and $^{13}$C ninety-degree pulse widths were both 4 µs. The CP contact time was varied of 1.5 ms, and 5 ms. High power two-pulse phase modulation (TPPM) 1H decoupling was applied during data acquisition. The decoupling frequency corresponded to 72 kHz. The MAS sample spinning rate was 10 kHz. Recycle delays for (CP/MAS) between scans varied between 3 and 20 s, depending upon the compound as determined by observing no apparent loss in the $^{13}$C signal intensity from one scan to the next. The $^{13}$C chemical shifts are given relative to tetramethylsilane as zero ppm, calibrated using the methylene carbon signal of adamantane assigned to 37.77 ppm as a secondary reference were listed in Table 2.

Control experiment of $^{13}$C CP/MAS NMR on link mixture of the same ratio as in mvMOF-5-AB, -ABCD, and -ABCEF-GHI was checked, there is a significant shift of the carbonyl carbon, from 172 to 174 ppm comparing to the experiment on mvMOFs. This demonstrates that all links in these three mvMOFs are chemically bonded to zinc cluster. In addition, $^{13}$C spectrum of the static sample was acquired using CP/MAS method was checked to detect mobile guest molecules. In this experiment, recycle delay was set to 20 s to allow enough relaxation between scans. No detectable carbon signals were found which confirm the clean pore structure of mvMOFs.

Figure 35:
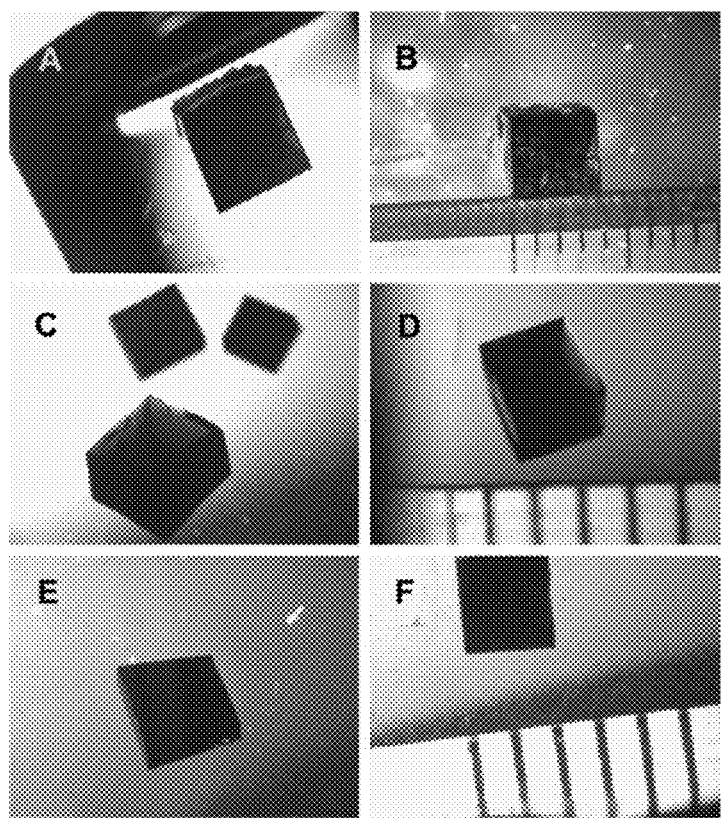
FIG. 35A-F are optical images. (A and B): Optical image of as-synthesized mvMOF-5-AB-lsc. (C and D): Optical image of as-synthesized mvMOF-5-ABCD-lsc. (E and F): Optical image of as-synthesized mvMOF-5-ABCEFGHI-lsc.
Figure 36:
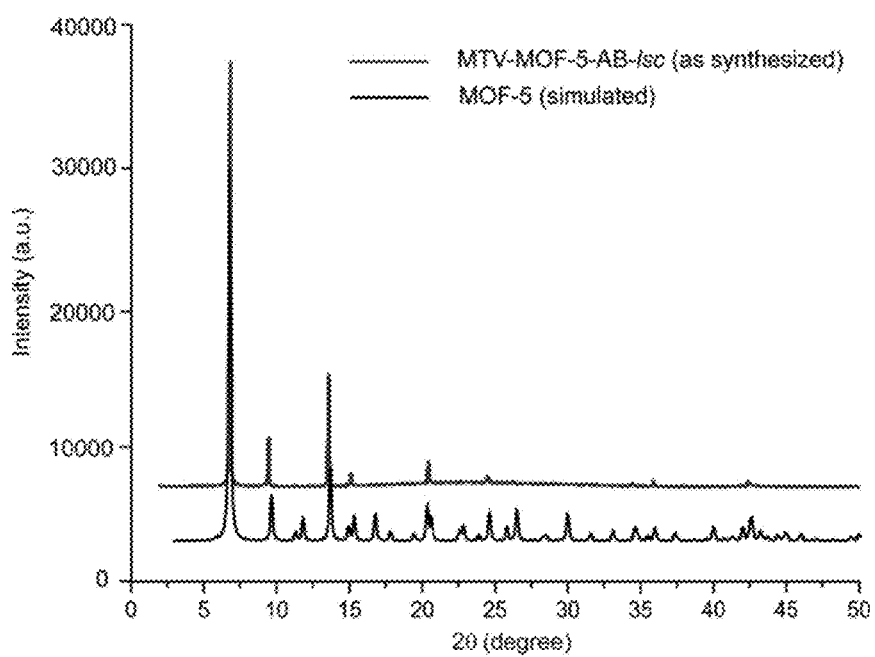
FIG. 36 is a comparison of the experimental PXRD pattern of as-prepared single crystal of mvMOF-5-AB (top) with the simulated MOF-5 diffraction pattern (bottom). The very high degree of correspondence between the patterns indicates that the bulk material has the same topology as MOF-5.
Figure 37:
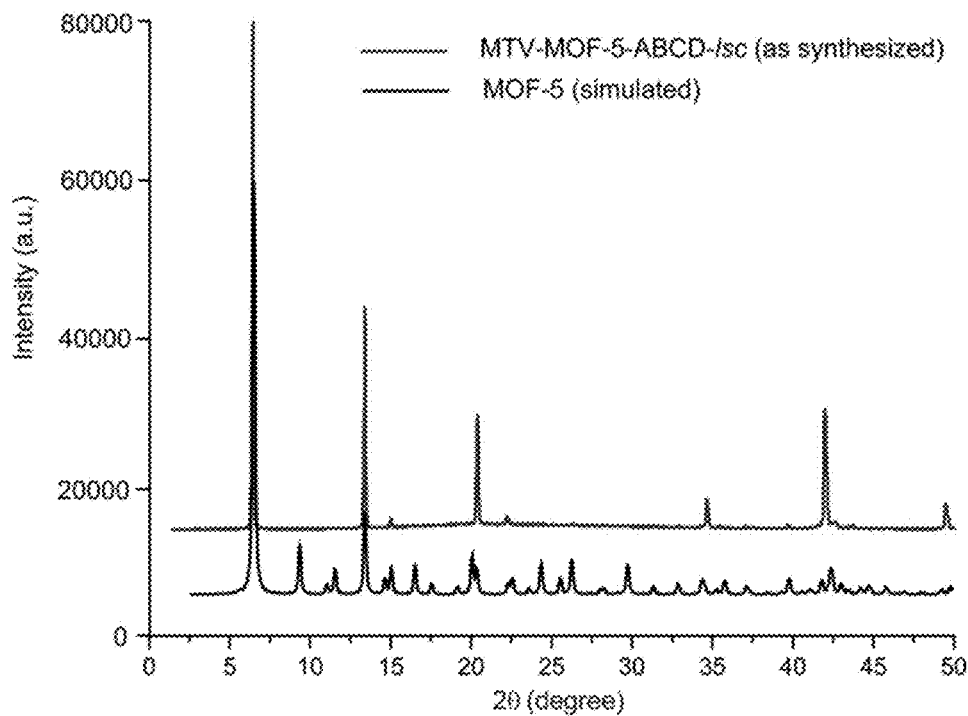
FIG. 37 is a comparison of the experimental PXRD pattern of as-prepared single crystal of mvMOF-5-ABCD (top) with the simulated MOF-5 diffraction pattern (bottom). The very high degree of correspondence between the patterns indicates that the bulk material has the same topology as MOF-5.
Figure 38:
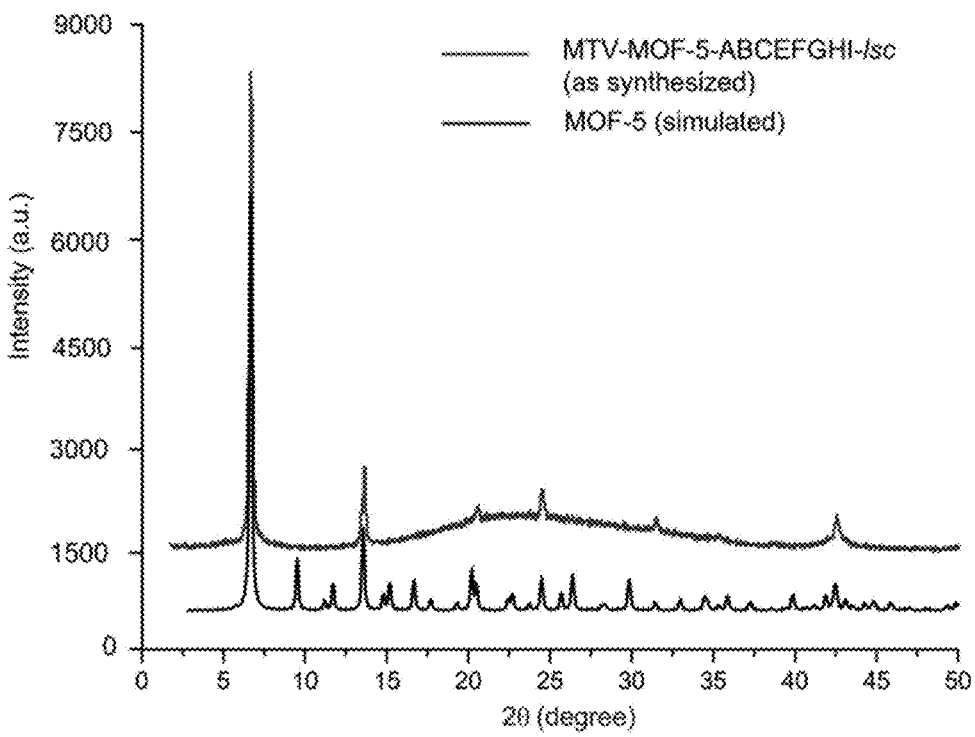
FIG. 38 is a comparison of the experimental PXRD pattern of as-prepared single crystal of mvMOF-5-ABCEFGHI (top) with the simulated MOF-5 diffraction pattern (bottom). The very high degree of correspondence between the patterns indicates that the bulk material has the same topology as MOF-5.
Figure 39:
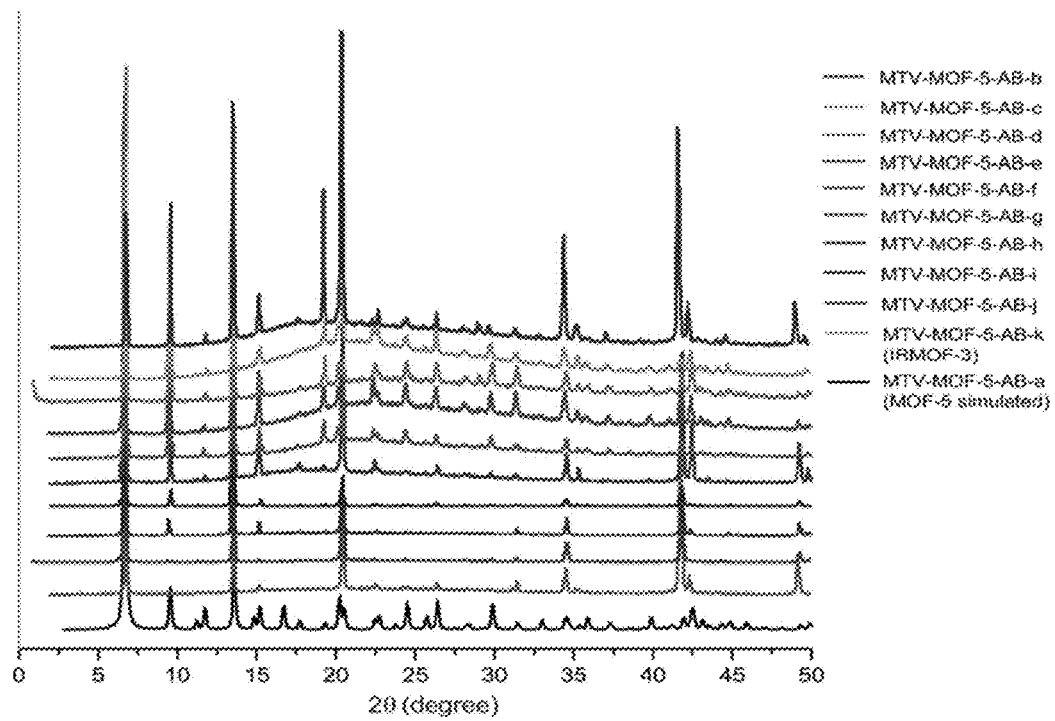
FIG. 39 is a comparison of the experimental PXRD pattern of as-prepared mvMOF-5-AB series (a-k) with the simulated MOF-5 diffraction pattern (black). The very high degree of correspondence between the patterns indicates that the bulk materials all have the same topology as MOF-5.

MOF-5 topology by the coincidence of experimental PXRD pattern with the simulated one and by examination of these crystals under an optical microscope (FIGS. 35 C,D and 37)

TABLE 2

Summary of $^{13}$C CP/MAS NMR of selected mvMOF and their link mixture.

| Compound | Chemical shift δ (ppm) | | | | | | | | | | | | | | | |
|---|---|---|---|---|---|---|---|---|---|---|---|---|---|---|---|---|
| Selected mvMOFs | | | | | | | | | | | | | | | | |
| mvMOF-5-AB | 174.5 | 149.8 | 135.5 | 129. | 118. | 115.6 | | | | | | | | | | |
| mvMOF-5-AC | 174.3 | 135.5 | 131.3 | 128. | 126. | 122.3 | | | | | | | | | | |
| mvMOF-5-AD | 174.4 | 135.4 | 133.0 | 131. | 128. | | | | | | | | | | | |
| mvMOF-5-AE | 174.4 | 151.9 | 135.4 | 128. | 123. | | | | | | | | | | | |
| mvMOF-5-AF | 176.3 | 174.3 | 136.9 | 135. | 133. | 128.6 | 18.7 | | | | | | | | | |
| mvMOF-5-AG | 177.5 | 147.6 | 135.5 | 134. | 131. | 126.3 | 125.2 | | | | | | | | | |
| mvMOF-5-AH | 175.0 | 153.3 | 136.3 | 133. | 129. | 127.9 | 119.7 | 114.2 | 71.4 | | | | | | | |
| mvMOF-5-AI | 174.3 | 152.8 | 135.5 | 119. | 71.5 | | | | | | | | | | | |
| mvMOF-5-EI | 174.3 | 151.9 | 145.4 | 136. | 133. | 126.8 | 126.2 | 118.3 | 70.9 | | | | | | | |
| mvMOF-5-AHI | 174.3 | 152.3 | 135.7 | 132. | 127. | 118.7 | 114.5 | 70.6 | | | | | | | | |
| mvMOF-5-EHI | 174.5 | 152.0 | 136.6 | 132. | 126. | 118.6 | 115.3 | 70.5 | | | | | | | | |
| mvMOF-5-ABCD | 177.2 | 175.2 | 150.3 | 137. | 136. | 133.7 | 132.3 | 129.4 | 127.0 | 123.0 | 118. | 116 | | | | |
| mvMOF-5-ACEF | 177.0 | 174.9 | 151.8 | 136. | 135. | 133.6 | 131.4 | 128.6 | 126.8 | 124.0 | 122. | 18. | | | | |
| mvMOF-5- | 177.3 | 176.4 | 174.4 | 152. | 137. | 135.6 | 133.9 | 132.7 | 131.4 | 126.4 | 125. | 122 | 119 | 116 | 113 | 71 | 70 | 18 |
| Selected Link Mixture | | | | | | | | | | | | | | | | |
| Li | 172 | 150 | 135. | 129 | 118. | 115. | | | | | | | | | | |
| Li | 172 | 150 | 137. | 136 | 133. | 132. | 129. | 126 | 123 | 118. | 115. | | | | | |
| Li | 172 | 152 | 137. | 135 | 134. | 133. | 131. | 126 | 125 | 122. | 119. | 116. | 114 | 72. | 70. | 21 |

Synthesis of Large Single Crystals mvMOF-5-AB-Lsc.

4.20 g Zn(N03)$_2$.4H$_2$O (16.0 mmol), 450 mg BDCH$_2$ (2.7 mmol) and 490 mg NH$_2$-BDCH$_2$ (2.7 mmol) were dissolved in 50 mL DEF in a glass beaker by sonicating the mixture for 15 min. The solution was dispensed evenly into 10 scintillation vials (20-mL size) by using a plastic syringe equipped with a PTFE filter (Whatman, 0.45 μm pore size). The vials were then tightly capped and placed in an isothermal oven. The reactions were stopped after being heated at 85° C. for 72 h. The mother liquor in each vial was decanted while warm and the product was washed with fresh DEF (3×5 mL for each vial). Most of the products were large chunks of inter-grown cubic brown crystals. Occasionally, some large single cubes (size 1.5-4.0 mm) were observed. In a typical batch as described above, 8-13 such crystals could be obtained. The large cubic crystals were confirmed to have MOF-5 topology by the coincidence of experimental PXRD pattern with the simulated one and by examination of these crystals under an optical microscope (FIGS. 35 A, B and 36). The high initial concentration is useful to the formation of large mvMOF single crystals.

Synthesis of Large Single Crystal mvMOF-5-ABCD-lsc.

6.20 g Zn(NO$_3$)$_2$.4H$_2$O (23.5 mmol), 332 mg BDCH$_2$ (2.0 mmol), 362 mg NH$_2$-BDCH$_2$ (2.0 mmol), 490 mg Br-BDCH$_2$ (2.0 mmol), and 470 mg (Cl)$_2$-BDCH$_2$ (2.0 mmol) were dissolved in 50 mL DEF in a glass beaker by sonicating the mixture for 15 min. The solution was dispensed evenly into 10 scintillation vials (20-mL size) by using a plastic syringe equipped with a PTFE filter (Whatman, 0.45 μm pore size). The vials were then tightly capped and placed in an isothermal oven. The reactions were stopped after being heated at 85° C. for 120 h. The mother liquor in each vial was decanted while warm and the product was washed with fresh DEF (3×5 mL for each vial). Most of the products were large chunks of inter-grown brown cubic crystals. Occasionally, some large single cubes (size 1.0-2.0 mm) were observed. In a typical batch as described above, 6-10 such crystals could be obtained. The large cubic crystals were confirmed to have Synthesis of Large Single Crystal mvMOF-5-ABCEF-GHI-lsc.

4.20 g Zn(NO$_3$)$_2$.4H$_2$O (23.5 mmol), 166 mg BDCH$_2$ (1.0 mmol), 181 mg NH$_2$-BDCH$_2$ (1.0 mmol), 245 mg Br-BDCH$_2$ (1.0 mmol), 211 mg NO$_2$-BDCH$_2$ (1.0 mmol), 194 mg (CH$_3$)$_2$-BDCH$_2$ (1.0 mmol), 216 mg C$_4$H$_4$-BDCH$_2$ (1.0 mmol), 278 mg (C$_3$H$_5$O)$_2$-BDCH$_2$ (1.0 mmol), and 374 mg (C$_7$H$_7$O)$_2$-BDCH$_2$ (1.0 mmol) were dissolved in 50 mL DEF in a glass beaker by sonicating the mixture for 15 min. The solution was dispensed evenly into 10 scintillation vials (20-mL size) by using a plastic syringe equipped with a PTFE filter (Whatman, 0.45 μm pore size). The vials were then tightly capped and placed in an isothermal oven. The reactions were stopped after being heated at 85° C. for 7 days. The mother liquor in each vial was decanted while warm and the product was washed with fresh DEF (3×5 mL for each vial). Most of the products were large chunks of inter-grown brown cubic crystals. Occasionally, some large single cubes (size 1.0-2.0 mm) were observed. In a typical batch as described above, 5-6 such crystals could be obtained. The large cubic crystals were confirmed to have MOF-5 topology by the coincidence of experimental PXRD pattern with the simulated one and by examination of these crystals under an optical microscope (FIGS. 35 E, F and 38).

Solvent-Exchange of MVMOF Large Single Crystals.

The suitable crystals were collected in a 20-mL scintillation vial. After DEF solvent was removed as clean as possible by using a pipette, this open vial was placed in a desiccator saturated with chloroform vapor, which slowly condensed into the vial and accumulated to ~5 mm tall in 3 days. The crystals were still completely transparent at this point. After the removal of the accumulated chloroform, the vial was filled with fresh chloroform and capped. The solvent volume was replaced twice after a 1-day and a 2-day immersion respectively, and was allowed to sit for another 2 days. The total time of chloroform-exchange of mvMOF large single crystals were 3 days in desiccator and 5 days on bench.

Ratio of the links within mvMOFs were determined by °H NMR. The results are listed in Table 1.

Synthesis of mvMOF-5-AB Series.

Figure 40:
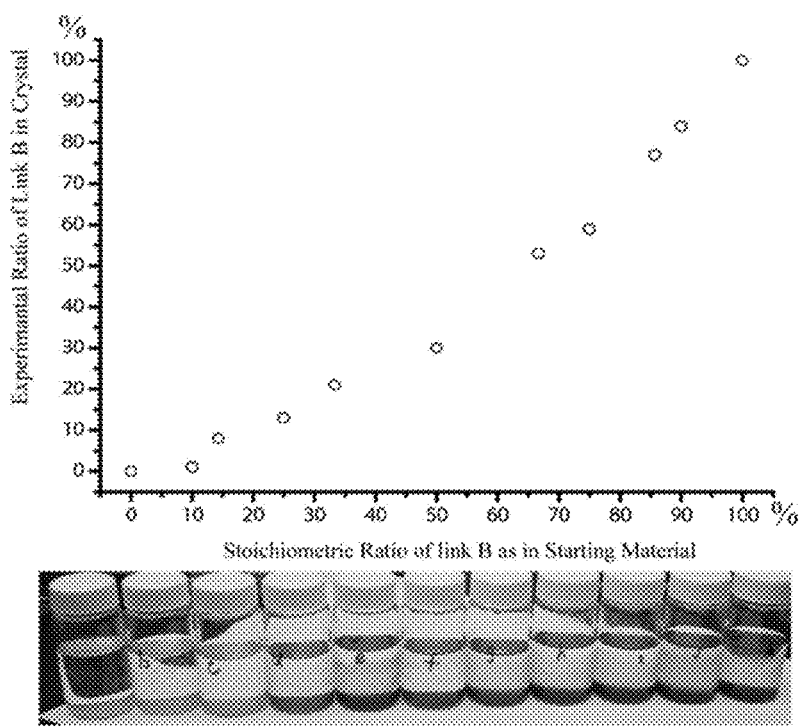
FIG. 40 is a plot of the percent ratio of B in mvMOF-5-AB series determined by solution $^1$H NMR versus the stoichiometric ratio used in the synthesis (top) together with optical image of the crystals showing the color change from colorless to red (from left to right, respectively), mvMOF-5-AB-a to mvMOF-5-AB-k (bottom).
Figure 41:
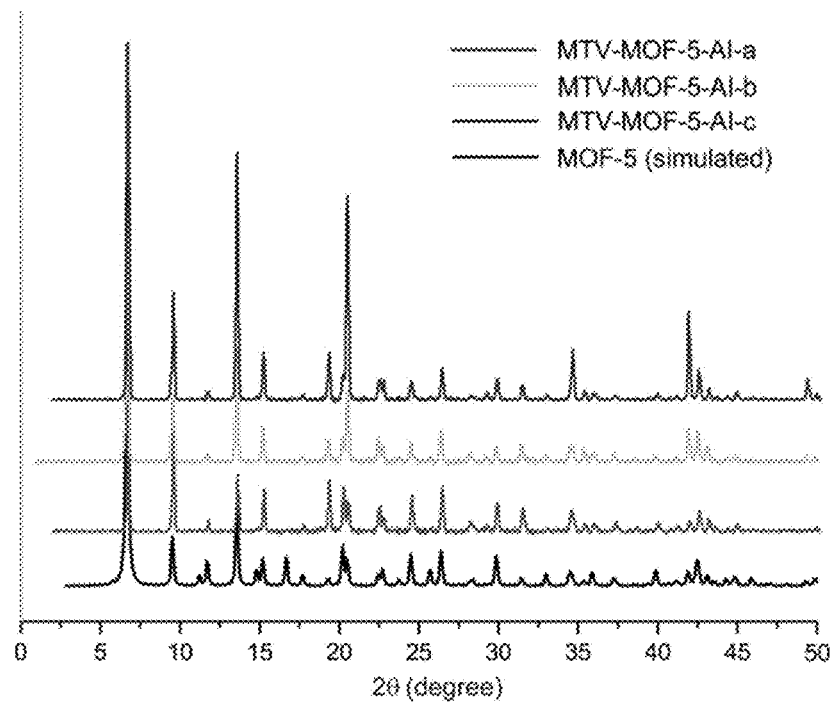
FIG. 41 is a comparison of the experimental PXRD pattern of as-prepared mvMOF-5-AI series (a-c) with the simulated MOF-5 diffraction pattern (black). The very high degree of correspondence between the patterns indicates that the bulk materials all have the same topology as MOF-5.
Figure 42:
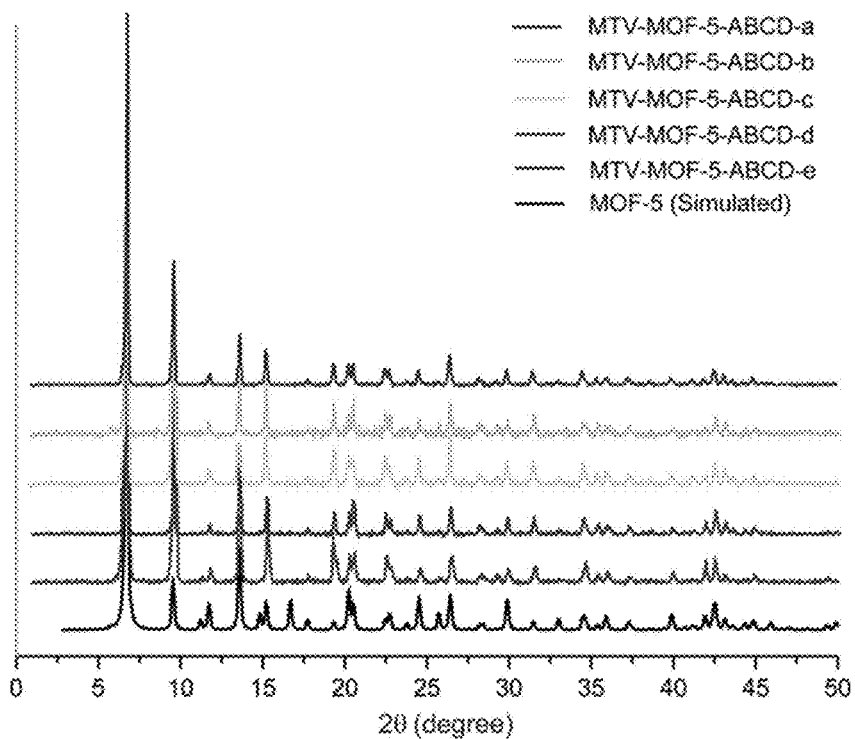
FIG. 42 is a comparison of the experimental PXRD pattern of as-prepared mvMOF-5-ABCD series (a-e) with the simulated MOF-5 diffraction pattern (black). The very high degree of correspondence between the patterns indicates that the bulk materials all have the same topology as MOF-5.

0.30M Zn(NO$_3$)$_2$.4H$_2$O stock solution, 0.10M BDCH$_2$ (link A) and NH$_2$-BDCH$_2$ (link B) stock solutions were prepared in advance. Various volume of link A and link B stock solutions were added in to 2.0 mL of 0.30M Zn(NO$_3$)$_2$.4H$_2$O stock solution followed by DEF to make the total volume to be 10 mL in 20 mL glass vials. The vial was sealed and heated in an isothermal oven at 100° C. and allowed to react solvothermally for 48 h. Eleven mvMOF-5-AB compounds were synthesized, a-k respectively, where mvMOF-5-AB-a only has link A and mvMOF-5-AB-k only has link B, thus they are actually MOF-5 and IRMOF-3 respectively. All products were in the form of cubic shaped single crystals. The crystallinity of each compound was confirmed by PXRD, the very high degree of correspondence with the simulated MOF-5 pattern indicates that these compounds inherent the unaltered MOF-5 topology (FIG. 40). Ratio of the links within mvMOFs are determined by $^1$H NMR in the same way described previously. Table 3 summarized the amount of stock solutions were used in each compound and their initial link ratios and those of their products. The percent ratio of B in crystal product of mvMOF-5-AB series was plotted against their initial stoichiometric ratio (FIG. 40). More link B was found in the crystal product as more link B was added as starting materials. This clearly demonstrates that the link ratio in mvMOFs can be fine-tuned in whole range simply by controlling the initial amount of links used during synthesis. Since NH$_2$-BDC (link B) has its characteristic red color in the MOF structure, here a gradual change in the color of as-synthesized mvMOF-5-AB crystals was observed, which further indicates the capability of precise control of link ratio in mvMOFs. As the percentage of link B increases from compound -a to -k, the color of the crystal change form colorless to red and then dark red (FIG. 40).

that these compounds inherent the unaltered MOF-5 topology (FIG. 42). Ratio of the links within mvMOFs are determined by $^1$H NMR in the same way described previously. Table 4 summarized the amount of stock solutions were used in each compound and their initial link ratios and those of their products. Similar to mvMOF-5-AB series, percent ratio of I in crystal product of mvMOF-5-AI series increases as more link I was used in starting material.

TABLE 4

Summary of synthesis of mvMOF-5-AI series, their added stoichiometric link ratio and the ratio found in their crystals.

| Compound | Link A Solution/ mL | Link B Solution/ mL | Zn(NO$_3$)$_2$•4H$_2$O/ mL | I:A stoichiometric Ratio | I:A Ratio in crystal product |
|---|---|---|---|---|---|
| mvMOF-5-AI-a | 1.0 | 1.0 | 2.0 | 1:1 | 0.43:1 |
| mvMOF-5-AI-b | 1.3 | 0.7 | 2.0 | 2:1 | 0.98:1 |
| mvMOF-5-AI-c | 1.5 | 0.5 | 2.0 | 3:1 | 1.9:1 |

Synthesis of mvMOF-5-ABCD Series.

0.30M Zn(NO$_3$)$_2$.4H$_2$O stock solution, 0.10M BDCH$_2$ (link A) and NH$_2$-BDCH$_2$ (link B), Br-BDCH$_2$ (link C), (Cl)$_2$-BDCH$_2$ (link D) stock solutions were prepared in advance. Various volume of link A and link I stock solutions were added in to 2.0 mL of 0.30M Zn(NO$_3$)$_2$.4H$_2$O stock solution followed by adding DEF to make the total volume to be 10 mL in 20 mL glass vials. The vial was sealed and heated in an isothermal oven at 100° C. and allowed to react solvothermally for 48 h. Five mvMOF-5-ABCD compounds were synthesized, a-e respectively. All products were in the form of cubic shaped single crystals. The crystallinity of each compound was confirmed by PXRD, the very high degree of

TABLE 3

Summary of synthesis of mvMOF-5-AB series, their added stoichiometric link ratio and the ratio found in their crystals.

| Compound | Link A Solution/ mL | Link B Solution/ mL | Zn(NO$_3$)$_2$•4H$_2$O/ mL | B:A stoichiometric Ratio | B:A Ratio in crystal product |
|---|---|---|---|---|---|
| mvMOF-5-AB-a | 2.0 | 0 | 2.0 | 0:10 | 0:10 |
| mvMOF-5-AB-b | 1.8 | 0.2 | 2.0 | 1:9 | 0.01:1 |
| mvMOF-5-AB-c | 1.7 | 0.3 | 2.0 | 1:6 | 0.9:1 |
| mvMOF-5-AB-d | 1.5 | 0.5 | 2.0 | 1:3 | 0.15:1 |
| mvMOF-5-AB-e | 1.3 | 0.7 | 2.0 | 1:2 | 0.26:1 |
| mvMOF-5-AB-f | 1.0 | 1.0 | 2.0 | 1:1 | 0.43:1 |
| mvMOF-5-AB-g | 0.7 | 1.3 | 2.0 | 2:1 | 1.2:1 |
| mvMOF-5-AB-h | 0.5 | 1.5 | 2.0 | 3:1 | 1.5:1 |
| mvMOF-5-AB-i | 0.3 | 1.7 | 2.0 | 6:1 | 3.4:1 |
| mvMOF-5-AB-j | 0.2 | 1.8 | 2.0 | 9:1 | 5.1:1 |
| mvMOF-5-AB-k | 0 | 2.0 | 2.0 | 10:0 | 10:0 | mvMOF-5-AB-a and mvMOF-5-AB-k are actually MOF-5 and IRMOF-3 respectively.

Synthesis of mvMOF-5-AI Series.

Figure 43:
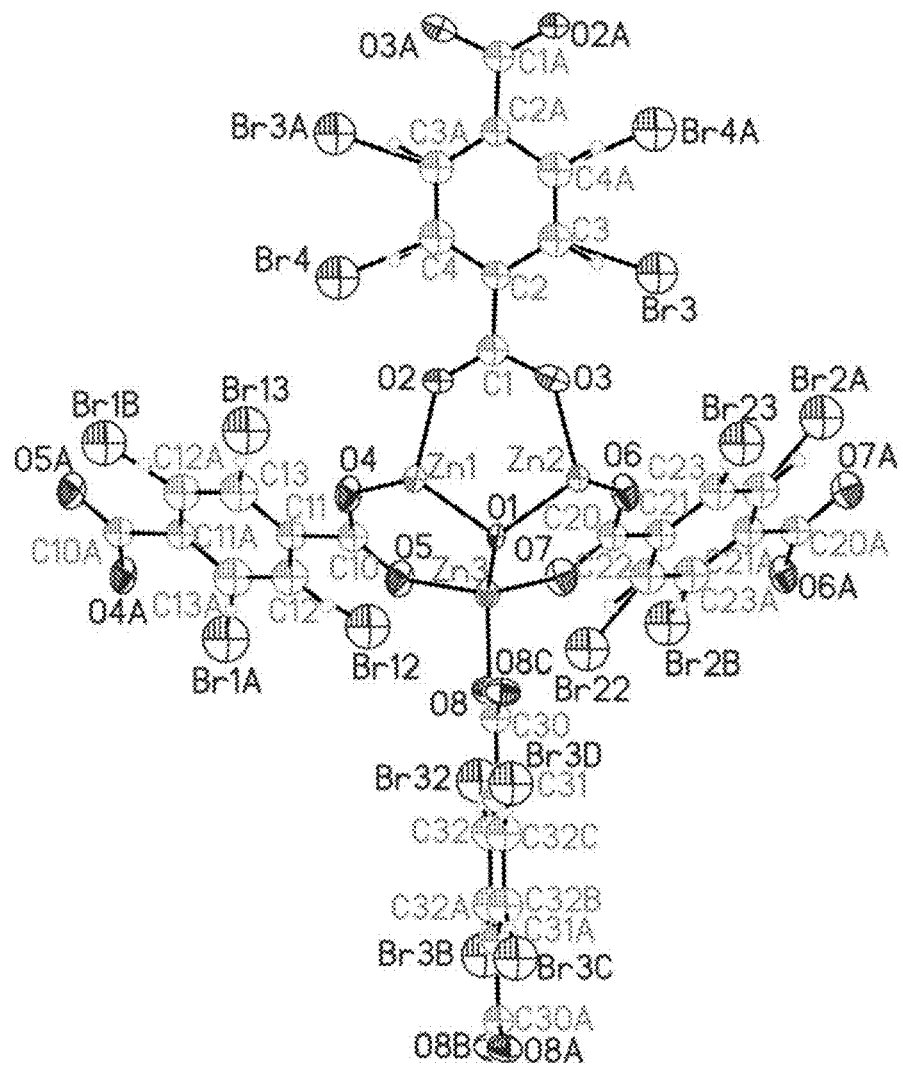
FIG. 43 shows an ORTEP drawing of a mvMOF-5-AC unit with both components of disordered groups shown, including hydrogen atoms and Br atoms. Zn and O atoms were refined anisotropicly, while C and Br atoms were refined isotropicly, and H atoms were put into the calculated position. All ellipsoids are displayed at the 15% probability level. Note that on each phenyl ring, only one position is occupied by Br, out of all four positions as occupied by Br with equal possibility.
Figure 44:
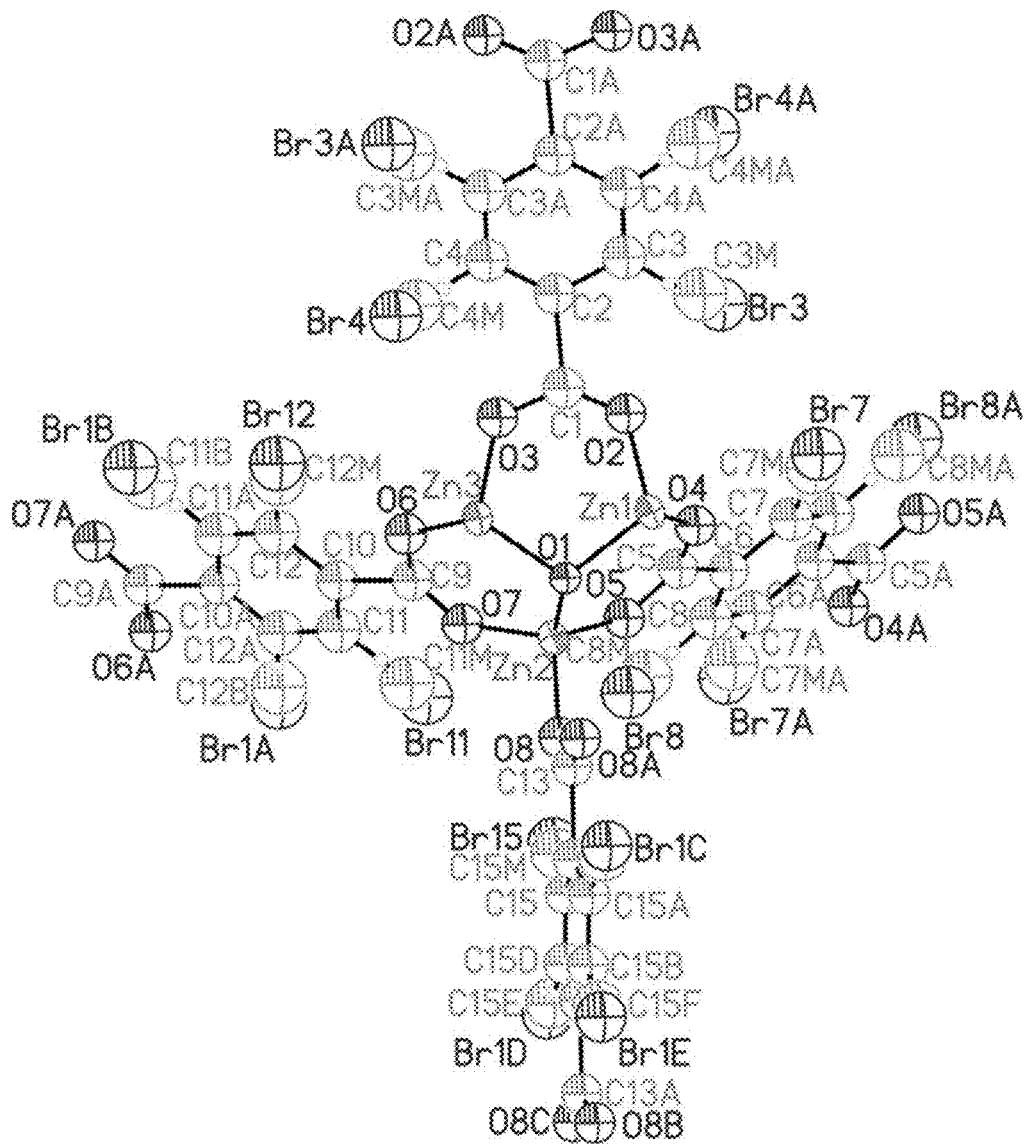
FIG. 44 shows an ORTEP drawing of a mvMOF-5-ACEF unit with all components of the disordered groups shown (Br, $CH_3$, H). Only Zn were refined anisotropicly, while O, C and Br atoms were refined isotropicly, and H atoms were put into the calculated position. All ellipsoids are displayed at the 15% probability level. Note that each phenyl ring can have Br in one of four positions and a methyl group in two of four positions and that these can't co-exist. On this drawing, and in the structure refinement, the constitution of $NO_2$, present in a very minor amount, has been neglected.

0.30M Zn(NO$_3$)$_2$.4H$_2$O stock solution, 0.10M BDCH$_2$ (link A) and (C$_7$H$_7$O)$_2$-BDCH$_2$ (link I) stock solutions were prepared in advance. Various volume of link A and link I stock solutions were added in to 2.0 mL of 0.30M Zn(NO$_3$)$_2$.4H$_2$O stock solution followed by DEF to make the total volume to be 10 mL in 20 mL glass vials. The vial was sealed and heated in an isothermal oven at 100° C. and allowed to react solvothermally for 24 h. Three mvMOF-5-AI compounds were synthesized, a-c respectively. All products were in the form of cubic shaped single crystals. The crystallinity of each compound was confirmed by PXRD, the very high degree of correspondence with the simulated MOF-5 pattern indicates correspondence with the simulated MOF-5 pattern indicates that these compounds inherent the unaltered MOF-5 topology (FIG. 43). Ratio of the links within mvMOFs are determined by $^1$H NMR in the same way described in section 1. Table 5 summarized the amount of stock solutions were used in each compound and in Table 1 (Control of Link Ratio part) in the text. When comparing the link ratios of mvMOF-5-ABCD crystals to the stoichiometric ratio of links used in the synthesis of each compound, as increase (or decrease) in the amount of certain links used as in starting materials, the ratio in the resulting mvMOF increases (or decreases) correspondently. These again demonstrate that the ratio of link within mvMOFs is controllable.

TABLE 5

Summary of synthesis of mvMOF-5-ABCD series.

| Compound | Link A Solution/ mL | Link B Solution/ mL | Link C Solution/ mL | Link D Solution/ mL | $Zn(NO_3)_2 \cdot 4H_2O$/ mL |
|---|---|---|---|---|---|
| mvMOF-5-ABCD-a | 0.50 | 0.50 | 0.50 | 0.50 | 2.0 |
| mvMOF-5-ABCD-b | 0.25 | 0.50 | 0.50 | 0.75 | 2.0 |
| mvMOF-5-ABCD-c | 0.75 | 0.50 | 0.50 | 0.25 | 2.0 |
| mvMOF-5-ABCD-d | 0.50 | 0.75 | 0.25 | 0.50 | 2.0 |
| mvMOF-5-ABCD-e | 0.50 | 0.25 | 0.75 | 0.50 | 2.0 |

Single X-Ray Diffraction Data Collection, Structure Solution, and Refinement Procedures for mvMOF-5-AC and -ACEF.

General procedures for single crystal data collection, structure solution, and refinement are presented here. Unique details for each structure including structural disorders are described prior to the experimental and metrical listings for each structure.

General Data Collection and Refinement Procedures:

Data were collected on a Bruker SMART APEXII three circle diffractometer equipped with a CCD area detector and operated at 1200 W power (40 kV, 30 mA) to generate Cu Kα radiation ($\lambda$=1.5418 Å). The incident X-ray beam was focused and monochromated using Bruker Excalibur Gobel mirror optics. Crystals were all mounted in flame sealed borosilicate capillaries containing a small amount of mother liquor to prevent desolvation during data collection.

Initial ω-φ scans of each specimen were taken to obtain preliminary unit cell parameters and to assess the mosaicity (i.e. breadth of spots between frames) of the crystal to select the required frame width for data collection. For all cases frame widths of 0.5° were judged to be appropriate and full hemispheres of data were collected using the Bruker APEX2 software suite to carry out overlapping φ and ω scans at different detector (2θ) settings. Following data collection, reflections were sampled from all regions of the Ewald sphere to redetermine unit cell parameters for data integration and to check for rotational twinning using CELL_NOW.

Following exhaustive review of collected frames the resolution of the dataset was judged, and, if necessary, regions of the frames where no coherent scattering was observed were removed from consideration for data integration. Data were integrated using Bruker APEX2 V 2.1 software with a narrow frame algorithm and a 0.400 fractional lower limit of average intensity. Absorption corrections were ineffectual for improving the quality of the data, which is not unexpected for small crystals of low density materials containing primarily light atoms.

The space group determination and tests for merohedral twinning were carried out using XPREP. In all cases the highest possible space group was chosen and no indications of merohedral twinning were observed. All structures were solved by direct methods and refined using the SHELXTL'97 software suite. Atoms were located from iterative examination of difference F-maps following least-squares refinements of the earlier models. Final models were refined anisotropically (if the number of data permitted and stable refinement could be reached) until full convergence was achieved. Partial occupancies were assigned to each pair of atoms in the disordered groups. Some atoms could not be located precisely due to high disorder and low occupancy (Nitro group on link E in mvMOF-ACEF). Hydrogen atoms were placed in calculated positions and included as riding atoms. Modeling of electron density within the voids of the frameworks did not lead to identification of all guest entities in structures due to the lowered resolution of the data. This difficulty, which is typical of porous crystals that contain solvent filled pores, lies in the raw data where observed strong (high intensity) scattering becomes limited to ~1.0 Å at best, with higher resolution data present but weak (low intensity). As is a common strategy for improving X-ray data, increasing the exposure time of the crystal to X-rays did not ameliorate the quality of the high angle data in these cases, as the intensity from low angle data saturated the detector and minimal improvement in the high angle data was achieved. Additionally, diffuse scattering from the disordered functional groups on the phenyl unit of the MOF backbone and solvents in the void spaces within the crystal and solvents from the capillary used to mount the crystal contributed to the background noise and sometimes to the 'washing out' of high angle data. For these extended framework structures it was also more reasonable to model against data collected at a higher range of temperatures (−50 to −15° C., rather than −120 to −100° C.) when guest entities in the structures were allowed to move freely and therefore did not contribute coherent scattering terms to the observed structure factors.

To prove the correctness of the atomic positions in the framework, the application of the SQUEEZE routine of A. Spek has been performed when applicable. However, atomic co-ordinates for the "non-SQUEEZE" structures have also been presented and the CIFs were also submitted for the cases where the program SQUEEZE has been employed. All structures were examined using the Adsym subroutine of PLATON to assure that no additional symmetry could be applied to the models. All ellipsoids in ORTEP diagrams are displayed at the 15% probability level unless noted otherwise. For all structures the elevated R-values are commonly encountered in MOF crystallography, for the reasons expressed above.

Experimental and Refinement Details for mvMOF-5-AC.

A colorless parallelepiped crystal (0.41×0.41×0.28 $mm^3$) of mvMOF-5-AC was placed in a 0.5 mm diameter borosilicate capillary along with a small amount of mother liquor. The capillary was flame sealed and mounted on a SMART APEXII three circle diffractometer equipped with a CCD area detector and operated at 1200 W power (40 kV, 30 mA) to generate Cu Kα radiation ($\lambda$=1.5418 Å) while being cooled to 258(2) K in a liquid $N_2$ cooled stream of nitrogen. Full hemispheres of data were collected, using the Bruker APEX2 software suite to carry out overlapping φ and ω scans at three different detector (2θ) settings (2θ=28, 60, 1000). A total of 14178 reflections were collected of which 2951 were unique and 1994 of these were greater than 2σ(I). The range of θ was from 2.97 to 41.28°. Analysis of the data showed negligible decay during collection. The program Scale was performed to minimize differences between symmetry related or repeatedly measured reflections.

The structure was solved in the monoclinic C2/m space group with Z=8 using direct methods. Zn and O atoms in the backbone of the framework were refined anisotropically and all other nonhydrogen atoms were refined isotropicly, with hydrogen atoms generated as spheres riding the coordinates of their parent atoms. The attempts made to model solvent molecules did not lead to identification of guest entities. Since the solvent is not bonded to the framework, imprecise locations for solvent molecules were expected for the MOF structure. In addition, very high displacement parameters, high esd's and partial occupancy due to the disorder made it impossible to determine accurate positions for the solvent molecules. Nonetheless, assignment and refinement of the backbone framework and —Br group of mvMOF-5-AC was unambiguous, as judged by the resulting bond and angle metrics.

To improve the atomic positions in the framework the application of the SQUEEZE routine of A. Spek has been performed. However, atomic co-ordinates for the "non-SQUEEZE" structure are also presented. Final full matrix least-squares refinement on $F^2$ converged to R1=0.1257 (F>2σ(F)) and wR2=0.3084 (all data) with GOF=0.998. For the structure where the SQUEEZE program has not been employed, final full matrix least-squares refinement on $F^2$ converged to R1=0.1892 (F>2σ(F)) and wR2=0.4184 (all data) with GOF=1.426. When only framework atoms were included in the latter structure factor calculation, the residual electron density in the F-map was located within the pores of mvMOF-5-AC. The empirical formula for crystal structure refinement is C12 H5.43 Br0.57 O7.25 Zn2, with a density of 0.683 g cm$^{-3}$, based on the measured ratio of the two types of links in the crystal by $^1$H NMR.

TABLE 6

Crystal data and structure refinement for mvMOF-5-AC.

| | |
|---|---|
| Empirical formula | C12 H5.43 Br0.57 O7.25 Zn2 |
| Formula weight | 441.88 |
| Temperature | 258(2) K. |
| Wavelength | 1.54178 Å |
| Crystal system | Monoclinic |
| Space group | C2/m |
| Unit cell dimensions | a = 31.6131(7) Å    α = 90°. |
| | b = 18.252 Å    β = 125.26°. |
| | c = 18.252 Å    γ = 90°. |
| Volume | 8598.74(19) Å$^3$ |
| Z | 8 |
| Density (calculated) | 0.683 g/cm$^3$ |
| Absorption coefficient | 2.102 mm$^{-1}$ |
| F(000) | 1723 |
| Crystal size | 0.28 × 0.41 × 0.41 mm$^3$ |
| Theta range for data collection | 2.97 to 41.28°. |
| Index ranges | −27 <= h <= 26, −15 <= k <= 15, |
| | −15 <= l <= 15 |
| Reflections collected | 14178 |
| Independent reflections | 2951 [R(int) = 0.3363] |
| Completeness to theta = 41.28° | 99.5% |
| Refinement method | Full-matrix least-squares on $F^2$ |
| Data/restraints/parameters | 2951/0/154 |
| Goodness-of-fit on $F^2$ | 1.426 |
| Final R indices [I > 2sigma(I)] | $R_I$ = 0.1711, w$R_2$ = 0.4040 |
| R indices (all data) | $R_I$ = 0.1892, w$R_2$ = 0.4184 |
| Largest diff. peak and hole | 1.266 and −0.739 e.Å$^{-3}$ |

TABLE 7

Crystal data and structure refinement for mvMOF-5-AC (SQUEEZE).

| | |
|---|---|
| Empirical formula | C12 H5.43 Br0.57 O7.25 Zn2 |
| Formula weight | 441.88 |
| Temperature | 258(2) K. |
| Wavelength | 1.54178 Å |
| Crystal system | Monoclinic |
| Space group | C2/m |
| Unit cell dimensions | a = 31.6131(7) Å    α = 90°. |
| | b = 18.252 Å    β = 125.26°. |
| | c = 18.252 Å    γ = 90°. |
| Volume | 8598.74(19) Å$^3$ |
| Z | 8 |
| Density (calculated) | 0.683 g/cm$^3$ |
| Absorption coefficient | 2.102 mm$^{-1}$ |
| F(000) | 1723 |
| Crystal size | 0.41 × 0.41 × 0.28 mm$^3$ |
| Theta range for data collection | 2.97 to 41.28°. |
| Index ranges | −27 <= h <= 26, −15 <= k <= 15, |
| | −15 <= l <= 15 |

TABLE 7-continued

Crystal data and structure refinement for mvMOF-5-AC (SQUEEZE).

| | |
|---|---|
| Reflections collected | 14178 |
| Independent reflections | 2951 [R(int) = 0.3267] |
| Completeness to theta = 41.28° | 99.5% |
| Refinement method | Full-matrix least-squares on $F^2$ |
| Data/restraints/parameters | 2951/0/144 |
| Goodness-of-fit on $F^2$ | 0.998 |
| Final R indices [I > 2sigma(I)] | $R_I$ = 0.1102, w$R_2$ = 0.2855 |
| R indices (all data) | $R_I$ = 0.1257, w$R_2$ = 0.3084 |
| Largest diff. peak and hole | 0.983 and −0.426 e.Å$^{-3}$ |

TABLE 8

Atomic coordinates (×10$^4$) and equivalent isotropic displacement parameters (Å$^2$ × 10$^3$) for mvMOF-5-AC. U(eq) is defined as one third of the trace of the orthogonalized U$^{ij}$ tensor.

| | x | y | z | U (eq) |
|---|---|---|---|---|
| Zn (1) | 2937 (1) | 0 | 3808 (2) | 74 (2) |
| Zn (2) | 2936 (1) | 0 | 2061 (2) | 73 (2) |
| Zn (3) | 2063 (1) | 872 (1) | 2063 (2) | 73 (1) |
| O (1) | 2501 (6) | 0 | 2502 (9) | 57 (4) |
| O (2) | 3667 (7) | 0 | 4289 (13) | 107 (6) |
| O (3) | 3683 (17) | 0 | 3084 (17) | 119 (7) |
| C (1) | 3899 (15) | 0 | 3930 (30) | 108 (11) |
| C (2) | 4460 (12) | 0 | 4460 (20) | 95 (9) |
| C (3) | 4726 (14) | 0 | 4090 (30) | 129 (12) |
| Br (3) | 4470 (20) | 0 | 2760 (40) | 193 |
| C (4) | 4750 (15) | 0 | 5380 (30) | 141 (13) |
| Br (4) | 4450 (30) | 0 | 6130 (50) | 211 |
| O (4) | 2816 (6) | 865 (8) | 4299 (10) | 116 (5) |
| O (5) | 2173 (6) | 1484 (8) | 3037 (11) | 116 (5) |
| C (10) | 2488 (10) | 1394 (14) | 3864 (19) | 101 (7) |
| C (11) | 2497 (8) | 1973 (12) | 4468 (15) | 99 (6) |
| C (12) | 2179 (11) | 2552 (17) | 4100 (20) | 149 (10) |
| Br (12) | 1804 | 2722 | 2874 | 224 |
| C (13) | 2825 (12) | 1924 (18) | 5360 (20) | 166 (11) |
| Br (13) | 3293 | 1135 | 5838 | 249 |
| O (6) | 2823 (7) | 861 (8) | 1351 (10) | 115 (5) |
| O (7) | 2183 (6) | 1479 (8) | 1323 (10) | 118 (5) |
| C (20) | 2492 (10) | 1386 (15) | 1098 (16) | 103 (7) |
| C (21) | 2493 (9) | 1944 (13) | 529 (15) | 109 (7) |
| C (22) | 2177 (10) | 2538 (15) | 277 (17) | 141 (9) |
| Br (22) | 1631 | 2486 | 385 | 212 |
| C (23) | 2817 (10) | 1902 (16) | 243 (18) | 147 (10) |
| Br (23) | 3186 | 1057 | 450 | 221 |
| O (8) | 1338 (5) | 627 (8) | 1346 (10) | 114 (5) |
| C (30) | 1135 (13) | 0 | 1150 (20) | 101 (10) |
| C (31) | 533 (12) | 0 | 530 (20) | 104 (9) |
| C (32) | 271 (9) | 637 (16) | 275 (17) | 146 (10) |
| Br (32) | 655 | 1523 | 680 | 220 |

TABLE 9

Bond lengths [Å] and angles [°] for mvMOF-5-AC.

| | | | |
|---|---|---|---|
| Zn(1)-O(2) | 1.938 (19) | C(10)-C(11) | 1.52 (3) |
| Zn(1)-O(1) | 1.946 (14) | C(11)-C(13) | 1.34 (3) |
| Zn(1)-O(4) | 1.958 (13) | C(11)-C(12) | 1.34 (3) |
| Zn(1)-O(4)#1 | 1.958 (13) | C(12)-C(13)#3 | 1.38 (3) |
| Zn(2)-O(6)#1 | 1.934 (14) | C(12)-H(12) | 0.9300 |
| Zn(2)-O(6) | 1.934 (14) | C(13)-C(12)#3 | 1.38 (3) |
| Zn(2)-O(1) | 1.952 (14) | C(13)-H(13) | 0.9300 |
| Zn(2)-O(3) | 1.99 (2) | O(6)-C(20) | 1.29 (3) |
| Zn(3)-O(8) | 1.923 (14) | O(7)-C(20) | 1.27 (3) |
| Zn(3)-O(7) | 1.946 (14) | C(20)-C(21) | 1.45 (3) |
| Zn(3)-O(1) | 1.952 (9) | C(21)-C(22) | 1.36 (3) |
| Zn(3)-O(5) | 1.954 (13) | C(21)-C(23) | 1.40 (3) |
| O(1)-Zn(3)#1 | 1.952 (9) | C(22)-C(23)#4 | 1.40 (3) |
| O(2)-C(1) | 1.23 (4) | C(22)-H(22) | 0.9300 |
| O(3)-C(1) | 1.28 (4) | C(23)-C(22)#4 | 1.40 (3) |
| C(1)-C(2) | 1.45 (4) | C(23)-H(23) | 0.9300 |
| C(2)-C(3) | 1.35 (4) | O(8)-C(30) | 1.258 (18) |

TABLE 9-continued

Bond lengths [Å] and angles [°] for mvMOF-5-AC.

| | | | |
|---|---|---|---|
| C(2)-C(4) | 1.38 (4) | C(30)-O(8)#1 | 1.258 (18) |
| C(3)-C(4)#2 | 1.35 (4) | C(30)-C(31) | 1.55 (4) |
| C(3)-H(3) | 0.9300 | C(31)-C(32)#1 | 1.35 (3) |
| C(4)-C(3)#2 | 1.35 (4) | C(31)-C(32) | 1.35 (3) |
| C(4)-H(4) | 0.9300 | C(32)-C(32)#5 | 1.40 (5) |
| O(4)-C(10) | 1.30 (3) | C(32)-H(32) | 0.9300 |
| O(5)-C(10) | 1.25 (3) | | |
| O(2)-Zn(1)-O(1) | 111.8 (8) | C(2)-C(3)-C(4)#2 | 120 (4) |
| O(2)-Zn(1)-O(4) | 106.7 (6) | C(2)-C(3)-H(3) | 119.8 |
| O(1)-Zn(1)-O(4) | 111.9 (5) | C(4)#2-C(3)-H(3) | 119.8 |
| O(2)-Zn(1)-O(4)#1 | 106.7 (6) | C(3)#2-C(4)-C(2) | 123 (4) |
| O(1)-Zn(1)-O(4)#1 | 111.9 (5) | C(3)#2-C(4)-H(4) | 118.4 |
| O(4)-Zn(1)-O(4)#1 | 107.5 (9) | C(2)-C(4)-H(4) | 118.4 |
| O(6)#1-Zn(2)-O(6) | 108.6 (9) | C(10)-O(4)-Zn(1) | 128.1 (16) |
| O(6)#1-Zn(2)-O(1) | 112.0 (5) | C(10)-O(5)-Zn(3) | 128.5 (16) |
| O(6)-Zn(2)-O(1) | 112.0 (5) | O(5)-C(10)-O(4) | 129 (2) |
| O(6)#1-Zn(2)-O(3) | 106.7 (6) | O(5)-C(10)-C(11) | 117 (2) |
| O(6)-Zn(2)-O(3) | 106.7 (6) | O(4)-C(10)-C(11) | 114 (2) |
| O(1)-Zn(2)-O(3) | 110.5 (8) | C(13)-C(11)-C(12) | 120 (2) |
| O(8)-Zn(3)-O(7) | 107.0 (7) | C(13)-C(11)-C(10) | 121 (3) |
| O(8)-Zn(3)-O(1) | 111.9 (5) | C(12)-C(11)-C(10) | 119 (2) |
| O(7)-Zn(3)-O(1) | 111.9 (6) | C(11)-C(12)- | 120 (3) |
| O(8)-Zn(3)-O(5) | 105.6 (7) | C(11)-C(12)-H(12) | 120.0 |
| O(7)-Zn(3)-O(5) | 107.6 (7) | C(13)#3-C(12)- | 120.0 |
| O(1)-Zn(3)-O(5) | 112.4 (6) | C(11)-C(13)- | 120 (3) |
| Zn(1)-O(1)-Zn(3)#1 | 109.6 (5) | C(11)-C(13)-H(13) | 119.9 |
| Zn(1)-O(1)-Zn(3) | 109.6 (5) | C(12)#3-C(13)- | 119.9 |
| Zn(3)#1-O(1)-Zn(3) | 109.2 (7) | C(20)-O(6)-Zn(2) | 129.9 (16) |
| Zn(1)-O(1)-Zn(2) | 109.6 (5) | C(20)-O(7)-Zn(3) | 130.0 (17) |
| Zn(3)#1-O(1)-Zn(2) | 109.4 (5) | O(7)-C(20)-O(6) | 127 (2) |
| Zn(3)-O(1)-Zn(2) | 109.4 (5) | O(7)-C(20)-C(21) | 117 (2) |
| C(1)-O(2)-Zn(1) | 133 (2) | O(6)-C(20)-C(21) | 116 (2) |
| C(1)-O(3)-Zn(2) | 130 (2) | C(22)-C(21)-C(23) | 118 (2) |
| O(2)-C(1)-O(3) | 125 (4) | C(22)-C(21)-C(20) | 120 (2) |
| O(2)-C(1)-C(2) | 122 (4) | C(23)-C(21)-C(20) | 122 (2) |
| O(3)-C(1)-C(2) | 113 (4) | C(21)-C(22)- | 121 (2) |
| C(3)-C(2)-C(4) | 116 (3) | C(21)-C(22)-H(22) | 119.5 |
| C(3)-C(2)-C(1) | 123 (3) | C(23)#4-C(22)- | 119.5 |
| C(4)-C(2)-C(1) | 120 (3) | C(21)-C(23)- | 121 (3) |
| C(21)-C(23)-H(23) | 119.6 | C(32)#1-C(31)- | 120 (3) |
| C(22)#4-C(23)-H(23) | 119.6 | C(32)#1-C(31)- | 120.2 (16) |
| C(30)-O(8)-Zn(3) | 128.1 (19) | C(32)-C(31)-C(30) | 120.2 (16) |
| O(8)-C(30)-O(8)#1 | 131 (3) | C(31)-C(32)- | 120.2 (16) |
| O(8)-C(30)-C(31) | 114.6 (16) | C(31)-C(32)-H(32) | 119.9 |
| O(8)#1-C(30)-C(31) | 114.6 (16) | C(32)#5-C(32)- | 119.9 |

Symmetry Transformations Used to Generate Equivalent Atoms:

1 x, -y, z #2 -x + 1, -y, -z + 1 #3 -x + ½, -y + ½, -z + 1
4 -x + ½, -y + ½, -z #5 -x, y, -z

TABLE 10

Anisotropic displacement parameters (Å$^2$ × 10$^3$) for mvMOF-5-AC.

| | $U^{11}$ | $U^{22}$ | $U^{33}$ | $U^{23}$ | $U^{13}$ | $U^{12}$ |
|---|---|---|---|---|---|---|
| Zn(1) | 86 (3) | 75 (2) | 64 (3) | 0 | 46 (2) | 0 |
| Zn(2) | 85 (3) | 76 (2) | 67 (2) | 0 | 50 (2) | 0 |
| Zn(3) | 84 (2) | 69 (2) | 71 (2) | 3 (1) | 47 (2) | 4 (1) |
| O(1) | 70 (10) | 66 (10) | 40 (9) | 0 | 35 (8) | 0 |
| O(2) | 67 (12) | 148 (18) | 93 (14) | 0 | 38 (11) | 0 |
| O(3) | 81 (14) | 141 (18) | 140 (20) | 0 | 69 (14) | 0 |
| O(4) | 153 (13) | 107 (12) | 97 (11) | -36 (9) | 78 (10) | 3 (11) |
| O(5) | 153 (13) | 95 (10) | 106 (12) | -29 (8) | 78 (11) | 18 (9) |
| O(6) | 156 (14) | 111 (12) | 122 (12) | 33 (9) | 106 (11) | 3 (11) |
| O(7) | 158 (14) | 92 (10) | 127 (12) | 39 (9) | 96 (11) | 5 (9) |
| O(8) | 86 (10) | 117 (12) | 130 (12) | 7 (10) | 57 (9) | 23 (9) |

The anisotropic displacement factor exponent takes the form: $-2\pi^2[h^2 a^{*2} U^{11} + \ldots + 2 h k a^* b^* U^{12}]$

TABLE 11

Hydrogen coordinates (×10$^4$) and isotropic displacement parameters (Å$^2$ × 10$^3$) for mvMOF-5-AC.

| | x | y | z | U(eq) |
|---|---|---|---|---|
| H(3) | 4549 | 0 | 3470 | 155 |
| H(4) | 4576 | 0 | 5655 | 169 |
| H(12) | 1962 | 2600 | 3477 | 179 |
| H(13) | 3058 | 1535 | 5616 | 199 |
| H(22) | 1954 | 2572 | 452 | 170 |
| H(23) | 3033 | 1498 | 399 | 176 |
| H(32) | 450 | 1079 | 470 | 176 |

Experimental and Refinement Details for mvMOF-5-ACEF.

A red parallelepiped crystal (0.30×0.30×0.21 mm$^3$) of mvMOF-5-ACEF was placed in a 0.4 mm diameter borosilicate capillary along with a small amount of mother liquor. The capillary was flame sealed and mounted on a SMART APEXII three circle diffractometer equipped with a CCD area detector and operated at 1200 W power (40 kV, 30 mA) to generate Cu Kα radiation (λ=1.5418 Å) while being cooled to 233(2) K in a liquid N2 cooled stream of nitrogen. Full hemispheres of data were collected using the Bruker APEX2 software suite to carry out overlapping φ and ω scans at three different detector (2θ) settings (2θ=28, 60, 1000). A total of 13758 reflections were collected of which 2855 were unique and 1918 of these were greater than 2σ(I). The range of θ was from 2.99 to 41.02°. Analysis of the data showed negligible decay during collection. The program Scale was performed to minimize differences between symmetry related or repeatedly measured reflections.

The structure was solved in the monoclinic C2/m space group with Z=8 using direct methods. Zn atoms in the backbone of the framework were refined anisotropically and all other nonhydrogen atoms were refined isotropicly, with hydrogen atoms generated as spheres riding the coordinates of their parent atoms. The attempts made to model solvent molecules did not lead to identification of guest entities. Since the solvent is not bonded to the framework, imprecise locations of solvent molecules were expected for the MOF structure. In addition, very high displacement parameters, high esd's and partial occupancy due to the disorder made it impossible to determine accurate positions for the solvent molecules. Nonetheless, assignment and refinement of the backbone framework and the general location of the functional group (—Br and —CH$_3$) of mvMOF-5-ACEF was unambiguous, as judged by the resulting bond and angle metrics. Given the low occupancy (only 9.4% in molar percent) and its disorder over four positions, the constitution of $NO_2$, present in a very minor amount, thus has been neglected in this refinement.

To improve the correctness of the atomic positions in the framework the application of the SQUEEZE routine of A. Spek has been performed. However atomic co-ordinates for the "non-SQUEEZE" structure are also presented. Final full matrix least-squares refinement on $F^2$ converged to R1=0.1219 (F>2σ(F)) and wR2=0.3041 (all data) with GOF=1.003. For the structure where the SQUEEZE program has not been employed, final full matrix least-squares refinement on $F^2$ converged to R1=0.1737 (F>2σ(F)) and wR2=0.3972 (all data) with GOF=1.378. When only framework atoms were included in the latter structure factor calculation, the residual electron density in the F-map was located within the pores of mvMOF-5-ACEF. The empirical formula for crystal structure refinement is C12.81 H6.65 Br0.31 N0.14 O7.78 Zn2, based on the measured ratio of the four types of links in the crystal by $^1$H NMR.

TABLE 12

Crystal data and structure refinement for mvMOF-5-ACEF.

| | |
|---|---|
| Empirical formula | C12.81 H6.65 Br0.31 N0.14 O7.78 Zn2 |
| Formula weight | 443.02 |
| Temperature | 233(2) K. |
| Wavelength | 1.54178 Å |
| Crystal system | Monoclinic |
| Space group | C2/m |
| Unit cell dimensions | a = 31.3518(7) Å     α = 90°. |
| | b = 18.101 Å     β = 125.26°. |
| | c = 18.101 Å     γ = 90°. |
| Volume | 8387.24(19) Å$^3$ |
| Z | 8 |
| Density (calculated) | 0.702 g/cm$^3$ |
| Absorption coefficient | 1.893 mm$^{-1}$ |
| F(000) | 1743 |
| Crystal size | 0.30 × 0.30 × 0.21 mm$^3$ |
| Theta range for data collection | 2.99 to 41.02°. |
| Index ranges | −26 <= h <= 25, −15 <= k <= 15, |
| | −15 <= l <= 15 |
| Reflections collected | 13758 |
| Independent reflections | 2855 [R(int) = 0.2887] |
| Completeness to theta = 41.02° | 99.2% |
| Refinement method | Full-matrix least-squares on $F^2$ |
| Data/restraints/parameters | 2855/0/116 |
| Goodness-of-fit on $F^2$ | 1.378 |
| Final R indices [I > 2sigma(I)] | $R_I$ = 0.1572, $wR_2$ = 0.3799 |
| R indices (all data) | $R_I$ = 0.1737, $wR_2$ = 0.3972 |
| Largest diff. peak and hole | 1.366 and −0.522 e.Å$^{-3}$ |

TABLE 13

Crystal data and structure refinement for mvMOF-5-ACEF (SQUEEZE).

| | |
|---|---|
| Empirical formula | C12.81 H6.65 Br0.31 N0.14 O7.78 Zn2 |
| Formula weight | 443.02 |
| Temperature | 233(2) K. |
| Wavelength | 1.54178 Å |
| Crystal system | Monoclinic |
| Space group | C2/m |
| Unit cell dimensions | a = 31.3518(7) Å     α = 90°. |
| | b = 18.101 Å     β = 125.26°. |
| | c = 18.101 Å     γ = 90°. |
| Volume | 8387.24(19) Å$^3$ |
| Z | 8 |
| Density (calculated) | 0.702 g/cm$^3$ |
| Absorption coefficient | 1.893 mm$^{-1}$ |
| F(000) | 1743 |
| Crystal size | 0.30 × 0.30 × 0.21 mm$^3$ |
| Theta range for data collection | 2.99 to 41.02°. |
| Index ranges | −26 <= h <= 25, −15 <= k <= 15, |
| | −15 <= l <= 15 |
| Reflections collected | 13758 |
| Independent reflections | 2855 [R(int) = 0.2767] |
| Completeness to theta = 41.02° | 99.2% |
| Refinement method | Full-matrix least-squares on $F^2$ |
| Data/restraints/parameters | 2855/0/116 |
| Goodness-of-fit on $F^2$ | 1.003 |
| Final R indices [I > 2sigma(I)] | $R_I$ = 0.1057, $wR_2$ = 0.2771 |
| R indices (all data) | $R_I$ = 0.1219, $wR_2$ = 0.3041 |
| Largest diff. peak and hole | 0.833 and −0.636 e.Å$^{-3}$ |

TABLE 14

Atomic coordinates (×10$^4$) and equivalent isotropic displacement parameters (Å$^2$ × 10$^3$) for mvMOF-5-ACEF. U(eq) is defined as one third of the trace of the orthogonalized U$^{ij}$ tensor.

| | x | y | z | U (eq) |
|---|---|---|---|---|
| Zn (1) | 2062 (1) | 5000 | 1187 (2) | 107 (2) |
| Zn (2) | 2936 (1) | 4127 (1) | 2937 (1) | 107 (1) |
| Zn (3) | 2065 (1) | 5000 | 2938 (2) | 107 (2) |
| O (1) | 2511 (5) | 5000 | 2514 (9) | 93 (4) |
| O (2) | 1356 (7) | 5000 | 698 (13) | 156 (6) |
| O (3) | 1356 (7) | 5000 | 1997 (13) | 159 (6) |
| O (4) | 2178 (5) | 4187 (7) | 718 (9) | 161 (5) |
| O (5) | 2822 (5) | 3529 (7) | 1999 (9) | 160 (5) |
| O (6) | 2169 (5) | 4181 (8) | 3638 (9) | 170 (5) |
| O (7) | 2825 (5) | 3528 (8) | 3644 (9) | 164 (5) |
| O (8) | 3645 (5) | 4347 (8) | 3658 (9) | 161 (4) |
| C (1) | 1161 (13) | 5000 | 1120 (20) | 171 (11) |
| C (2) | 493 (12) | 5000 | 510 (20) | 162 (10) |
| C (3) | 251 (15) | 5000 | −440 (30) | 189 (13) |
| Br (3) | 609 | 5000 | −1045 | 283 |
| C (3M) | 534 | 5000 | −916 | 283 |
| C (4) | 239 (14) | 5000 | 930 (20) | 180 (12) |
| Br (4) | 614 | 5000 | 2250 | 270 |
| C (4M) | 544 | 5000 | 1973 | 270 |
| C (5) | 2484 (8) | 3673 (12) | 1129 (15) | 157 (7) |
| C (6) | 2518 (8) | 3001 (12) | 539 (15) | 152 (7) |
| C (7) | 2169 (9) | 3099 (15) | −449 (18) | 188 (9) |
| Br (7) | 1703 | 3924 | −1067 | 283 |
| C (7M) | 1801 | 3749 | −935 | 283 |
| C (8) | 2856 (9) | 2411 (14) | 968 (17) | 186 (9) |
| Br (8) | 3364 | 2322 | 2332 | 278 |
| C (8M) | 3258 | 2344 | 2045 | 278 |
| C (9) | 2503 (9) | 3672 (12) | 3838 (14) | 161 (8) |
| C (10) | 2495 (8) | 3012 (12) | 4483 (14) | 158 (7) |
| C (11) | 2852 (10) | 2402 (15) | 4738 (17) | 197 (10) |
| Br (11) | 3352 | 2289 | 4364 | 295 |
| C (11M) | 3247 | 2315 | 4442 | 295 |
| C (12) | 2137 (10) | 3113 (15) | 4739 (17) | 202 (10) |
| Br (12) | 1640 | 3971 | 4352 | 303 |
| C (12M) | 1746 | 3790 | 4432 | 303 |
| C (13) | 3848 (11) | 5000 | 3840 (20) | 157 (10) |
| C (14) | 4505 (13) | 5000 | 4510 (20) | 169 (11) |
| C (15) | 4754 (6) | 4293 (11) | 4737 (14) | 168 (8) |
| Br (15) | 4399 | 3354 | 4342 | 252 |
| C (15M) | 4473 | 3557 | 4423 | 252 |

TABLE 15

Bond lengths [Å] and angles [°] for mvMOF-5-ACEF.

| | | | |
|---|---|---|---|
| Zn(1)-O(4)#1 | 1.838 (14) | C(3)-C(4)#2 | 1.25 (4) |
| Zn(1)-O(4) | 1.838 (14) | C(3)-H(3) | 0.9500 |
| Zn(1)-O(2) | 1.85 (2) | C(4)-C(3)#2 | 1.25 (4) |
| Zn(1)-O(1) | 1.961 (13) | C(4)-H(4) | 0.9500 |
| Zn(2)-O(7) | 1.857 (15) | C(5)-C(6) | 1.66 (3) |
| Zn(2)-O(8) | 1.859 (14) | C(6)-C(8) | 1.38 (3) |
| Zn(2)-O(5) | 1.864 (14) | C(6)-C(7) | 1.47 (3) |
| Zn(2)-O(1) | 1.920 (7) | C(7)-C(8)#3 | 1.29 (3) |

TABLE 15-continued

Bond lengths [Å] and angles [°] for mvMOF-5-ACEF.

| | | | |
|---|---|---|---|
| Zn(2)-Zn(3) | 3.157 (3) | C(7)-H(7) | 0.9500 |
| Zn(3)-O(6)#1 | 1.853 (15) | C(8)-C(7)#3 | 1.29 (3) |
| Zn(3)-O(6) | 1.853 (15) | C(8)-H(8) | 0.9500 |
| Zn(3)-O(3) | 1.864 (19) | C(9)-C(10) | 1.68 (3) |
| Zn(3)-O(1) | 1.943 (14) | C(10)-C(11) | 1.45 (3) |
| Zn(3)-Zn(2)#1 | 3.157 (3) | C(10)-C(12) | 1.45 (3) |
| O(1)-Zn(2)#1 | 1.920 (7) | C(11)-C(12)#4 | 1.31 (3) |
| O(2)-C(1) | 1.22 (4) | C(11)-H(11) | 0.9500 |
| O(3)-C(1) | 1.33 (3) | C(12)-C(11)#4 | 1.31 (3) |
| O(4)-C(5) | 1.23 (2) | C(12)-H(12) | 0.9500 |
| O(5)-C(5) | 1.32 (2) | C(13)-O(8)#1 | 1.291 (16) |
| O(6)-C(9) | 1.28 (2) | C(13)-C(14) | 1.68 (4) |
| O(7)-C(9) | 1.27 (2) | C(14)-C(15)#1 | 1.43 (2) |
| O(8)-C(13) | 1.291 (16) | C(14)-C(15) | 1.43 (2) |
| C(1)-C(2) | 1.71 (3) | C(15)-C(15)#5 | 1.26 (3) |
| C(2)-C(4) | 1.38 (4) | C(15)-H(15) | 0.9500 |
| C(2)-C(3) | 1.44 (4) | | |
| O(4)#1-Zn(1)-O(4) | 106.5 (9) | O(4)-Zn(1)-O(2) | 106.3 (5) |
| O(4)#1-Zn(1)-O(2) | 106.3 (5) | O(4)#1-Zn(1)-O(1) | 111.9 (5) |
| O(4)-Zn(1)-O(1) | 111.9 (5) | Zn(2)-O(1)-Zn(3) | 109.6 (5) |
| O(2)-Zn(1)-O(1) | 113.5 (7) | Zn(2)#1-O(1)-Zn(1) | 109.2 (5) |
| O(7)-Zn(2)-O(8) | 105.4 (6) | Zn(2)-O(1)-Zn(1) | 109.2 (5) |
| O(7)-Zn(2)-O(5) | 105.9 (6) | Zn(3)-O(1)-Zn(1) | 108.3 (6) |
| O(8)-Zn(2)-O(5) | 106.7 (6) | C(1)-O(2)-Zn(1) | 126 (2) |
| O(7)-Zn(2)-O(1) | 113.0 (6) | C(1)-O(3)-Zn(3) | 125 (2) |
| O(8)-Zn(2)-O(1) | 112.2 (5) | C(5)-O(4)-Zn(1) | 128.2 (15) |
| O(5)-Zn(2)-O(1) | 113.0 (6) | C(5)-O(5)-Zn(2) | 124.8 (13) |
| O(7)-Zn(2)-Zn(3) | 77.6 (5) | C(9)-O(6)-Zn(3) | 124.1 (16) |
| O(8)-Zn(2)-Zn(3) | 125.2 (4) | C(9)-O(7)-Zn(2) | 124.4 (15) |
| O(5)-Zn(2)-Zn(3) | 125.4 (4) | C(13)-O(8)-Zn(2) | 126.0 (16) |
| O(1)-Zn(2)-Zn(3) | 35.4 (4) | O(2)-C(1)-O(3) | 134 (3) |
| O(6)#1-Zn(3)-O(6) | 106.4 (9) | O(2)-C(1)-C(2) | 118 (3) |
| O(6)#1-Zn(3)-O(3) | 105.7 (6) | O(3)-C(1)-C(2) | 108 (3) |
| O(6)-Zn(3)-O(3) | 105.7 (6) | C(4)-C(2)-C(3) | 126 (3) |
| O(6)#1-Zn(3)-O(1) | 112.8 (5) | C(4)-C(2)-C(1) | 122 (3) |
| O(6)-Zn(3)-O(1) | 112.8 (5) | C(3)-C(2)-C(1) | 112 (3) |
| O(3)-Zn(3)-O(1) | 112.9 (8) | C(4)#2-C(3)-C(2) | 115 (4) |
| O(6)#1-Zn(3)-Zn(2)#1 | 77.8 (5) | C(4)#2-C(3)-H(3) | 122.3 |
| O(6)-Zn(3)-Zn(2)#1 | 126.2 (4) | C(2)-C(3)-H(3) | 122.3 |
| O(3)-Zn(3)-Zn(2)#1 | 125.1 (5) | C(3)#2-C(4)-C(2) | 118 (4) |
| O(1)-Zn(3)-Zn(2)#1 | 34.95 (18) | C(3)#2-C(4)-H(4) | 120.9 |
| O(6)#1-Zn(3)-Zn(2) | 126.2 (4) | C(2)-C(4)-H(4) | 120.9 |
| O(6)-Zn(3)-Zn(2) | 77.8 (5) | O(4)-C(5)-O(5) | 133 (2) |
| O(3)-Zn(3)-Zn(2) | 125.1 (5) | O(4)-C(5)-C(6) | 119 (2) |
| O(1)-Zn(3)-Zn(2) | 34.95 (18) | O(5)-C(5)-C(6) | 108.5 (18) |
| Zn(2)#1-Zn(3)-Zn(2) | 60.10 (9) | C(8)-C(6)-C(7) | 124 (2) |
| Zn(2)#1-O(1)-Zn(2) | 110.8 (6) | C(8)-C(6)-C(5) | 121 (2) |
| Zn(2)#1-O(1)-Zn(3) | 109.6 (5) | C(7)-C(6)-C(5) | 115 (2) |
| C(8)#3-C(7)-C(6) | 119 (2) | C(10)-C(11)-H(11) | 121.1 |
| C(8)#3-C(7)-H(7) | 120.3 | C(11)#4-C(12)-C(10) | 116 (3) |
| C(6)-C(7)-H(7) | 120.3 | C(11)#4-C(12)-H(12) | 122.1 |
| C(7)#3-C(8)-C(6) | 116 (2) | C(10)-C(12)-H(12) | 122.1 |
| C(7)#3-C(8)-H(8) | 122.0 | O(8)-C(13)-O(8)#1 | 133 (3) |
| C(6)-C(8)-H(8) | 122.0 | O(8)-C(13)-C(14) | 113.6 (14) |
| O(7)-C(9)-O(6) | 136 (2) | O(8)#1-C(13)-C(14) | 113.6 (14) |
| O(7)-C(9)-C(10) | 112 (2) | C(15)#1-C(14)-C(15) | 127 (3) |
| O(6)-C(9)-C(10) | 112 (2) | C(15)#1-C(14)-C(13) | 116.5 (14) |
| C(11)-C(10)-C(12) | 126 (2) | C(15)-C(14)-C(13) | 116.5 (14) |
| C(11)-C(10)-C(9) | 116 (2) | C(15)#5-C(15)-C(14) | 116.3 (14) |
| C(12)-C(10)-C(9) | 117 (2) | C(15)#5-C(15)-H(15) | 121.8 |
| C(12)#4-C(11)-C(10) | 118 (3) | C(14)-C(15)-H(15) | 121.8 |
| C(12)#4-C(11)-H(11) | 121.1 | | |

Symmetry Transformations Used to Generate Equivalent Atoms:

1 x, −y + 1, z #2 −x, −y + 1, −z #3 −x + ½, −y + ½, −z
4 −x + ½, −y + ½, −z + 1 #5 −x + 1, y, −z + 1

TABLE 16

Anisotropic displacement parameters ($Å^2 \times 10^3$) for mvMOF-5-ACEF.

| | $U^{11}$ | $U^{22}$ | $U^{33}$ | $U^{23}$ | $U^{13}$ | $U^{12}$ |
|---|---|---|---|---|---|---|
| Zn(1) | 119 (3) | 115 (3) | 82 (2) | 0 | 56 (2) | 0 |
| Zn(2) | 118 (2) | 108 (2) | 92 (2) | 4 (1) | 60 (2) | 4 (1) |
| Zn(3) | 120 (3) | 112 (3) | 93 (2) | 0 | 65 (2) | 0 |

The anisotropic displacement factor exponent takes the form: $-2\pi^2[h^2 a^{*2}U^{11} + \ldots + 2 h k a^* b^* U^{12}]$

TABLE 17

Hydrogen coordinates ($\times 10^4$) and isotropic displacement parameters ($Å^2 \times 10^3$) for ACEF.

| | x | y | z | U(eq) |
|---|---|---|---|---|
| H(3) | 448 | 5000 | −692 | 283 |
| H(4) | 430 | 5000 | 1575 | 270 |
| H(7) | 1964 | 3534 | −701 | 283 |
| H(8) | 3092 | 2384 | 1608 | 278 |
| H(11) | 3070 | 2374 | 4534 | 295 |
| H(12) | 1908 | 3525 | 4541 | 303 |
| H(15) | 4560 | 3847 | 4501 | 252 |

Porosity of mvMOFs, $H_2$ Uptake and $CO_2$ Separation Study.

All low-pressure gas adsorption experiments (up to 1 bar) were performed on a Quantachrome Autosorb-1 automatic volumetric instrument. A liquid nitrogen bath (77 K) and a liquid argon bath (87 K) were used for $N_2$, $H_2$ and Ar, while a thermostated bath (273, 283, and 298 K) was used for the $CO_2$ and CO isotherm measurements. Ultra-high purity grade $N_2$, $H_2$, Ar, CO, He (99.999% purity) and $CO_2$ gases (99.995% purity) were used throughout the adsorption experiments. Non-ideality of gases was obtained from the second virial coefficient at experimental temperature. For measurement of the apparent surface areas, the Langmuir method was applied using the adsorption branches of the $N_2$ (Ar) isotherms assuming a $N_2$ (Ar) cross-sectional area of 16.2 (14.2) $Å^2$/molecule. As-synthesized samples of MOFs were immersed in chloroform at ambient temperature for three 24 h period, evacuated at ambient temperature for 12 h.

Figure 45:
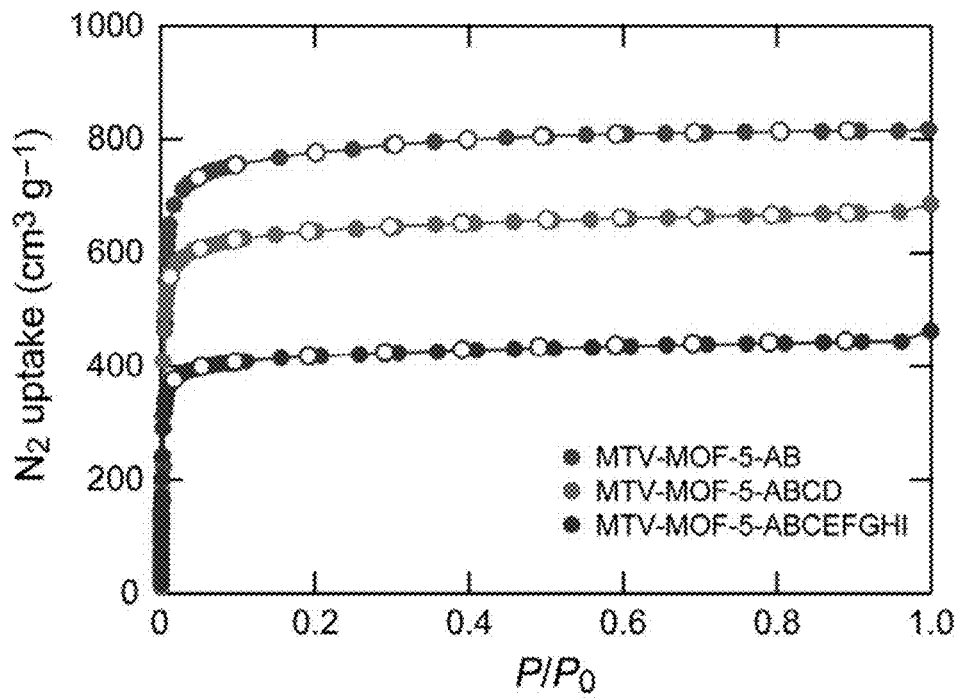
FIG. 45 shows nitrogen adsorption isotherms for mvMOF-5-AB (top), -ABCD (middle), and -ABCEFGHI (bottom) measured at 77 K. Filled and open symbols represent adsorption and desorption branches, respectively. Connecting traces are guides for eye.
Figure 46:
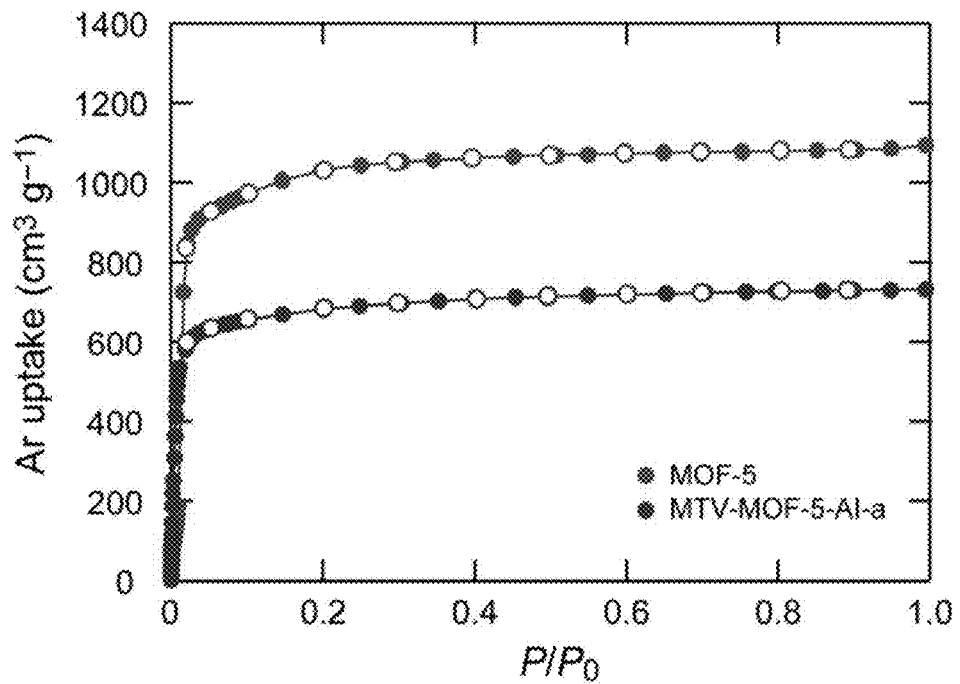
FIG. 46 shows argon adsorption isotherms for mvMOF-5 (top) and mvMOF-5-AI (bottom) measured at 87 K. Filled and open symbols represent adsorption and desorption branches, respectively. Connecting traces are guides for eye.
Figure 47:
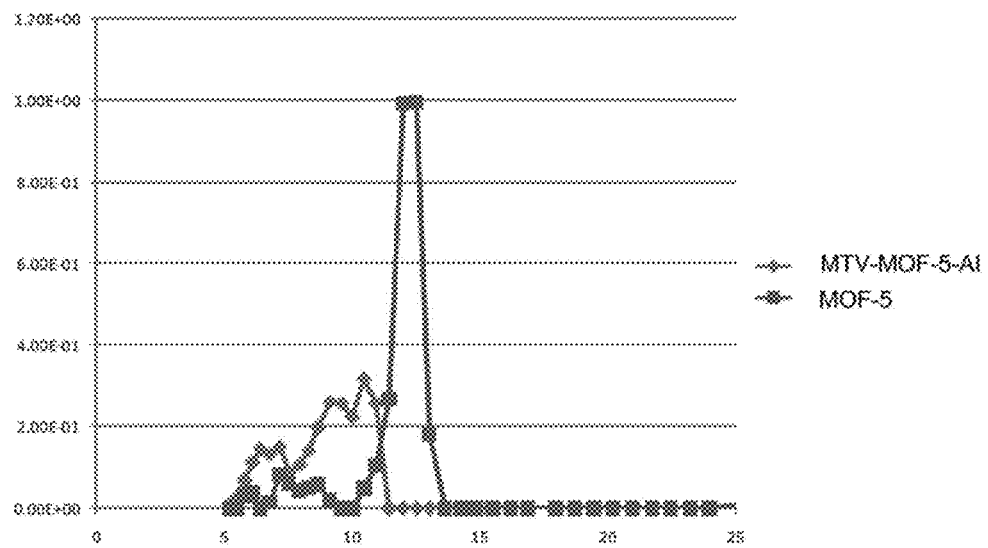
FIG. 47 shows the calculated pore size distribution of mvMOF-5-AI-a and MOF-5 based on NLDFT model.
Figure 48:
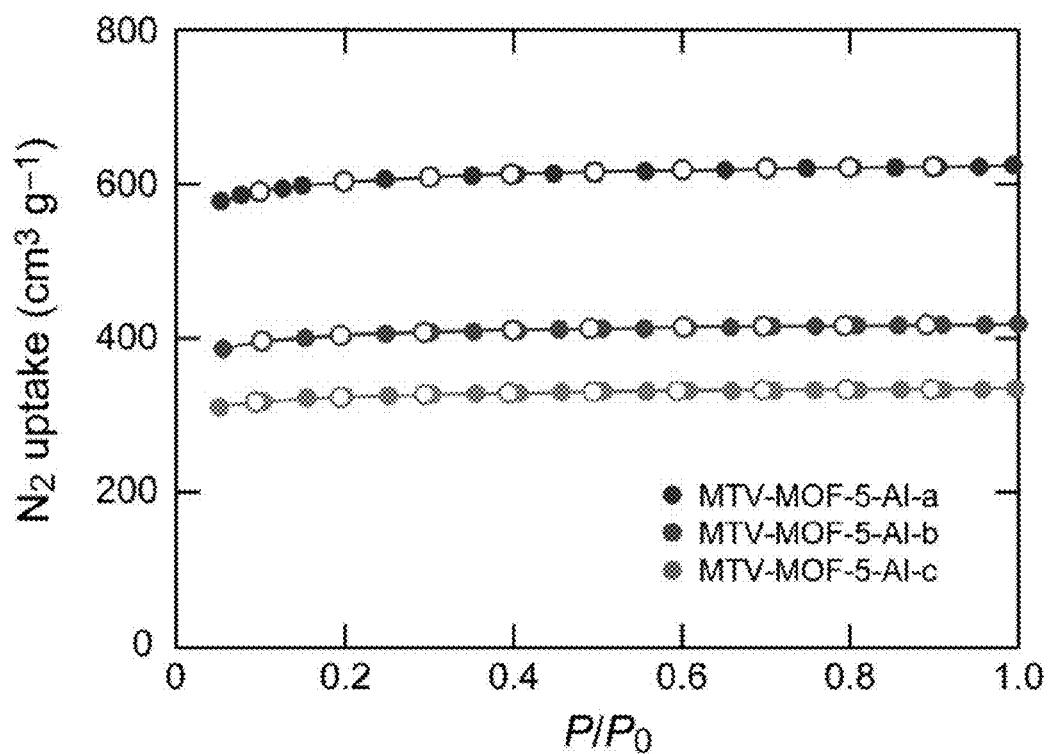
FIG. 48 shows nitrogen adsorption isotherms for MOF-5-AI-a (top), mvMOF-5-AI-b (middle) and mvMOF-5-AI-c measured at 77 K. Filled and open symbols represent adsorption and desorption branches, respectively. Connecting traces are guides for eye.
Figure 49:
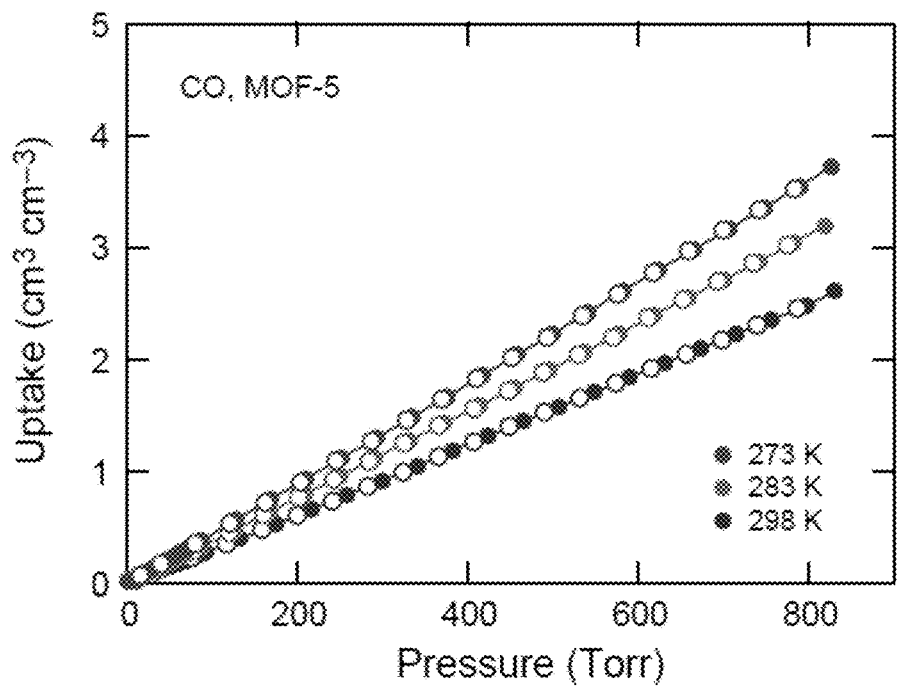
FIG. 49 shows CO isotherms for MOF-5 taken at 273 (top), 283 (middle) and 298 K (bottom). Filled and open symbols represent adsorption and desorption branches. Connecting traces are guides for eye.
Figure 50:
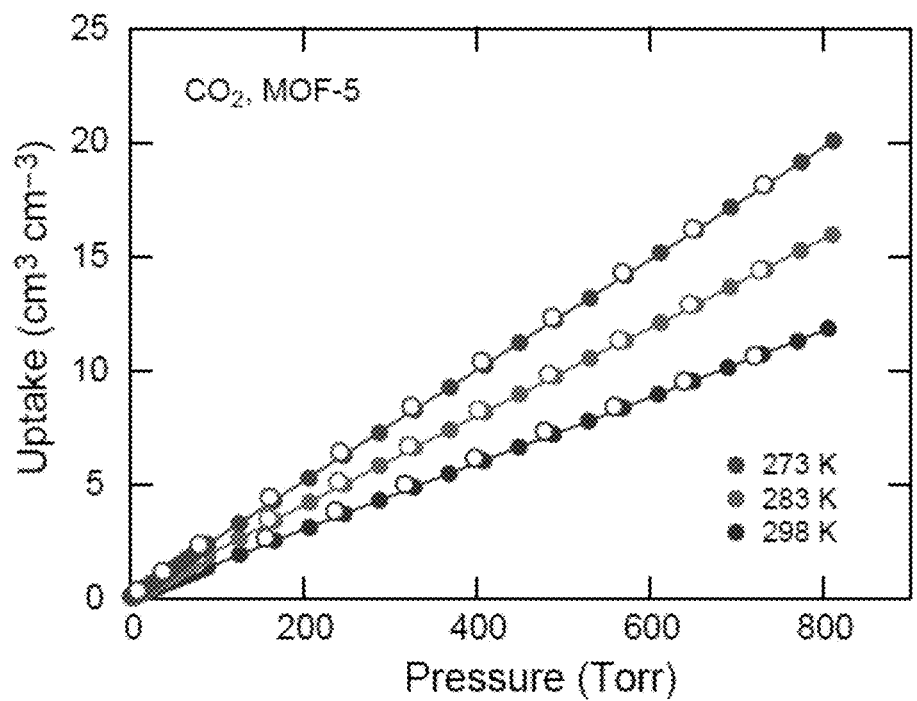
FIG. 50 shows $CO_2$ isotherms for MOF-5 taken at 273 (top), 283 (middle) and 298 K (bottom). Filled and open symbols represent adsorption and desorption branches. Connecting traces are guides for eye.
Figure 51:
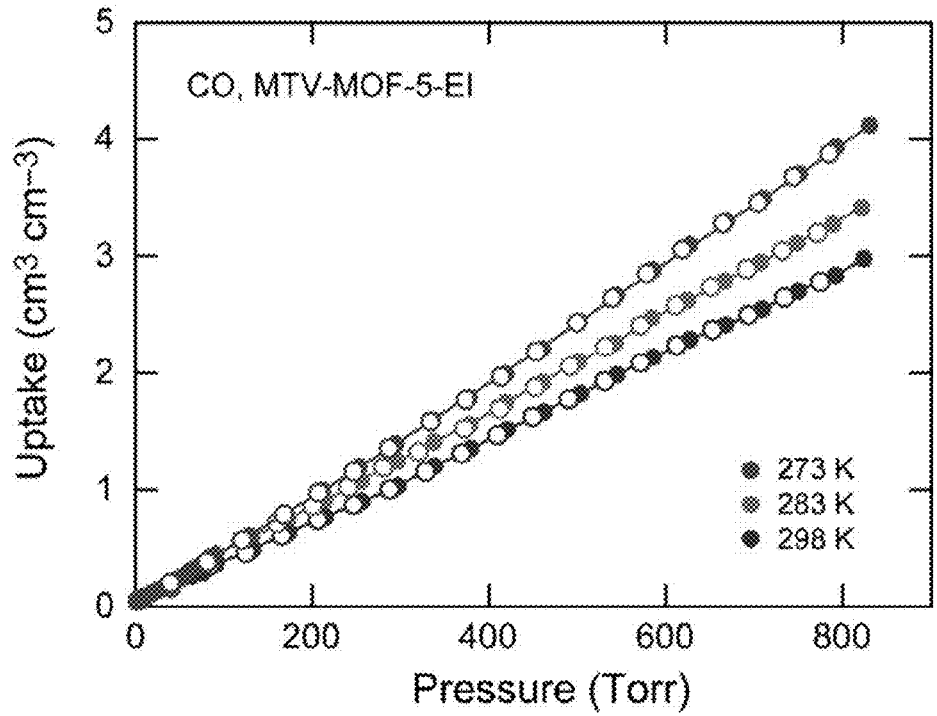
FIG. 51 shows CO isotherms for mvMOF-5-EI taken at 273 (top), 283 (middle) and 298 K (bottom). Filled and open symbols represent adsorption and desorption branches. Connecting traces are guides for eye.
Figure 52:
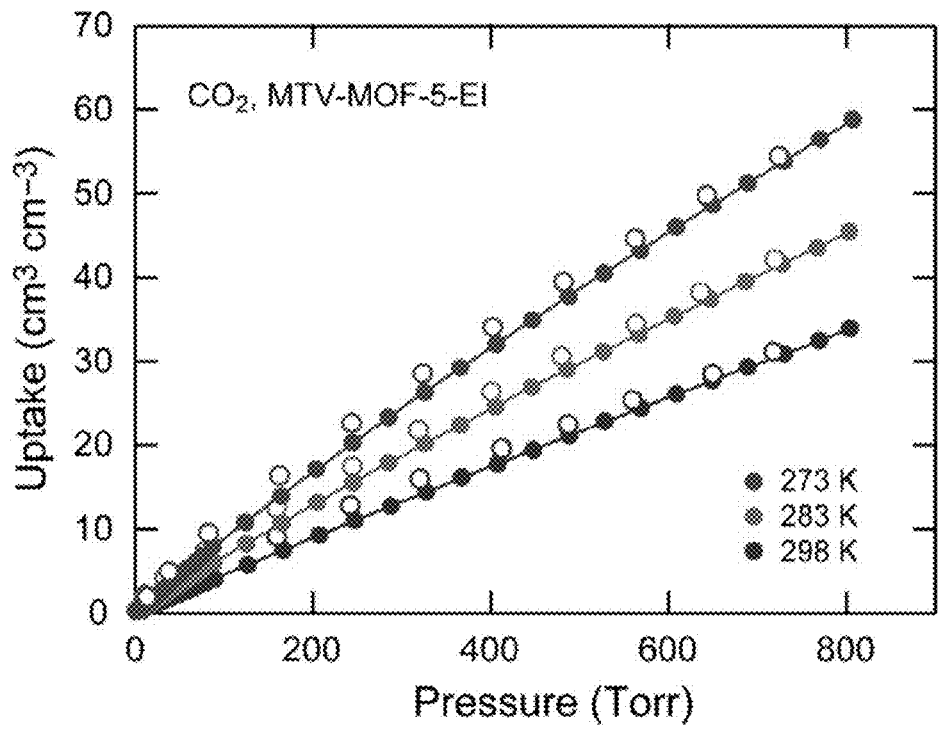
FIG. 52 shows $CO_2$ isotherms for mvMOF-5-EI taken at 273 (top), 283 (middle) and 298 K (bottom). Filled and open symbols represent adsorption and desorption branches. Connecting traces are guides for eye.
Figure 53:
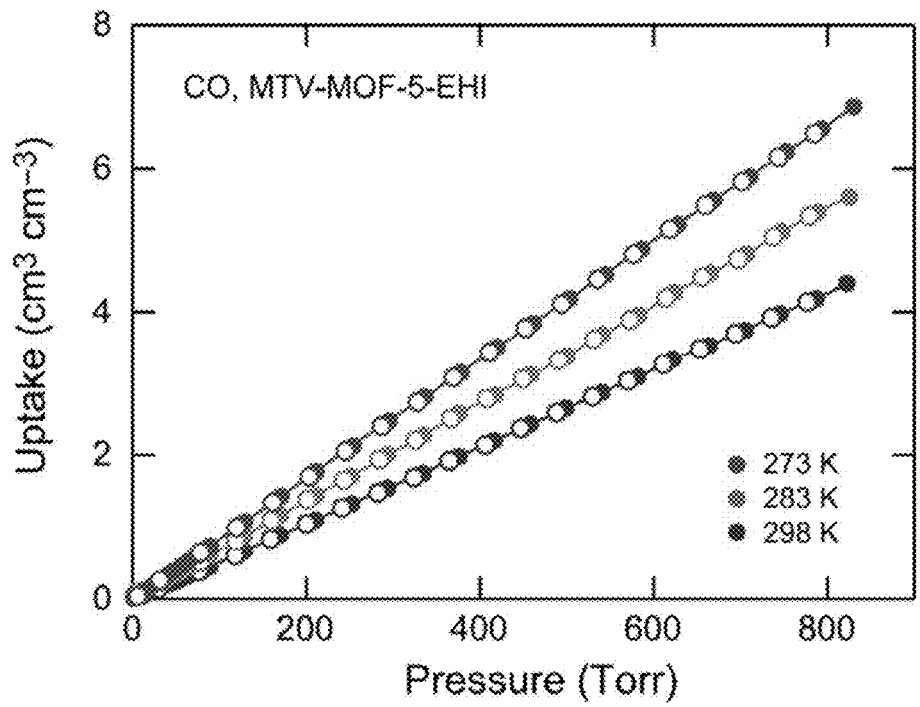
FIG. 53 shows CO isotherms for mvMOF-5-EHI taken at 273 (top), 283 (middle) and 298 K (bottom). Filled and open symbols represent adsorption and desorption branches. Connecting traces are guides for eye.
Figure 54:
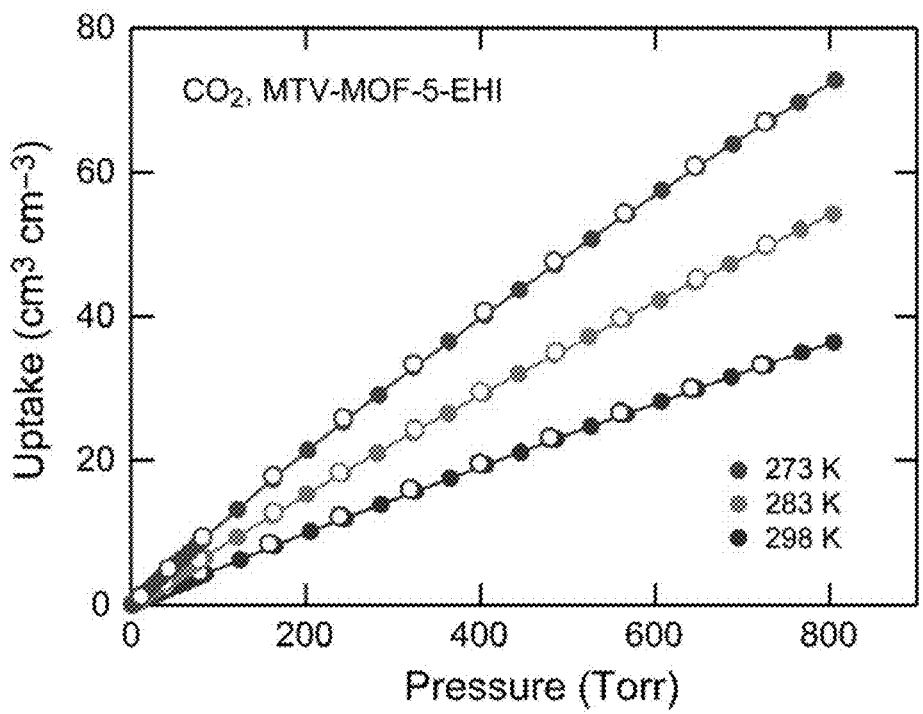
FIG. 54 shows $CO_2$ isotherms for mvMOF-5-EHI taken at 273 (top), 283 (middle) and 298 K (bottom). Filled and open symbols represent adsorption and desorption branches. Connecting traces are guides for eye.

The architectural rigidity and consequently the permanent porosity of evacuated MOF-5, mvMOF-5-AB, -AI-a, -ABCD, and -ABCEFGHI were unequivocally proven by gas-sorption analysis. Type I $N_2$/Ar adsorption isotherm behavior was observed for these MOFs (FIGS. 45 and 46), revealing their microporous nature. The Langmuir surface area of mvMOF-AB was calculated to be 3640 $m^2/g$. Similarly, the apparent surface areas of MOF-5, mvMOF-5-AI-a, -ABCD, and -ABCEFGHI were calculated to be 4140, 2680, 2860, and 1860 $m^2/g$, respectively. In the MVMOF-5-AI series, as more bulky link I was introduced into crystal product, the calculated density increases from -a to -c, and surface area decreases (FIG. 48).

TABLE 18

Summary of porosity measurements for MOF-5, and mvMOFs.

| Compound | BET SA ($m^2/g$) | Langmuir SA ($m^2/g$) | Pore volume ($cm^3/g$) | $H_2$ uptake at 760 torr ($cm^3/g$) | Bulk density ($g/cm^3$) |
|---|---|---|---|---|---|
| MOF-5 | 3320 | 4150 | 1.37 | 139 | 0.59 |
| mvMOF-5-AB | 2980 | 3440 | 1.22 | 133 | 0.61 |
| mvMOF-5-AC | 2140 | 2580 | 0.92 | 122 | 0.66 |

TABLE 18-continued

Summary of porosity measurements for MOF-5, and mvMOFs.

| Compound | BET SA (m²/g) | Langmuir SA (m²/g) | Pore volume (cm³/g) | H₂ uptake at 760 torr (cm³/g) | Bulk density (g/cm³) |
|---|---|---|---|---|---|
| mvMOF-5-AD | 1710 | 2110 | 0.75 | 101 | 0.65 |
| mvMOF-5-AE | 2490 | 3020 | 1.08 | 132 | 0.62 |
| mvMOF-5-AF | 2400 | 2920 | 1.04 | 140 | 0.63 |
| mvMOF-5-AG | 2410 | 2860 | 1.02 | 139 | 0.63 |
| mvMOF-5-AH | 2240 | 2760 | 0.98 | 172 | 0.67 |
| mvMOF-5-AI-a | 2230 | 2680 | 0.88 | 177 | 0.74 |
| mvMOF-5-AI-b | 1500 | 1800 | 0.64 | 137 | 0.83 |
| mvMOF-5-AI-c | 1210 | 1440 | 0.51 | 130 | 0.93 |
| mvMOF-5-EI | 1020 | 1210 | 0.43 | | 1.02 |
| mvMOF-5-AHI | 1820 | 2210 | 0.79 | 189 | 0.81 |
| mvMOF-5-EHI | 1176 | 1400 | 0.50 | 156 | 0.90 |
| mvMOF-5-ABCD | 2460 | 2860 | 1.00 | | 0.69 |
| mvMOF-5-ACEF | 1920 | 2400 | 0.83 | | 0.65 |
| mvMOF-5-ABCEFGHI | 1640 | 1860 | 0.65 | | 0.72 |

Pore size distribution analysis of mvMOF-5-AI and MOF-5. In addition, the pore size distribution of one of the mvMOF with bulky link was studied, MOF-5-AI-a. The fit of Ar adsorption isotherm for MOF-5-AI-a with a nonlocal density functional theory (NLDFT) model reveals that the pore size distribution is largely populated smaller than 12 Å, which is a typical pore size distribution of MOF-5 (FIG. 40). This indicates that almost all larger cages of MOF-5-AI-a are partially functionalized by link I, no pore environment of MOF-5 exists.

CO₂ and CO adsorption isotherms for mvMOF-5-EI are illustrated in FIGS. 47-50, respectively. To estimate reliable Henry's constants, a virial-type expression comprising the temperature-independent parameters a, and b, was applied:

$$\ln P = \ln N + \frac{1}{T}\sum_{i=0}^{m} a_i N^i + \sum_{i=0}^{n} b_i N^i \quad (1)$$

where P is pressure, N is the adsorbed amount, T is temperature, and m and n represent the number of coefficients required to adequately describe the isotherms. From these results, the Henry's constant ($K_H$) is calculated from where T is temperature.

$$K_H = \exp(-b_0)\cdot\exp(-a_0/T) \quad (2)$$

The Henry's Law selectivity for gas component i over j at 298 K is calculated based on eq. (3).

$$S_{ij} = K_{Hi}/K_{Hj} \quad (3)$$

A number of embodiments of the invention have been described. Nevertheless, it will be understood that various modifications may be made without departing from the spirit and scope of the invention. Accordingly, other embodiments are within the scope of the following claims.

What is claimed is:

1. A porous multi-variate metal organic framework (mvMOF) comprising a plurality of linking moieties wherein one or more linking moieties have a general structure selected from the group consisting of

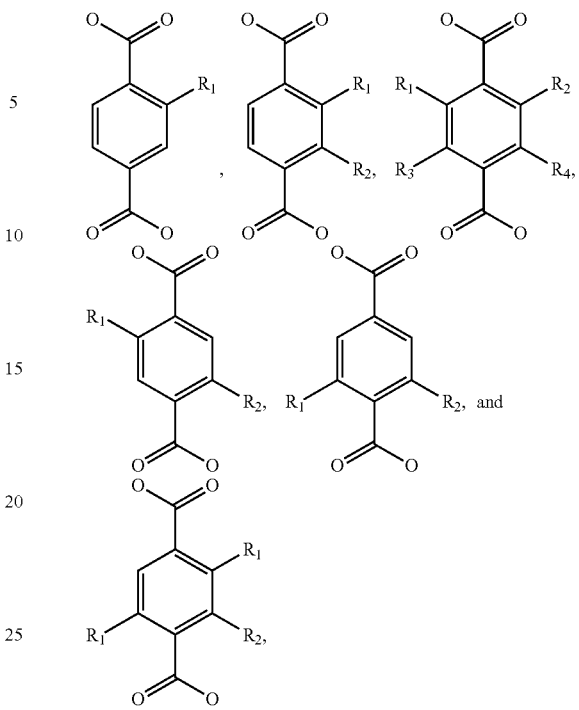

wherein functional groups $R_1$-$R_4$ are selected from the group consisting of —H, —NH₂, —BR, —Cl, —NO₂, —CH₃, —OCH₂R₅, and —O—CH₂R₆, wherein $R_5$ is an alkyl or alkene of from about 1-5 carbons, and $R_6$ is an aryl or substitute aryl, or wherein $R_1$-$R_2$ when adjacent can form a ring and wherein the functional groups between at least two or more linking moieties are non-uniform, and wherein the functional groups of one or more linking moieties do not adversely affect the connectivity or spatial orientation of the linking clusters to one or more metals or metal ions, and wherein the functional groups modify the chemical and physical properties of a pore in the framework.

2. The mvMOF of claim 1, wherein the mvMOF is constructed of three or more linking moieties that have non-uniform functional groups.

3. The mvMOF of claim 1, wherein the mvMOF comprises repeating units of one or more linking moieties joined to one or more metal or metal ions through one or more linking clusters, and a plurality of functional groups which are covalently bound to the linking moieties, wherein the functional groups are heterogeneous and/or wherein the functional groups are positional isomers.

4. The mvMOF of claim 1, wherein each of the pores within the framework comprise a plurality of different functional groups pointing into the center of a pore.

5. The mvMOF of claim 1, wherein the framework comprises a topology of a MOF-5 framework.

6. The mvMOF of claim 1, wherein the framework comprise a metal ion selected from the group consisting of: Li⁺, Na⁺, Rb⁺, Mg²⁺, Ca²⁺, Sr²⁺, Ba²⁺, Sc³⁺, Ti⁴⁺, Zr⁴⁺, Ta³⁺, Cr³⁺, Mo³⁺, W³⁺, Mn³⁺, Fe³⁺, Fe²⁺, Ru³⁺, Ru²⁺, Os³⁺, Os²⁺, Co³⁺, Co²⁺, Ni²⁺, Ni⁺, Pd²⁺, Pd⁺, Pt²⁺, Pt⁺, Cu²⁺, Cu⁺, Au⁺, Zn²⁺, Al³⁺, Ga³⁺, In³⁺, Si⁴⁺, Si²⁺, Ge⁴⁺, Ge²⁺, Sn⁴⁺, Sn²⁺, Bi⁵⁺, Bi³⁺, and combinations thereof, along with corresponding metal salt counter-anions.

7. The mvMOF of claim 1, wherein the linking moiety comprises a structure selected from the group consisting of:

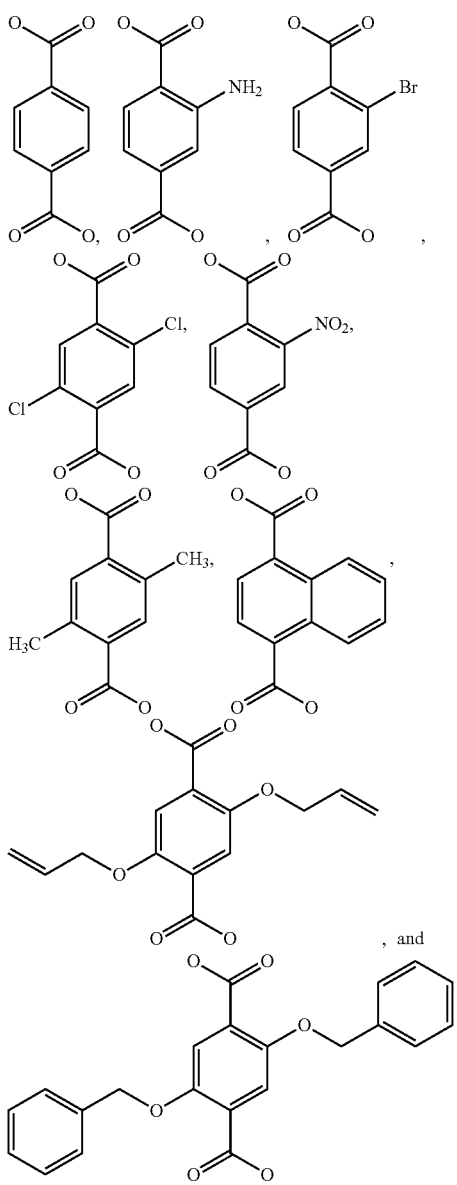

8. The mvMOF of claim 1, wherein one or more functional groups of one or more linking moieties can be (1) selectively reacted with a post-framework reactant so as to add to, eliminate, or substitute at least one functional group of one or more linking moieties, but wherein at least one other functional group of a linking moiety does not react with the post-framework reactant, and wherein (1) is repeated from 0 to 10 times.

9. The mvMOF of claim 1, made by a process comprising mixing a plurality of chemically functionalized linking moieties with a metal ion or metal containing salt, wherein the linking moieties are at a desired ratio to incorporate the desired ratio of a particular combination of linking moieties into the organic framework, purifying the crystals and removing the solvent.

10. The mvMOF of claim 9, wherein the method comprises mixing a plurality of chemically functionalized linking moieties at desired ratios to incorporate the desired ratio of a particular combination of linking moieties into an organic framework comprising benzenedicarboxylic acid with zinc nitrate in DEF/DMF.

11. A gas separation device comprising the mvMOF of claim 1.

12. A gas storage device comprising the mvMOF of claim 1.

13. The mvMOF of claim 1, wherein the mvMOF comprises improved gas sorption capacity compared to a MOF having the same topology but homogenous linking moieties.

14. The mvMOF of claim 1, wherein one or more functional groups and/or one or more post-framework reactants modifies at least one property of the mvMOF framework selected from the group consisting of:
   modulates the gas storage ability of the mvMOF framework;
   modulates the sorption properties of the mvMOF framework;
   modulates the pore size of the mvMOF framework;
   modulates the catalytic activity of the mvMOF framework;
   modulates the conductivity of the mvMOF framework; and
   modulates the sensitivity of the mvMOF framework to the presence of an analyte of interest.

15. The mvMOF of claim 14, wherein one or more functional groups and/or one or more post-framework reactants modifies at least two properties of the mvMOF framework selected from the group consisting of:
   modulates the gas storage ability of the mvMOF framework;
   modulates the sorption properties of the mvMOF framework;
   modulates the pore size of the mvMOF framework;
   modulates the catalytic activity of the mvMOF framework;
   modulates the conductivity of the mvMOF framework; and
   modulates the sensitivity of the mvMOF framework to the presence of an analyte of interest.

16. The mvMOF of claim 5, wherein the framework comprising a topology of a MOF-5 framework is selected from the group consisting of mvMOF-5-AB, -AC, -AD, -AE, -AF, -AG, -AH, -AI, -EI, -ABC, -AHI, -EHI, -ABCD, -ACEF, -ABCHI, -ABCGHI, -ABCEFHI, and -ABCEFGHI.

17. The process of claim 9, wherein the chemically functionalized linking moieties results from reacting a linking moiety comprising carboxylic acid-based linking clusters with one or more functionalizing reagents, and wherein the carboxylic acid-based linking clusters may or may not be first protected with a protecting group prior to reacting with one or more functionalization reagents and then may or may not be de-protected prior to mixing with a metal ion or metal containing salt.

18. The process of claim 9, wherein the chemically functionalized linking moieties results from reacting terephthalic acid with one or more functionalizing reagents.

19. A porous mvMOF comprising a plurality of linking moieties comprising one or more functional groups, wherein the functional groups between at least two or more linking moieties are non-uniform, and wherein the functional groups of one or more linking moieties do not adversely affect the connectivity or spatial orientation of the linking clusters to one or more metals or metal ions, and wherein the functional groups modify the chemical and physical properties of a pore in the framework.

20. The mvMOF of claim 19, wherein the linking moieties are comprised of organic parent chains selected from the group consisting of one or more optionally substituted aryls, heterocycles, cycloalkyls, cylcoalkenyls, or combinations thereof, and one or more linking clusters.

* * * * *